US008637857B2

(12) United States Patent
Langer et al.

(10) Patent No.: US 8,637,857 B2
(45) Date of Patent: Jan. 28, 2014

(54) SUBSTITUTED CARBAZOLE DERIVATIVES AND USE THEREOF IN ORGANIC ELECTRONICS

(75) Inventors: Nicolle Langer, Heppenheim (DE); Christian Schildknecht, Mannheim (DE); Soichi Watanabe, Mannheim (DE); Evelyn Fuchs, Mannheim (DE); Gerhard Wagenblast, Wachenheim (DE); Christian Lennartz, Schifferstadt (DE); Oliver Molt, Weinheim (DE); Korinna Dormann, Bad Dürkheim (DE); Arvid Hunze, Erlangen (DE); Ralf Krause, Erlangen (DE); Günter Schmid, Hemhofen (DE); Karsten Heuser, Erlangen (DE); Volker van Elsbergen, Aachen (DE); Herbert Friedrich Boerner, Aachen (DE)

(73) Assignees: BASF SE, Ludwigshafen (DE); Koninklijke Philips Electronics N.V., Eindhoven (NL); Osram Opto Semiconductor GmbH, Regensburg (DE)

( * ) Notice: Subject to any disclaimer, the term of this patent is extended or adjusted under 35 U.S.C. 154(b) by 471 days.

(21) Appl. No.: 13/080,091

(22) Filed: Apr. 5, 2011

(65) Prior Publication Data
US 2011/0266528 A1  Nov. 3, 2011

Related U.S. Application Data

(60) Provisional application No. 61/321,177, filed on Apr. 6, 2010.

(51) Int. Cl.
*H01L 29/08* (2006.01)
*H01L 35/24* (2006.01)
*H01L 51/00* (2006.01)

(52) U.S. Cl.
USPC .................................. 257/40; 257/E51.024

(58) Field of Classification Search
USPC ............................................ 257/40, E51.024
See application file for complete search history.

(56) References Cited

U.S. PATENT DOCUMENTS

2006/0258043 A1  11/2006  Bold et al. .................. 439/99
2009/0302743 A1  12/2009  Kato et al. .................. 313/504
(Continued)

FOREIGN PATENT DOCUMENTS

EP  0 906 947 A1  4/1999
EP  1 672 713 A1  6/2006
(Continued)

OTHER PUBLICATIONS

Vasudevan Dhayalan, et al., "A Versatile Synthesis of Annulated Carbazole Analogs Involving a Domino Reaction of Bromomethylindoles with Arenes/Heteroarenes", Eur. J. Org. Chem. 2009, pp. 531-546.

(Continued)

*Primary Examiner* — Phat X Cao
(74) *Attorney, Agent, or Firm* — Oblon, Spivak, McClelland, Maier & Neustadt, L.L.P.

(57) ABSTRACT

An organic light-emitting diode, organic solar cell or switching element comprising at least one substituted carbazole derivative of the general formula (I), (II) or (III)

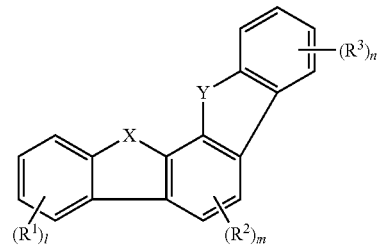

(I)

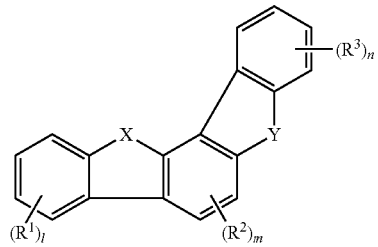

(II)

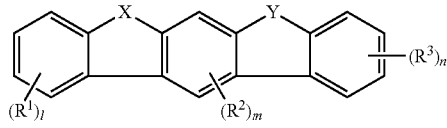

(III)

in which
X is $NR^4$, O, S or $PR^4$;
Y is $NR^5$, O, S or $PR^5$;
where at least one of the symbols X and Y is $NR^4$ or $NR^5$; substituted carbazole derivatives of the formula (I), (II) or (III); a light-emitting layer comprising at least one substituted carbazole derivative of the general formula (I), (II) or (III) and at least one emitter material; the use of substituted carbazole derivatives of the general formula (I), (II) or (III) as matrix material, hole/exciton blocker material and/or electron/exciton blocker material and/or hole injection material and/or electron injection material and/or hole conductor material and/or electron conductor material in an organic light-emitting diode, an organic solar cell or in a switching element, and a device selected from the group consisting of stationary visual display units, mobile visual display units, illumination units, keyboards, garments, furniture and wallpaper comprising at least one inventive organic light-emitting diode.

15 Claims, No Drawings

(56) References Cited

U.S. PATENT DOCUMENTS

| | | | |
|---|---|---|---|
| 2009/0309488 A1 | 12/2009 | Kato et al. | 313/504 |
| 2010/0012931 A1 | 1/2010 | Kato et al. | 257/40 |
| 2010/0187977 A1 | 7/2010 | Kai et al. | 313/504 |
| 2010/0237339 A1* | 9/2010 | Nomura et al. | 257/40 |

FOREIGN PATENT DOCUMENTS

| | | |
|---|---|---|
| EP | 1 942 171 A1 | 7/2008 |
| EP | 1 956 666 A1 | 8/2008 |
| WO | WO 2005/019373 A2 | 3/2005 |
| WO | WO 2005/113704 A2 | 12/2005 |
| WO | WO 2008/056746 A1 | 5/2008 |
| WO | WO 2009/148015 A1 | 12/2009 |
| WO | WO 2009/148016 A1 | 12/2009 |
| WO | WO 2009/148062 A1 | 12/2009 |

OTHER PUBLICATIONS

M. A. Baldo, et al., "Very High-Efficiency Green Organic Light-Emitting Devices Based on Electrophosphorescence", Applied Physics Letters, Jul. 5, 1999, vol. 75, No. 1, pp. 4-6.

Ping-I Shih, et al., "Novel Carbazole/Fluorene Hybrids: Host Materials for Blue Phosphorescent OLEDs", Organic Letters, vol. 8, No. 13, 2006, pp. 2799-2802.

Teruhisa Tsuchimoto, et al., "Indium-Catalyzed Annulation of 2-Aryl- and 2-Heteroarylindoles with Propargyl Ethers: Concise Synthesis and Photophysical Properties of Diverse Aryl- and Heteroaryl-Annulated[a]Carbazoles", J. Am. Chem. Soc. 2008, 130, pp. 15823-15835.

* cited by examiner

SUBSTITUTED CARBAZOLE DERIVATIVES AND USE THEREOF IN ORGANIC ELECTRONICS

The present invention relates to an organic light-emitting diode (OLED), to an organic solar cell (organic photovoltaics), and to a switching element such as an organic transistor, for example an organic FET and an organic TFT, comprising at least one substituted carbazole derivative selected from indolocarbazoles, benzofuranylcarbazoles and benzothiophenylcarbazoles, to a light-emitting layer comprising at least one substituted carbazole derivative selected from indolocarbazoles, benzofuranylcarbazoles and benzothiophenylcarbazoles, to the use of substituted carbazole derivatives selected from indolocarbazoles, benzofuranylcarbazoles and benzothiophenylcarbazoles as matrix material, hole/exciton blocker material and/or electron/exciton blocker material and/or hole injection material and/or electron injection material and/or hole conductor material and/or electron conductor material in an organic light-emitting diode, an organic solar cell and a switching element such as an organic transistor, and to a device selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; garments; furniture and wallpaper comprising at least one inventive organic light-emitting diode.

Organic electronics is a subfield of electronics and uses electronic circuits which comprise polymers or smaller organic compounds. Fields of use of organic electronics are the use of polymers or smaller organic compounds in organic light-emitting diodes (OLEDs), use in organic solar cells (organic photovoltaics) and in switching elements such as organic transistors, for example organic FETs and organic TFTs.

The use of suitable novel organic materials makes it possible to provide various novel components based on organic electronics, such as displays, sensors, transistors, data stores or photovoltaic cells. This makes possible the development of new applications which are thin, light, flexible and producible at low cost.

A preferred field of use according to the present application is the use of relatively small organic compounds in organic light-emitting diodes.

Organic light-emitting diodes (OLEDs) exploit the property of materials of emitting light when they are excited by electrical current. OLEDs are of particular interest as an alternative to cathode ray tubes and to liquid-crystal displays for producing flat visual display units. Due to the very compact design and the intrinsically low power consumption, devices comprising OLEDs are especially suitable for mobile applications, for example for applications in cellphones, laptops, digital cameras, MP3 players, etc., and for illumination.

The basic principles of the functioning of OLEDs and suitable configurations (layers) of OLEDs are known to those skilled in the art and are specified, for example, in WO 2005/113704 and the literature cited therein. The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (triplet emitters) (M. A. Baldow et al., Appl. Phys. Lett. 1999, 75, 4 to 6). For quantum-mechanical reasons, when the triplet emitters (phosphorescence emitters) are used, up to four times the quantum efficiency, energy efficiency and power efficiency is possible. In order to implement the advantages of the use of the organometallic triplet emitters (phosphorescence emitters) in practice, it is necessary to provide device compositions which have a high operative lifetime, a good efficiency, a high stability to thermal stress and a low use and operating voltage.

Such device compositions may, for example, comprise specific matrix materials in which the actual light emitter is present in distributed form. In addition, the compositions may comprise blocker materials, it being possible for hole, exciton and/or electron blockers to be present in the device compositions. Additionally or alternatively, the device compositions may further comprise hole injection materials and/or electron injection materials and/or hole conductor materials and/or electron conductor materials. The selection of the aforementioned materials which are used in combination with the actual light emitter has a substantial influence on properties including the efficiency and the lifetime of the OLEDs.

The prior art proposes numerous different materials for use in the different layers of OLEDs.

WO 2008/056746 A1 relates to OLEDs having a light-emitting layer which comprises a phosphorescent dopant material and an indolocarbazole derivative as matrix material. According to WO 2008/056746 A1, it is essential that the indolocarbazole derivative is substituted by a nitrogen-containing heteroaryl radical on at least one of the nitrogen atoms.

EP 1 956 666 A1 relates to an OLED which has an improved luminescence efficiency. The OLED comprises a hole transport layer, a light-emitting layer and an electron transport layer, which are arranged between an anode and a cathode. The light-emitting layer comprises a phosphorescent dopant material and an indolocarbazole compound with a specific structure. All indolocarbazole derivatives mentioned in EP 1 956 666 A1 have, apart from a substitution on the nitrogen atom, either no further substituents or exclusively unsubstituted phenyl substituents. In addition, EP 1 956 666 A1 mentions triazatruxenes.

EP 0 906 947 A1 relates to an OLED which comprises an indolocarbazole derivative as a charge transport component. All indolocarbazole derivatives mentioned by way of example have, apart from a substitution on the nitrogen atom, either no further substituents on the carbazole skeleton or exclusively methyl groups.

EP 1 672 713 A1 relates to OLEDs having compounds which comprise indolocarbazole units. According to the examples in EP 1 672 713 A1, the indolocarbazole derivatives are either at least dimeric indolocarbazole derivatives which have no substituents or sulfur-containing substituents, or monomeric indolocarbazole derivatives substituted by chlorine or bromine or a long-chain alkyl radical ($C_8H_{17}$).

EP 1 942 171 A1 relates to an OLED which comprises a pyrene-substituted benzofuranyl, benzothiophenyl or indonyl compound. According to EP 1 942 171 A1, the presence of the pyrene radical is essential for the properties of the OLED specified in EP 1 942 171 A1.

J. Am. Chem. Soc. 2008, 130, 7823-7835 relates to a specific process for preparing aryl- and heteroaryl-fused [a] carbazoles. The specific synthesis process results in carbazoles which have a methyl group adjacent to the $C_3$ position of the indole skeleton. According to J. Am. Chem. Soc. 2008, 130, 7823-7835, it is also possible to use aryl- and heteroaryl-annulated carbazoles (AHACs) in OLEDs, in addition to numerous applications due to their biological and pharmacological activity. The examples in Table 3 in J. Am. Chem. Soc. 2008, 130, 7823-7835 mention exclusively carbazole derivatives substituted by a methyl group.

Eur. J. Org. Chem. 2009, 531-546 mentions a process for preparing fused carbazole derivatives. All fused carbazole derivatives mentioned have an —SO₂—Ph group on the nitrogen atom, which makes these compounds unsuitable for use in OLEDs.

WO 2009/6807 A1 relates to OLEDs having a polycyclic compound having a π-conjugated heteroacene skeleton which is joined via a carbon atom, a nitrogen atom, an oxygen atom or a sulfur atom. The broad general formula in WO 2009/6807 A1 covers carbazole derivatives among other compounds, and individual carbazole derivatives are mentioned by way of example in WO 2009/6807 A1. Almost all of the carbazole derivatives mentioned by way of example have, as substituents on the nitrogen atom, a dibenzofuranyl radical or a benzimidazolyl radical.

WO 2009/68062 A1 relates to polycyclic compounds, and the polycyclic compounds mentioned include carbazole derivatives. These polycyclic compounds can be used in OLEDs to obtain OLEDs which have a high luminescence efficiency, no pixel defects and a long lifetime. The numerous carbazolyl compounds mentioned by way of example in WO 2009/68062 A1 either have a carbazolyl radical or a derivative thereof on the base skeleton or are substituted by at least one dibenzofuranyl radical on the nitrogen.

WO 2009/6808 relates to polycyclic compounds which have a π-conjugated heteroacene structure joined by a carbon atom, nitrogen atom or oxygen atom. The polycyclic compound is used in an OLED to obtain an OLED with high luminescence efficiency and long lifetime. As in WO 2009/6807 A1, almost all of the carbazolyl compounds mentioned by way of example in WO 2009/6808 A1 have a dibenzofuranyl or benzimidazolyl radical on the nitrogen atom.

It is an object of the present application, with respect to the prior art, to provide novel device compositions for applications in organic electronics such as OLEDs, organic solar cells and switching elements, especially for OLEDs, which comprise novel materials for improvement of the performance of OLEDs, organic solar cells and switching elements, especially of OLEDs. The materials suitable for the novel device compositions should have good availability and—in the case of OLEDs—result in good efficiencies and good lifetimes in OLEDs, in combination with the emitters used in the OLEDs. More particularly, it is an object of the present application to provide materials which result in long lifetimes in OLEDs, organic solar cells and switching elements, especially in OLEDs. In addition, OLEDs with good efficiency and color purity are to be provided.

This object is achieved by the provision of an organic light-emitting diode (OLED), an organic solar cell or a switching element, preferably an organic light-emitting diode (OLED), comprising at least one substituted carbazole derivative of the general formula (I), (II) or (III)

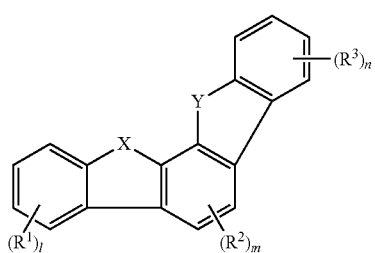

(I)

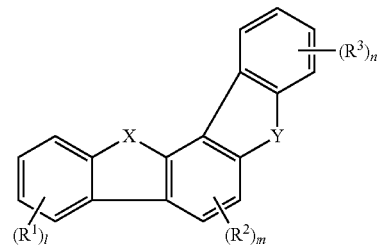

(II)

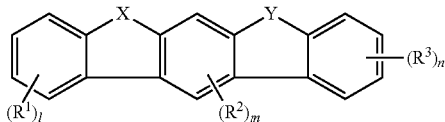

(III)

in which

X is NR⁴, O, S or PR⁴, preferably NR⁴, O or S, more preferably NR⁴ or O;

Y is NR⁵, O, S or PR⁵, preferably NR⁵, O or S, more preferably NR⁵ or O;

where at least one of the symbols X and Y is NR⁴ or NR⁵;

R¹ and R³ are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, SiR⁶R⁷R⁸, halogen radicals, halogenated $C_1$-$C_{20}$-alkyl radicals, carbonyl (—CO(R⁶)), carbonylthio (—C=O(SR⁶)), carbonyloxy (—C=O (OR⁶)), oxycarbonyl (—OC=(R⁶)), thiocarbonyl (—SC=O(R⁶)), amino (—NR⁶R⁷), OH, pseudohalogen radicals, amido (—C=(NR⁶)), —NR⁶C=O(R⁷), phosphonate (—P(O)(OR⁶)₂), phosphate (—OP(O)(OR⁶)₂), phosphine (—PR⁶R⁷), phosphine oxide (—P(O)R⁶₂), sulfate (—OS(O)₂ OR⁶), sulfoxide (—S(O)R⁶), sulfonate (—S(O)₂ OR⁶), sulfonyl (—S(O)₂R⁶), sulfonamide (—S(O)₂NR⁶R⁷), NO₂, boronic esters (—OB (OR⁶)₂), imino (—C=NR⁶R⁷), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R¹ radicals or two adjacent R³ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the R¹ or R³ radicals, in the case when it is arranged in the para position to X or Y, is bonded via a heteroatom selected from Si, Ge, O, S or P or via an sp³-hybridized carbon atom;

R² is substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, SiR⁶R⁷R⁸, halogen radicals, halogenated $C_1$-$C_{20}$-alkyl radicals, carbonyl (—CO($R^6$)), carbonylthio (—C=O(S$R^6$)), carbonyloxy (—C=O(O$R^6$)), oxycarbonyl (—OC=O($R^6$)), thiocarbonyl (—SC=O($R^6$)), amino (—N$R^6R^7$), OH, pseudohalogen radicals, amido (—C=O(N$R^6$)), —N$R^6$C=O($R^7$), phosphonate (—P(O)(O$R^6$)$_2$), phosphate (—OP(O)(O$R^6$)$_2$), phosphine (—P$R^6R^7$), phosphine oxide (—P(O)$R^6_2$), sulfate (—OS(O)$_2$O$R^6$), sulfoxide (—S(O)$R^6$), sulfonate (—S(O)$_2$O$R^6$), sulfonyl (—S(O)$_2R^6$), sulfonamide (—S(O)$_2$N$R^6R^7$), NO$_2$, boronic esters (—OB(O$R^6$)$_2$), imino (—C=N$R^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^2$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

l, n are each independently 0, 1, 2, 3 or 4, where at least l or n is 1, 2, 3 or 4;

m is 0, 1 or 2;

$R^4$, $R^5$
are each independently substituted or unsubstituted $C_6$-$C_{30}$-aryl or substituted or unsubstituted $C_1$-$C_{20}$-alkyl;

$R^6$, $R^7$, $R^8$
are each independently substituted or unsubstituted $C_1$-$C_{20}$-alkyl or substituted or unsubstituted $C_6$-$C_{30}$-aryl, substituted or unsubstituted heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy, $C_6$-$C_{30}$-aryloxy or halogenated $C_1$-$C_{20}$-alkyl radicals;

or two adjacent $R^6$ and $R^7$, $R^6$ and $R^8$ or $R^7$ and $R^8$ radicals, together with the atom to which they are bonded, form a ring having a total of 3 to 12 atoms, where the ring may be saturated or mono- or polyunsaturated and, as well as the atom to which the $R^6$, $R^7$ or $R^8$ radicals are bonded, may have exclusively carbon atoms or one or more further heteroatoms selected from N, O and P, where the ring may be unsubstituted or mono- or polysubstituted and/or may be fused to further 3- to 12-membered rings.

By virtue of the use of the carbazole derivatives substituted by at least one $R^1$ or $R^3$ substituent, where the $R^1$ or $R^3$ radicals, in the case when they are arranged in the para position to X or Y, are selected from specific radicals which are bonded via a heteroatom selected from Si, Ge, O, S or P or via an sp$^3$-hybridized carbon atom, OLEDs, organic solar cells and switching elements, preferably OLEDs, with a long lifetime are obtained. In addition, in OLEDs having the carbazole derivatives used in accordance with the invention, problematic aggregation and exciplex formation, which result in loss of efficiency and color purity, are avoided. It is thus possible in accordance with the invention to provide highly effective and pure-color OLEDs with long lifetime or organic solar cells and switching elements with long lifetime.

It has been found that the carbazole derivatives of the formulae (I), (II) and (III) are particularly suitable for use in applications in which charge carrier performance is required, especially for use in organic electronics applications, for example selected from switching elements such as organic transistors, e.g. organic FETs (field-effect transistors) and organic TFTs (thin-film transistors), organic solar cells and organic light-emitting diodes (OLEDs), the carbazole derivatives of the formula (I), (II) or (III) in OLEDs being particularly suitable for use as matrix material in a light-emitting layer and/or as hole and/or exciton blocker material and/or as electron and/or exciton blocker material, especially in combination with a phosphorescence emitter. In the case of use of the carbazole derivatives of the formula (I), (II) or (III) in OLEDs, OLEDs are obtained which have good efficiencies and a long lifetime, and which can be operated especially at a low use and operating voltage. In addition, the OLEDs have a high color purity. The carbazole derivatives of the formulae (I), (II) and (III) are especially suitable for use as matrix and/or hole/exciton blocker materials for blue and green emitters, for example light blue or deep blue emitters, these being especially phosphorescence emitters. In addition, the carbazole derivatives of the formulae (I), (II) and (III) can be used as conductor/complementary materials in organic electronics applications selected from switching elements and organic solar cells.

The carbazole derivatives of the general formulae (I), (II) and (III) used in accordance with the invention can preferably be used as matrix materials in the light-emitting layer E of an OLED, as a hole/exciton blocker, as an electron/exciton blocker, as hole injection materials, as electron injection materials, as a hole conductor and/or as an electron conductor. Corresponding layers of OLEDs are known to those skilled in the art and are specified, for example, in WO 2005/113704 or WO 2005/019373. Preference is given to using the carbazole derivatives used in accordance with the invention as matrix materials or hole and exciton blockers. The indolocarbazoles covered by the carbazole derivatives of the general formulae (I), (II) and (III) can additionally also preferably be used as hole conductors and electron/exciton blockers.

Substituted or unsubstituted $C_1$-$C_{20}$-alkyl is understood to mean alkyl radicals having from 1 to 20 carbon atoms. Preference is given to $C_1$- to $C_{10}$-alkyl radicals, particular preference to $C_1$- to $C_6$-alkyl radicals. The alkyl radicals may be either straight-chain or branched or cyclic, where the alkyl radicals in the case of cyclic alkyl radicals have at least 3 carbon atoms. In addition, the alkyl radicals may be substituted by one or more substituents selected from the group consisting of $C_1$-$C_{20}$-alkoxy, halogen, preferably F, and $C_6$-$C_{30}$-aryl which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also derivatives of the alkyl groups mentioned substituted by $C_6$-$C_{30}$-aryl, $C_1$-$C_{20}$-alkoxy and/or halogen, especially F, for example $CF_3$. This includes both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, tert-butyl and $CF_3$.

Examples of suitable cyclic alkyl groups, which may likewise be unsubstituted or substituted by the above radicals specified for the alkyl groups, are cyclopropyl, cyclobutyl, cyclopentyl, cyclohexyl, cycloheptyl, cyclooctyl, cyclononyl and cyclodecyl. These may optionally also be polycyclic ring systems, such as fluorenyl, decalinyl, norbornyl, bornanyl or adamantyl.

Suitable $C_1$-$C_{20}$-alkoxy and $C_1$-$C_{20}$-alkylthio groups derive correspondingly from the aforementioned $C_1$-$C_{20}$-alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. $C_3H_7$, $C_4H_9$ and $C_8H_{17}$ include both the n-isomers and branched isomers such as iso-propyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

Suitable pseudohalogen radicals in the context of the present application are CN, SCN, OCN, $N_3$ and SeCN, preference being given to CN and SCN. Very particular preference is given to CN.

In the present invention, $C_6$-$C_{30}$-aryl refers to radicals which are derived from monocyclic, bicyclic or tricyclic aromatics which do not comprise any ring heteroatoms. When the system is not a monocyclic system, the saturated form (perhydro form) or the partly unsaturated form (for example the dihydro form or tetrahydro form) are also possible for the second ring in the case of the designation "aryl", provided that the particular forms are known and stable. In other words, the term "aryl" in the present invention also comprises, for example, bicyclic or tricyclic radicals in which either both or all three radicals are aromatic, and also bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl or substituents with donor or acceptor action, suitable substituents with donor or acceptor action being specified below. The $C_6$-$C_{30}$-aryl radicals are preferably unsubstituted or substituted by one or more $C_1$-$C_{20}$-alkoxy groups, CN, $CF_3$, F or amino groups ($NR^6R^7$, where suitable $R^6$ and $R^7$ radicals are specified above). Further preferred substitutions of the $C_6$-$C_{30}$-aryl radicals depend on the end use of the compounds of the general formulae (I), (II) and (III) and are specified below.

Suitable $C_6$-$C_{30}$-aryloxy, $C_6$-$C_{30}$-alkylthio radicals derive correspondingly from the aforementioned $C_6$-$C_{30}$-aryl radicals. Particular preference is given to phenoxy and phenylthio.

Unsubstituted or substituted heteroaryl having from 5 to 30 ring atoms is understood to mean monocyclic, bicyclic or tricyclic heteroaromatics which derive partly from the aforementioned aryl, in which at least one carbon atom in the aryl base skeleton has been replaced by a heteroatom. Preferred heteroatoms are N, O and S. The heteroaryl radicals more preferably have from 5 to 13 ring atoms. Especially preferably, the base skeleton of the heteroaryl radicals is selected from systems such as pyridine and five-membered heteroaromatics such as thiophene, pyrrole, imidazole or furan. These base skeletons may optionally be fused to one or two six-membered aromatic radicals. Suitable fused heteroaromatics are carbazolyl, benzimidazolyl, benzofuryl, dibenzofuryl or dibenzothiophenyl. The base skeleton may be substituted at one, more than one or all substitutable positions, suitable substituents being the same as have already been specified under the definition of $C_6$-$C_{30}$-aryl. However, the heteroaryl radicals are preferably unsubstituted. Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl and imidazol-2-yl, and also the corresponding benzofused radicals, especially carbazolyl, benzimidazolyl, benzofuryl, dibenzofuryl or dibenzothiophenyl.

In the context of the present application, groups with donor or acceptor action are understood to mean the following groups:

$C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—$CO(R^6)$), carbonylthio (—C=$O(SR^6)$), carbonyloxy (—C=$O(OR^6)$), oxycarbonyl (—OC=$O(R^6)$), thiocarbonyl (—SC=$O(R^6)$), amino (—$NR^6R^7$), OH, pseudohalogen radicals, amido (—C=O($NR^6$)), —$NR^6C$=$O(R^7)$, phosphonate (—$P(O)(OR^6)_2$), phosphate (—$OP(O)(OR^6)_2$), phosphine (—$PR^6R^7$), phosphine oxide (—$P(O)R^6{}_2$), sulfate (—$OS(O)_2OR^6$), sulfoxide (—$S(O)R^6$), sulfonate (—$S(O)_2OR^6$), sulfonyl (—$S(O)_2R^6$), sulfonamide (—$S(O)_2NR^6R^7$), $NO_2$, boronic esters (—OB($OR^6)_2$), imino (—C=$NR^6R^7$), borane radicals, stannane radicals, hydrazine radicals, hydrazone radicals, oxime radicals, nitroso groups, diazo groups, vinyl groups, and boronic acid groups, sulfoximines, alanes, germanes, boroximes and borazines.

Preferred substituents with donor or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^6R^7R^8$ where $R^6$, $R^7$ and $R^8$ are preferably each independently substituted or unsubstituted alkyl or substituted or unsubstituted phenyl; more preferably, at least one of the $R^6$, $R^7$ or $R^8$ radicals is substituted or unsubstituted phenyl; most preferably, at least one of the $R^6$, $R^7$ or $R^6$ radicals is substituted phenyl, where suitable substituents have been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —$C(O)OC_1$-$C_4$-alkyl, preferably —C(O)OMe, $P(O)R_2$, preferably $P(O)Ph_2$ or $SO_2R_2$, preferably $SO_2Ph$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^6R^7R^8$, diphenylamino, —$C(O)OC_1$-$C_4$-alkyl, preferably —C(O)OMe, $P(O)Ph_2$, $SO_2Ph$.

The aforementioned groups with donor or acceptor action are not intended to rule out the possibility that further aforementioned radicals and groups may also have donor or acceptor action. For example, the aforementioned heteroaryl radicals are likewise groups with donor or acceptor action, and the $C_1$-$C_{20}$-alkyl radicals are groups with donor action.

The $R^6$, $R^7$ and $R^8$ radicals mentioned in the aforementioned groups with donor or acceptor action each have the definitions which have already been mentioned above and are mentioned below.

The carbazole derivatives used in accordance with the invention have the aforementioned structures (I), (II) or (III). Particular preference is given to using carbazole derivatives of the structure (I).

In the carbazole derivatives of the formulae (I), (II) and (III),

X is $NR^4$, O, S or $PR^4$, preferably $NR^4$, O or S, more preferably $NR^4$ or O;

Y is $NR^5$, O, S or $PR^5$, preferably $NR^5$, O or S, more preferably $NR^5$ or O;

where at least one of the symbols X and Y is $NR^4$ or $NR^5$.

Preferred carbazole derivatives of the formulae (I), (II) and (III) are thus indolocarbazoles in which X is $NR^4$ and Y is NR⁵, and benzofuranylcarbazoles in which one X or Y group is NR⁴ or NR⁵ and the other X or Y group is O.

The expressions "electron-donating substituents" and "electron-withdrawing substituents" used additionally in the present application are substituents with donor action (electron-donating substituents) or substituents with acceptor action (electron-withdrawing substituents). Suitable electron-donating and electron-withdrawing substituents are thus the substituents which have already been specified above for the substituents with donor or acceptor action.

The $R^1$ and $R^3$ radicals are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl, carbonylthio, carbonyloxy, oxycarbonyl, thiocarbonyl, amino, OH, pseudohalogen radicals, amido, phosphonate, phosphate, phosphine, phosphine oxide, sulfate, sulfoxide, sulfonate, sulfonyl, sulfonamide, $NO_2$, boronic esters, imino, borane radicals, stannane radicals, hydrazine radicals, hydrazone radicals, oxime radicals, nitroso groups, diazo groups, vinyl groups, sulfoximines, alanes, germanes, boroximes and borazines.

In addition, two adjacent $R^1$ radicals or two adjacent $R^3$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings.

In the case when one of the $R^1$ or $R^3$ radicals is arranged in the para position to X or Y, this radical is bonded via a heteroatom selected from Si, Ge, O, S or P or via an $sp^3$-hybridized carbon atom.

In a preferred embodiment, $R^1$ and $R^3$ are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms, $SiR^6R^7R^8$ or amino (—$NR^6R^7$). Additionally preferably, $R^1$ and $R^3$ are each independently substituted or unsubstituted $C_1$-$C_6$-alkyl, preferably methyl, ethyl, n-propyl, isopropyl, n-butyl, sec-butyl, isobutyl, tert-butyl, more preferably tert-butyl, substituted or unsubstituted fluorenyl; substituted or unsubstituted $C_6$-$C_{14}$-aryl, preferably substituted or unsubstituted phenyl, for example phenyl substituted by at least one of the (Ia), (IIa), (IIIa), (Ib), (IIb) or (IIIb) groups below; one of the (Ia), (IIa), (IIIa), (Ib), (IIb) or (IIIb) groups below; $SiR^6R^7R^8$ or amino (—$NR^6R^7$);

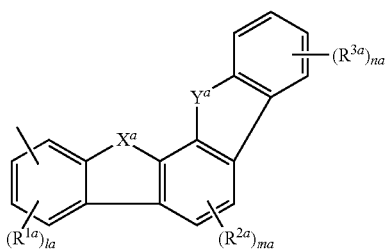

(Ia)

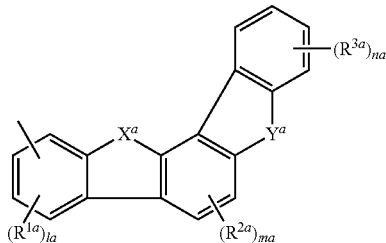

(IIa)

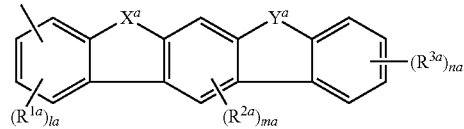

(IIIa)

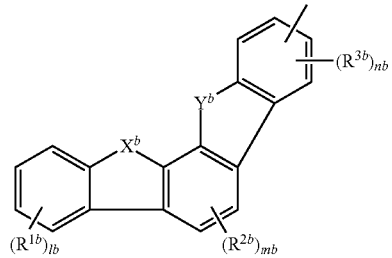

(Ib)

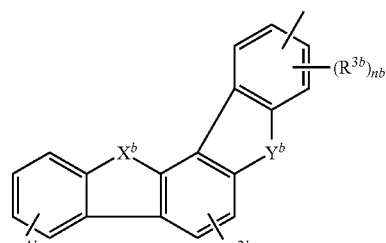

(IIb)

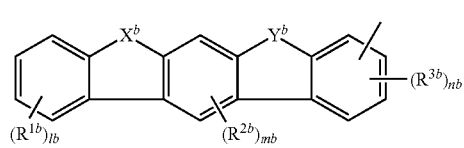

(IIIb)

The $R^6$, $R^7$ and $R^8$ radicals are each as defined below.

The radicals and indices in the (Ia), (IIa), (IIIa), (Ib), (IIb) or (IIIb) groups are each defined as follows:

$X^a$, $X^b$ are each $NR^{4a}$, $NR^{4b}$, O, S, $PR^{4a}$ or $PR^{4b}$;

$Y^a$, $Y^b$ are each $NR^{5a}$, $NR^{5b}$, O, S, $PR^{5a}$ or $PR^{5b}$;

where at least one of the symbols $X^a$, $X^b$ or $Y^a$, $Y^b$ is $NR^{4a}$, $NR^{4b}$ or $NR^{5a}$, $NR^{5b}$;

$R^{1a}$, $R^{1b}$ and $R^{3a}$, $R^{3b}$ are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—$CO(R^6)$), carbonylthio (—C=O($SR^6$)), carbonyloxy (—C=O($OR^6$)), oxycarbonyl (—OC=O($R^6$)), thiocarbonyl (—SC=O($R^6$)), amino (—$NR^6R^7$), OH, pseudohalogen radicals, amido (—C=O($NR^6$)), —$NR^6$C=O($R^7$), phosphonate (—P(O)($OR^6$)$_2$), phosphate (—OP(O)($OR^6$)$_2$), phosphine (—$PR^6R^7$), phosphine oxide (—P(O)R$^6_2$), sulfate (—OS(O)$_2$OR$^6$), sulfoxide (—S(O)R$^6$), sulfonate (—S(O)$_2$OR$^6$), sulfonyl (—S(O)$_2$R$^6$), sulfonamide (—S(O)$_2$NR$^6$R$^7$), NO$_2$, boronic esters (—OB(OR$^6$)$_2$), imino (—C=NR$^6$R$^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R$^{1a}$ or R$^{1b}$ radicals or two adjacent R$^{3a}$ or R$^{3b}$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the R$^{1a}$ or R$^{1b}$ radicals or R$^{3a}$ or R$^{3b}$ radicals, in the case when it is arranged in the para position to X or Y, is bonded via a heteroatom selected from Si, Ge, O, S or P or via an sp$^3$-hybridized carbon atom;

R$^{2a}$, R$^{2b}$ are each substituted or unsubstituted C$_1$-C$_{20}$-alkyl, substituted or unsubstituted C$_6$-C$_{30}$-aryl, substituted or unsubstituted heteroaryl having 5 to 30 ring atoms or a substituent with donor or acceptor action selected from the group consisting of C$_1$-C$_{20}$-alkoxy, C$_6$-C$_{30}$-aryloxy, C$_1$-C$_{20}$-alkylthio, C$_6$-C$_{30}$-arylthio, SiR$^6$R$^7$R$^8$, halogen radicals, halogenated C$_1$-C$_{20}$-alkyl radicals, carbonyl (—CO(R$^6$)), carbonylthio (—C=O(SR$^6$)), carbonyloxy (—C=O(OR$^6$)), oxycarbonyl (—OC=O(R$^6$)), thiocarbonyl (—SC=O(R$^6$)), amino (—NR$^6$R$^7$), OH, pseudohalogen radicals, amido (—C=O(NR$^6$)), —NR$^6$C=O(R$^7$), phosphonate (—P(O)(OR$^6$)$_2$), phosphate (—OP(O)(OR$^6$)$_2$), phosphine (—PR$^6$R$^7$), phosphine oxide (—P(O)R$^6_2$), sulfate (—OS(O)$_2$OR$^6$), sulfoxide (—S(O)R$^6$), sulfonate (—S(O)$_2$OR$^6$), sulfonyl (—S(O)$_2$R$^6$), sulfonamide (—S(O)$_2$NR$^6$R$^7$), NO$_2$, boronic esters (—OB(OR$^6$)$_2$), imino (—C=NR$^6$R$^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R$^{2a}$ or R$^{2b}$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

l$^a$, l$^b$, n$^a$, n$^b$ are each independently 0, 1, 2, 3 or 4, where at least l$^a$ or l$^b$ or n$^a$ or n$^b$ is 1, 2, 3 or 4;

m$^a$, m$^b$ are each 0, 1 or 2;

R$^{4a}$, R$^{4b}$, R$^{5a}$, R$^{5b}$ are each independently substituted or unsubstituted C$_5$-C$_{30}$-aryl or substituted or unsubstituted C$_1$-C$_{20}$-alkyl;

R$^{6a}$, R$^{6b}$, R$^{7a}$, R$^{7b}$, R$^{8a}$, R$^{8b}$ are each independently substituted or unsubstituted C$_1$-C$_{20}$-alkyl or substituted or unsubstituted C$_6$-C$_{30}$-aryl, substituted or unsubstituted heteroaryl having 5 to 30 ring atoms, —O—Si(C$_1$-C$_{20}$-alkyl)$_3$, —O—Si(C$_6$-C$_{30}$-aryl)$_3$, C$_1$-C$_{20}$-alkoxy, C$_6$-C$_{30}$-aryloxy, halogenated C$_1$-C$_{20}$-alkyl radicals, amino;

or two adjacent R$^{6a}$ or R$^{6b}$ and R$^{7a}$ or R$^{7b}$, R$^{6a}$ or R$^{6b}$ and R$^{8a}$ or R$^{8b}$ or R$^{7a}$ or R$^{7b}$ and R$^{8a}$ or R$^{8b}$ radicals, together with the atom to which they are bonded, form a ring having a total of 3 to 12 atoms, where the ring may be saturated or mono- or polyunsaturated and, as well as the atom to which the R$^{6a}$, R$^{6b}$, R$^{7a}$, R$^{7b}$, R$^{8a}$ or R$^{8b}$ radicals are bonded, may have exclusively carbon atoms or one or more further heteroatoms selected from N, O and P, where the ring may be unsubstituted or mono- or polysubstituted and/or may be fused to further 3- to 12-membered rings.

Preferred X$^a$, X$^b$, Y$^a$, Y$^b$, R$^{1a}$, R$^{1b}$, R$^{3a}$, R$^{3b}$, R$^{2a}$, R$^{2b}$, 1$^a$, 1$^b$, n$^a$, n$^b$, m$^a$, m$^b$, R$^{4a}$, R$^{4b}$, R$^{5a}$, R$^{5b}$, R$^{6a}$, R$^{6b}$, R$^{7a}$, R$^{7b}$, R$^{8a}$ and R$^{8b}$ radicals and indices each have the same definitions as the preferred X, Y, R$^1$, R$^3$, R$^2$, 1, n, m, R$^4$, R$^5$, R$^6$, R$^7$ and R$^8$ radicals and indices specified above and below.

The bonding site of the (Ia), (IIa), (IIIa), (Ib), (IIb) or (IIIb) groups, in a preferred embodiment, is in the para position to one of the X$^a$ or X$^b$ or Y$^a$ or Y$^b$ groups.

In the context of the present application, the Q group is understood hereinafter to mean one of the aforementioned (Ia), (IIa), (IIIa), (Ib), (IIb) or (IIIb) groups.

Particularly preferred R$^1$ and R$^3$ radicals are:

unsubstituted C$_1$- to C$_4$-alkyl, especially tert-butyl;

—SiR$^6$R$^7$R$^8$, especially —SiPh$_3$, —SiPh$_2$Q, —Si(CH$_3$)$_2$Q, —Si(CH$_3$)$_2$—O—Si—(CH$_3$)$_2$Q,

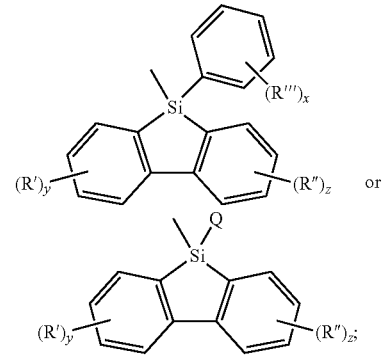

or in which:

R', R", R''' are each independently substituted or unsubstituted C$_1$-C$_{20}$-alkyl, substituted or unsubstituted C$_6$-C$_{30}$-aryl, substituted or unsubstituted heteroaryl having 5 to 30 ring atoms or a substituent with donor or acceptor action selected from the group consisting of C$_1$-C$_{20}$-alkoxy, C$_6$-C$_{30}$-aryloxy, C$_1$-C$_{20}$-alkylthio, C$_6$-C$_{30}$-arylthio, silyl, halogenated C$_1$-C$_{20}$-alkyl radicals and amino;

or two adjacent R' radicals or two adjacent R" radicals or two adjacent R''' radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

preferably each independently substituted or unsubstituted C$_1$-C$_6$-alkyl, substituted or unsubstituted $C_6$-$C_{10}$-aryl, substituted or unsubstituted heteroaryl having 5 to 13 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, silyl, halogen radicals, halogenated $C_1$-$C_{20}$-alkyl radicals and amino;

more preferably $C_1$-$C_6$-alkyl, substituted or unsubstituted $C_6$-$C_{10}$-aryl, substituted or unsubstituted heteroaryl having 5 to 13 ring atoms or a substituent with donor or acceptor action selected from the group consisting of methoxy, phenyloxy, halogenated $C_1$-$C_4$-alkyl, preferably $CF_3$, $CH_2F$, $CHF_2$, $C_2F_5$, halogen, preferably F, CN, silyl, e.g. triphenylsilyl or

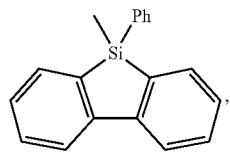 [SMILES: C[Si]1(c2ccccc2)c2ccccc2-c2ccccc21]

and diphenylamino;

x is 0, 1, 2, 3, 4 or 5; preferably 0, 1 or 2, more preferably 0;

y, z are each 0, 1, 2, 3 or 4; preferably 0, 1 or 2, more preferably 0;

Q is a group of the formula (Ia), (IIa), (IIIa), (Ib), (IIb), (IIIb), suitable groups of the formulae (Ia), (IIa), (IIIa), (Ib), (IIb), (IIIb) having been specified above.

Suitable $R^6$, $R^7$ and $R^8$ radicals correspond to the $R^6$, $R^7$ and $R^8$ radicals specified below.

$R^6$, $R^7$, $R^8$ are each independently:

substituted or unsubstituted $C_1$-$C_{20}$-alkyl or substituted or unsubstituted $C_6$-$C_{30}$-aryl, suitable and preferred alkyl and aryl radicals having been specified above. More preferably, the $R^6$, $R^7$ and $R^8$ radicals are each $C_1$-$C_6$-alkyl, e.g. methyl, ethyl or i-propyl, phenyl. In a preferred embodiment—in the case of $SiR^6R^7R^8$—$R^6$, $R^7$ and $R^8$ are preferably each independently substituted or unsubstituted $C_1$-$C_{20}$-alkyl or substituted or unsubstituted phenyl.

In addition, $R^6$, $R^7$ and $R^8$ may each be defined as follows:

Two adjacent $R^6$ and $R^7$, $R^6$ and $R^8$ or $R^7$ and $R^8$ radicals, together with the atom to which they are bonded, form a ring having a total of 3 to 12 atoms, where the ring may be saturated or mono- or polyunsaturated and, as well as the atom to which the $R^6$, $R^7$ or $R^8$ radicals are bonded, may have exclusively carbon atoms or one or more further heteroatoms selected from N, O and P, where the ring may be unsubstituted or mono- or polysubstituted and/or may be fused to further 3- to 12-membered rings.

In a preferred embodiment, two adjacent $R^8$ and $R^7$, $R^6$ and $R^8$ or $R^7$ and $R^8$ radicals, together with the atom to which they are bonded, form a ring having a total of 4 to 8 atoms, where the ring may be saturated or mono- or polyunsaturated and, as well as the atom to which the $R^6$, $R^7$ or $R^8$ radicals are bonded, has exclusively carbon atoms, where the ring may be unsubstituted or mono- or polysubstituted and/or may be fused to further 5- to 8-membered rings.

In a particularly preferred embodiment, two adjacent $R^6$ and $R^7$, $R^6$ and $R^8$ or $R^7$ and $R^8$ radicals, together with the atom to which they are bonded, form a ring having a total of 4 to 6, preferably 5, atoms, where the ring may be saturated or mono- or polyunsaturated and, as well as the atom to which the $R^6$, $R^7$ or $R^8$ radicals are bonded, has exclusively carbon atoms, where the ring may be fused to further 5- to 8-membered rings, preferably 6-membered rings.

A particularly preferred example for the case that two adjacent $R^6$ and $R^7$, $R^6$ and $R^8$ or $R^7$ and $R^8$ radicals, together with the atom to which they are bonded, form a ring having a total of 3 to 12 atoms, is—especially in the case of —$SiR^6R^7R^8$ and —$NR^6R^7$:

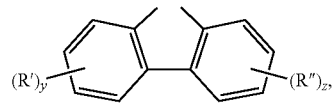

in which:

R', R"
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, silyl, halogenated $C_1$-$C_{20}$-alkyl radicals and amino;

or two adjacent R' radicals or two adjacent R" radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

preferably each independently substituted or unsubstituted $C_1$-$C_6$-alkyl, substituted or unsubstituted $C_6$-$C_{10}$-aryl, substituted or unsubstituted heteroaryl having 5 to 13 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, silyl, halogenated $C_1$-$C_{20}$-alkyl radicals and amino;

more preferably $C_1$-$C_6$-alkyl, substituted or unsubstituted $C_6$-$C_{10}$-aryl, substituted or unsubstituted heteroaryl having 5 to 13 ring atoms or a substituent with donor or acceptor action selected from the group consisting of methoxy, phenyloxy, halogenated $C_1$-$C_4$-alkyl, preferably $CF_3$, $CH_2F$, $CHF_2$, $C_2F_5$, halogen, preferably F, CN, silyl, e.g. triphenylsilyl or

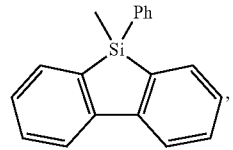 [SMILES: C[Si]1(c2ccccc2)c2ccccc2-c2ccccc21]

and diphenylamino;

y, z are each 0, 1, 2, 3 or 4; preferably 0, 1 or 2, more preferably 0.

The further radical present in the case of —$SiR^6R^7R^8$ has one of the above definitions for $R^6$, $R^7$ and $R^8$.

In the at least one substituted carbazole derivative of the general formula (I), (II) or (III), l, n and m are each defined as follows:

l, n are each independently 0, 1, 2, 3 or 4, where at least l or n is 1, 2, 3 or 4;

m is 0, 1 or 2.

In a preferred embodiment, l, n and m in the at least one substituted carbazole derivative of the general formula (I), (II) or (III) are each defined as follows:

l and n are each independently 0, 1 or 2, where at least l or n is 1 or 2;

m is 0.

In a preferred embodiment of the present invention, at least one $R^1$ or $R^3$ substituent in the at least one substituted carbazole derivative of the general formula (I), (II) or (III) is arranged in the para position to X or Y.

More preferably, the at least one substituted carbazole derivative of the general formula (I), (II) or (III) has an $R^1$ substituent or an $R^3$ substituent which is arranged in the para position to X or Y, or both an $R^1$ substituent and an $R^3$ substituent each arranged in the para position to X and Y.

In a particularly preferred embodiment, the inventive OLED thus comprises at least one carbazole derivative of the general formula

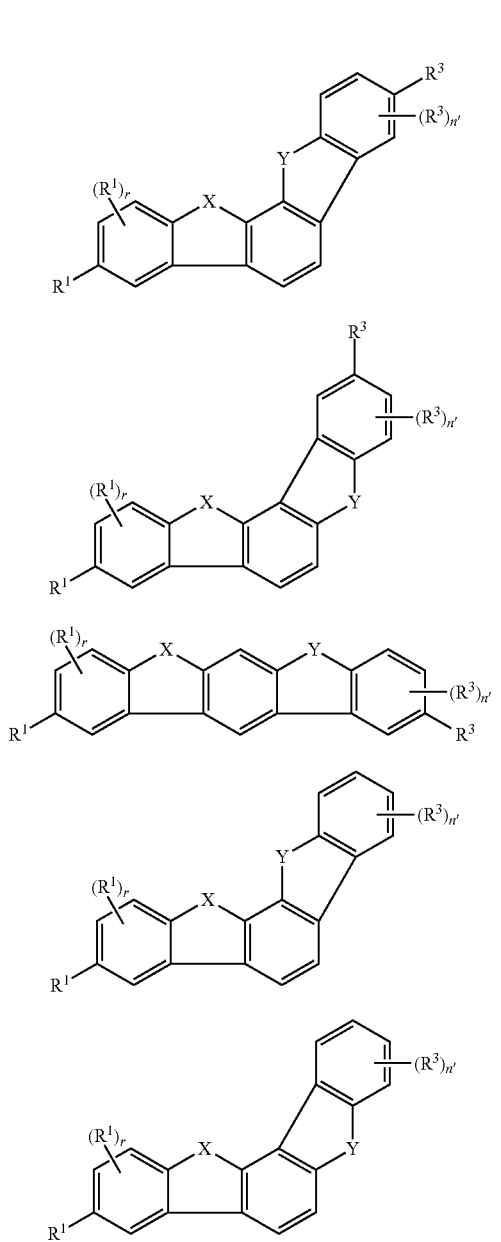

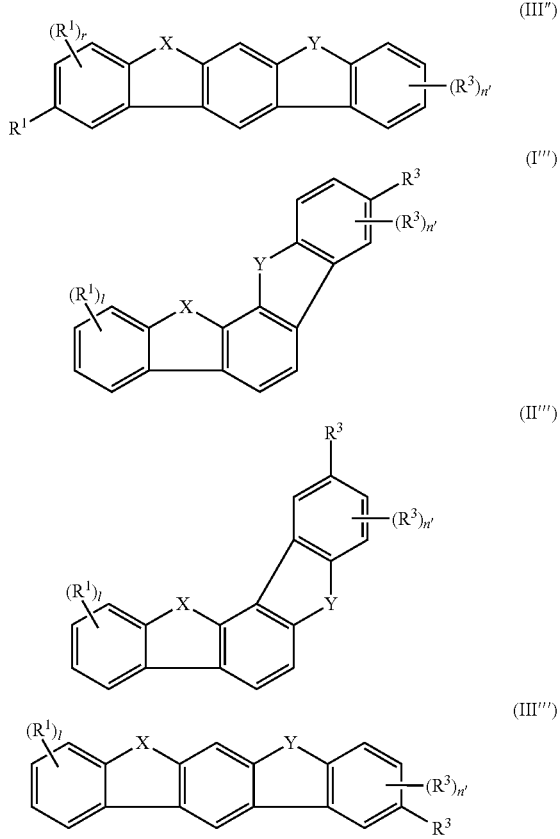

The X, Y, $R^1$, $R^3$, n and l radicals and indices in the compounds of the formulae (I'), (II'), (III'), (I"), (II"), (III"), (I'''), (II''') and (III''') are each as defined above. In a preferred embodiment, n and l are each 0. n' and l' in the compounds of the formulae (I'), (II'), (III'), (I"), (II"), (III"), (I'''), (II''') and (III''') are each independently 0, 1, 2 or 3, preferably 0 or 1, more preferably 0.

The $R^4$ and $R^5$ substituents in the at least one substituted carbazole derivative of the general formula (I), (II) or (III) are each independently substituted or unsubstituted $C_6$-$C_{30}$-aryl or substituted or unsubstituted $C_1$-$C_{20}$-alkyl.

In a preferred embodiment, the $R^4$ or $R^5$ substituents in the at least one substituted carbazole derivative of the general formula (I), (II) or (III) are each defined as follows:

$R^4$ and $R^5$
    are each independently unsubstituted phenyl, $SiR^6R^7R^8$-substituted phenyl;

$R^6$, $R^7$, $R^8$
    are each independently substituted or unsubstituted $C_1$-$C_6$-alkyl, preferably methyl, ethyl, n-propyl, isopropyl, n-butyl, sec-butyl, isobutyl, tert-butyl, more preferably methyl; substituted or unsubstituted $C_6$-$C_{14}$-aryl, preferably unsubstituted or substituted phenyl, for example phenyl substituted by at least one Q group; Q; —O—Si($C_1$-$C_6$-alkyl)$_3$, —O—Si($C_6$-$C_{30}$-aryl)$_3$; —O—Si($C_1$-$C_6$-alkyl)$_2$Q;

or two adjacent $R^6$ and $R^7$, $R^6$ and $R^8$ or $R^7$ and $R^8$ radicals, together with the atom to which they are bonded, form a ring having a total of 4 to 6, preferably 5, atoms, where the ring may be saturated or mono- or polyunsaturated and, as well as the atom to which the $R^6$, $R^7$ or $R^8$ radicals are bonded, has exclusively carbon atoms, where the ring may be fused to further 5- to 8-membered rings, preferably 6-membered rings;

Q is a group of the formula (Ia), (IIa), (IIIa), (Ib), (IIb) or (IIIb).

Preferred $R^6$, $R^7$ and $R^8$ radicals and preferred Q groups have been specified above.

In a very particularly preferred embodiment of the present invention, at least one of the $R^1$, $R^2$, $R^3$, $R^4$ or $R^5$ radicals, preferably at least one of the $R^1$ or $R^3$ radicals, of the substituted carbazole derivative of the general formula (I), (II) or (III) is an Si-comprising radical. Especially preferably, the substituted carbazole derivative of the general formula (I), (II) or (III) has one or two Si-comprising radicals, where the Si-comprising radicals are especially preferably arranged in the para position to X and/or Y. Particular preference is given to carbazole derivatives of the formula (I'), (II'), (III'), (I''), (II''), (III''), (I'''), (II''') or (III''') in which at least one $R^1$ or $R^3$ radical is an Si-comprising radical.

Suitable Si-comprising radicals are mentioned in the definitions of $R^1$, $R^2$, $R^3$, $R^4$ or $R^5$. Particularly preferred Si-comprising radicals are specified below:

—$SiPh_3$, —$SiPh_2Q$, —$Si(CH_3)_2Q$, —$Si(CH_3)_2$—O—Si$(CH_3)_2Q$,

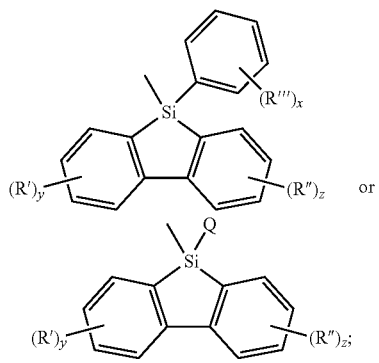

in which:
R', R'', R'''
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$ alkylthio, $C_6$-$C_{30}$-arylthio, silyl, halogenated $C_1$-$C_{20}$-alkyl radicals and amino;

or two adjacent R' radicals or two adjacent R'' radicals or two adjacent R''' radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

preferably each independently substituted or unsubstituted $C_1$-$C_6$-alkyl, substituted or unsubstituted $C_6$-$C_{10}$-aryl, substituted or unsubstituted heteroaryl having 5 to 13 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, silyl, halogenated $C_1$-$C_{20}$-alkyl radicals and amino;

more preferably $C_1$-$C_6$-alkyl, substituted or unsubstituted $C_6$-$C_{10}$-aryl, substituted or unsubstituted heteroaryl having 5 to 13 ring atoms or a substituent with donor or acceptor action selected from the group consisting of methoxy, phenyloxy, halogenated $C_1$-$C_4$-alkyl, preferably $CF_3$, $CH_2F$, $CHF_2$, $C_2F_5$, CN, silyl, e.g. triphenylsilyl or

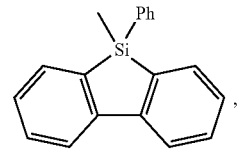

carbazole and diphenylamino;

x is 0, 1, 2, 3, 4 or 5; preferably 0, 1 or 2, more preferably 0;

y, z are each 0, 1, 2, 3 or 4; preferably 0, 1 or 2, more preferably 0;

Q is a group of the formula (Ia), (IIa), (IIIa), (Ib), (IIb) or (IIIb), suitable groups of the formula (Ia), (IIa), (IIIa), (Ib), (IIb) or (IIIb) having been specified above.

Particularly preferred Si-comprising radicals are:
—$SiPh_3$, —$SiPh_2Q$,

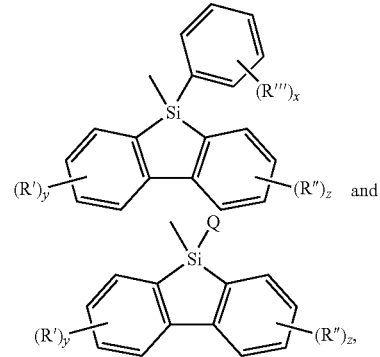

where the Q, R', R'', R''', x, y and z radicals and indices have each been defined above.

Very particularly preferred Si-comprising radicals are:
—$SiPh_3$ and

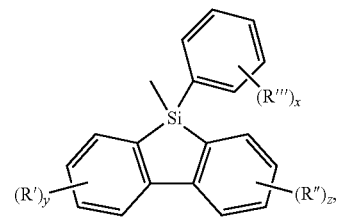

where the R', R'', R''', x, y and z radicals and indices have each been defined above.

Suitable compounds of the formulae (I), (II) and (III) are mentioned by way of example below:

Examples of suitable indolocarbazoles are:
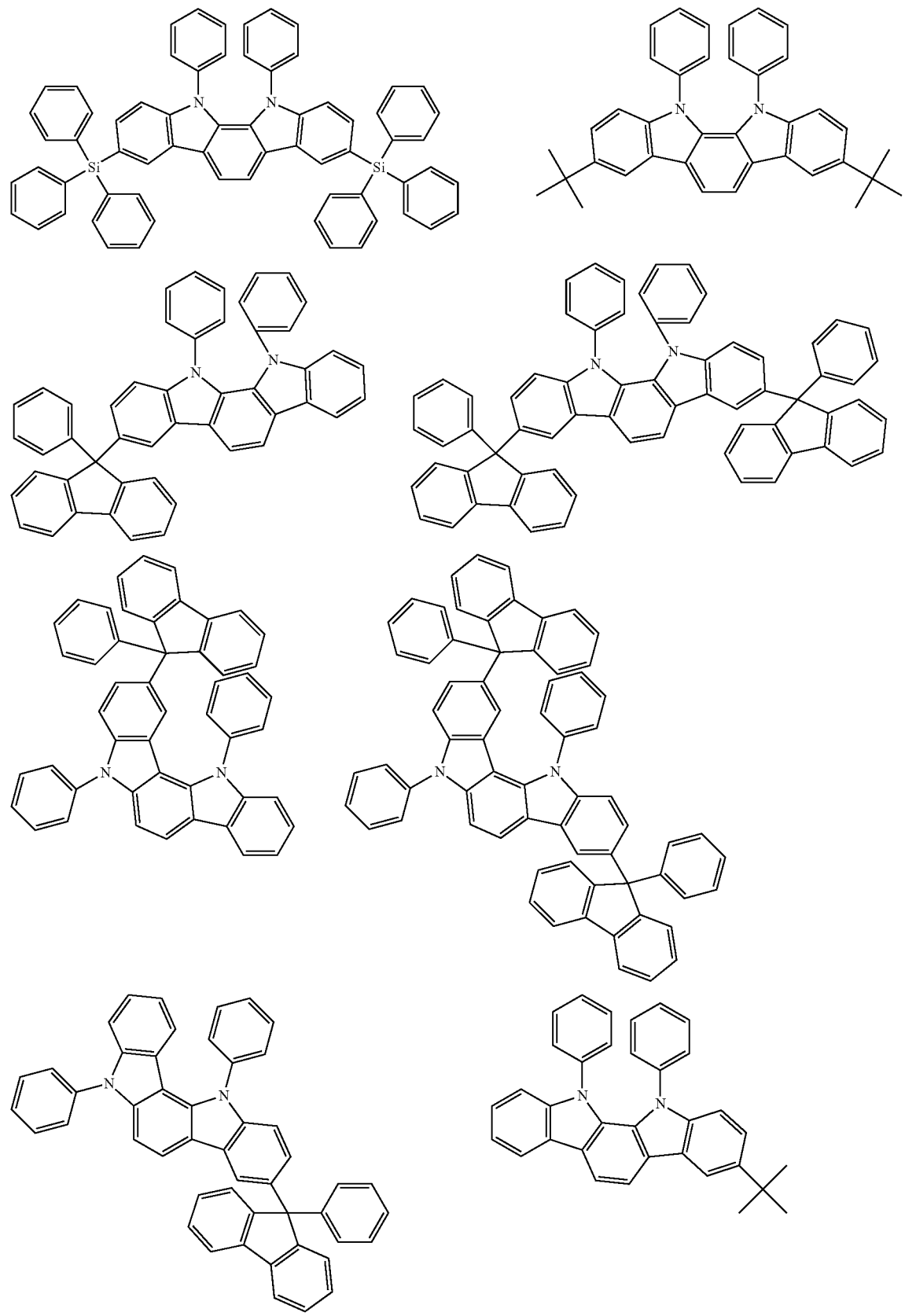

21
22
-continued
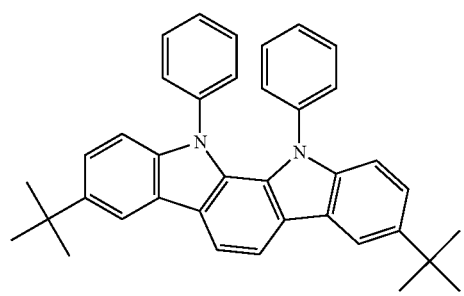
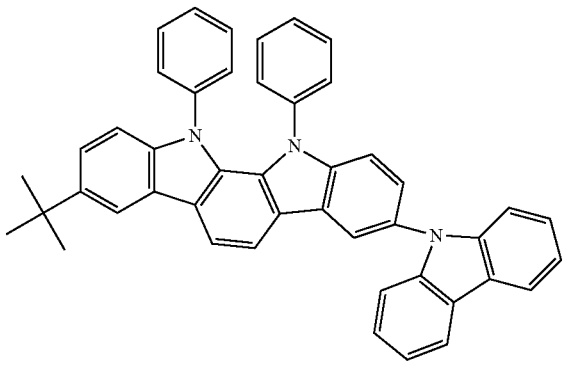
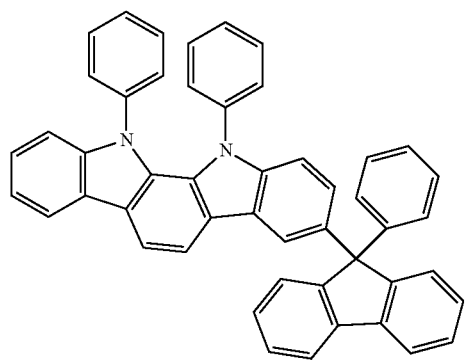
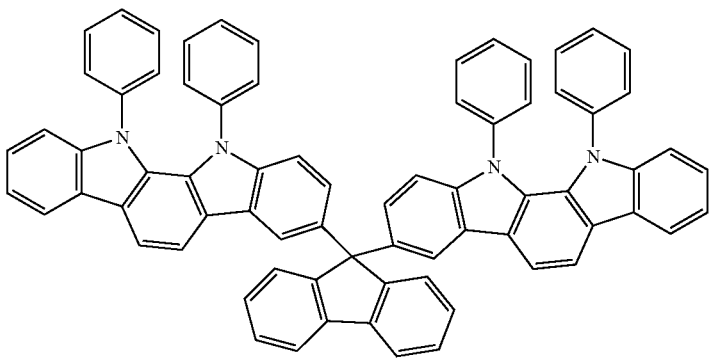
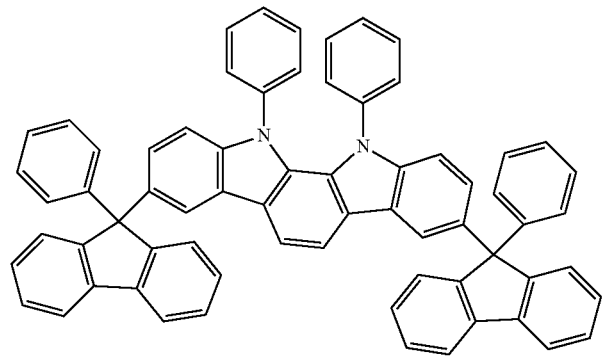
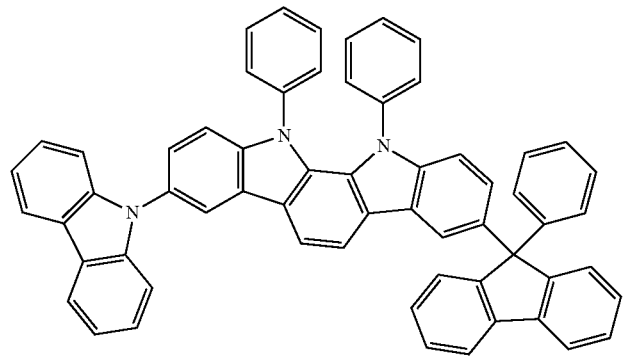

23
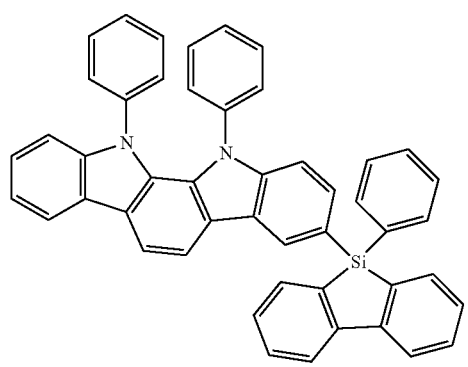
24
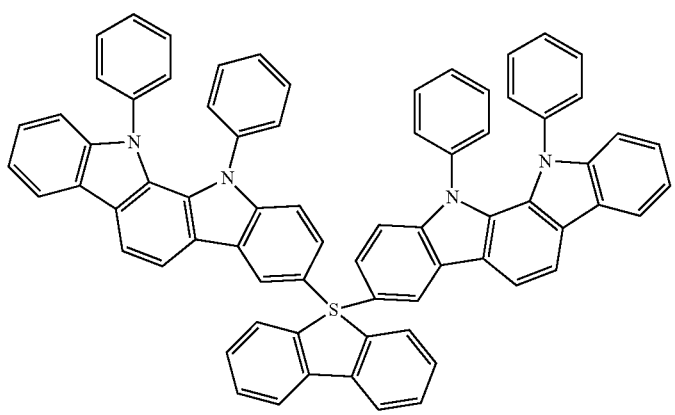
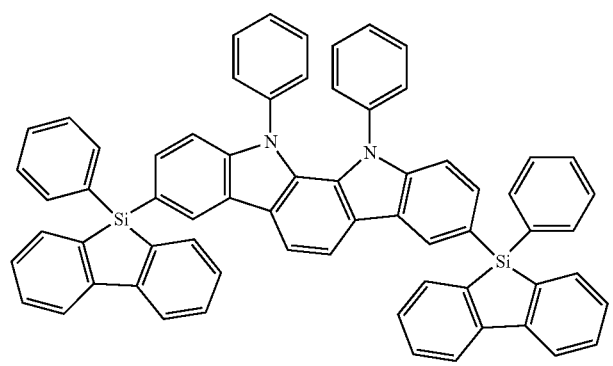
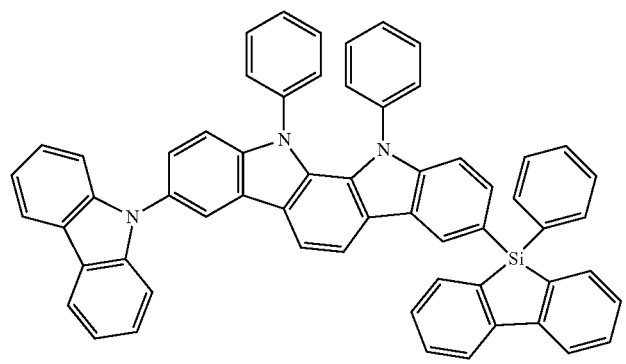
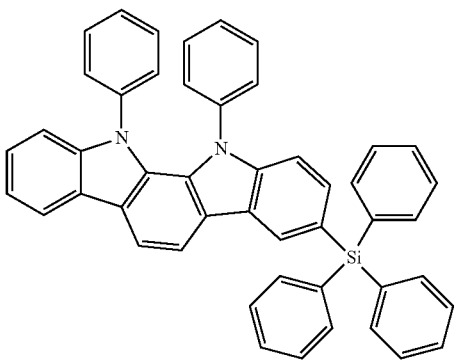
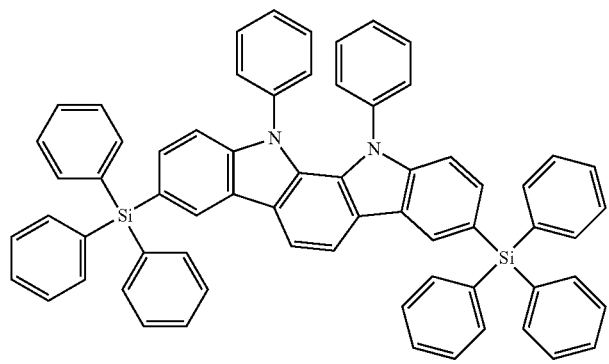

-continued
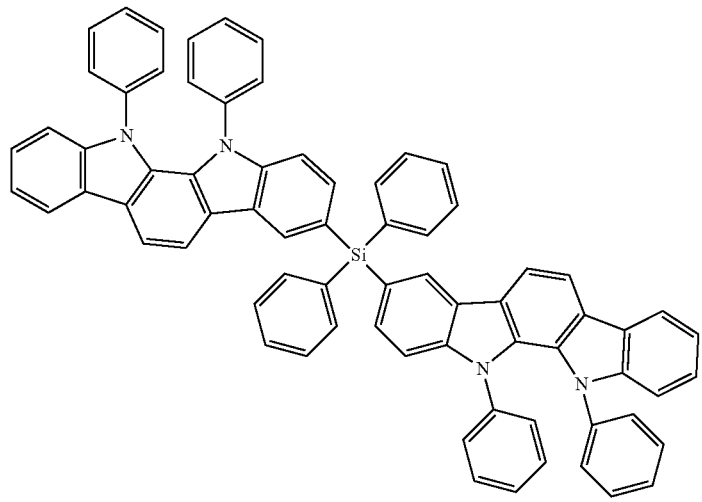
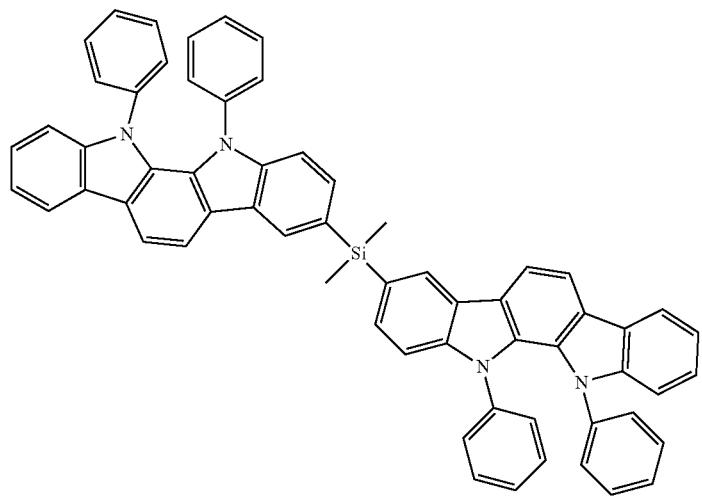
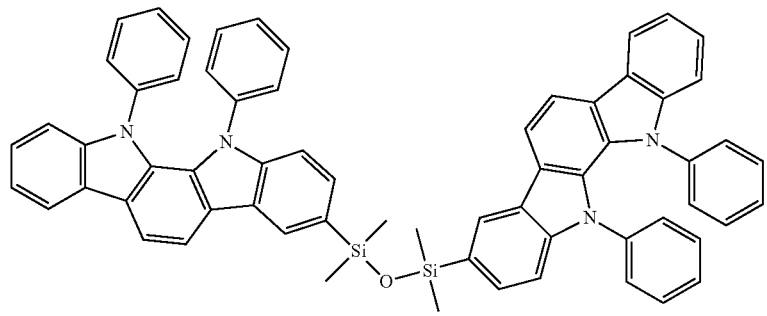
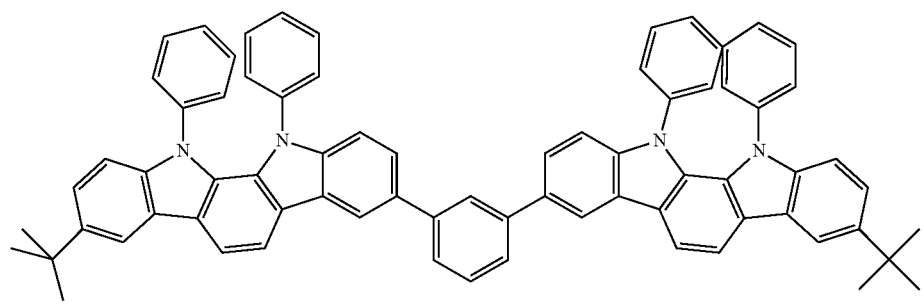

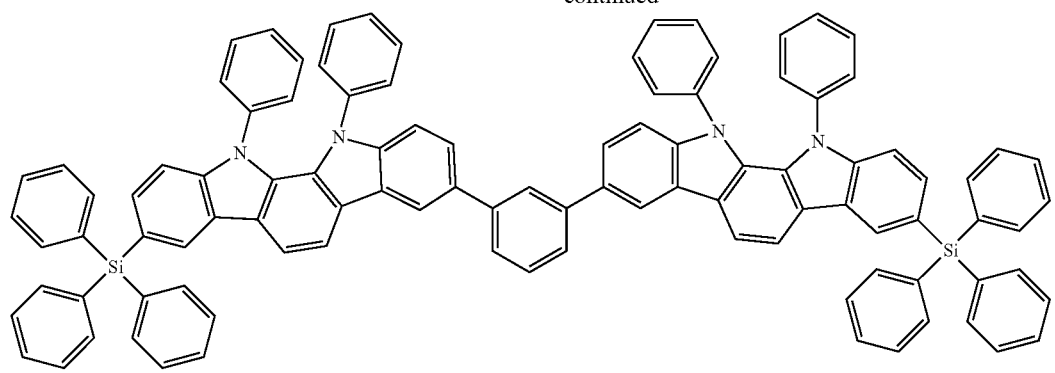
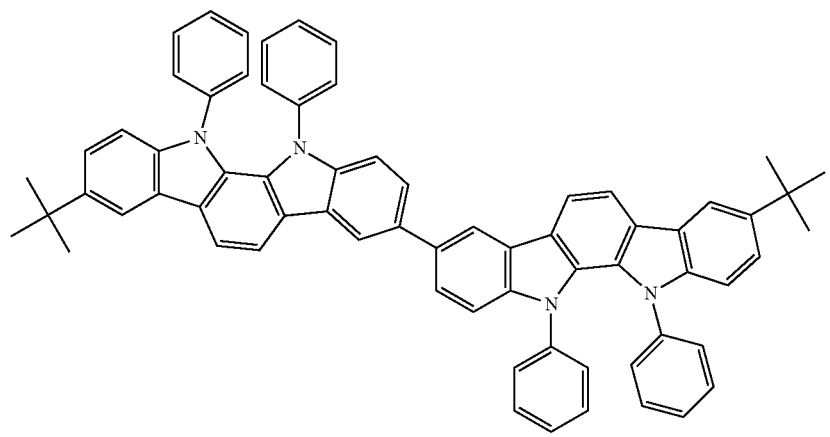
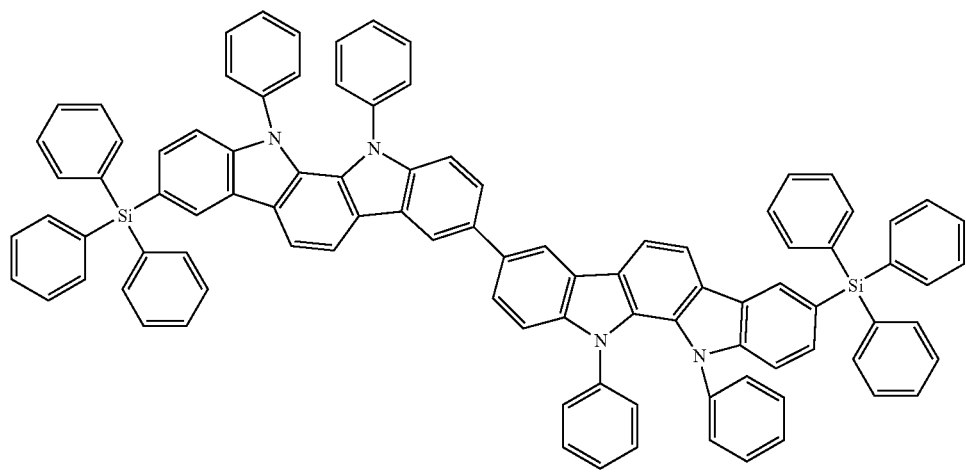
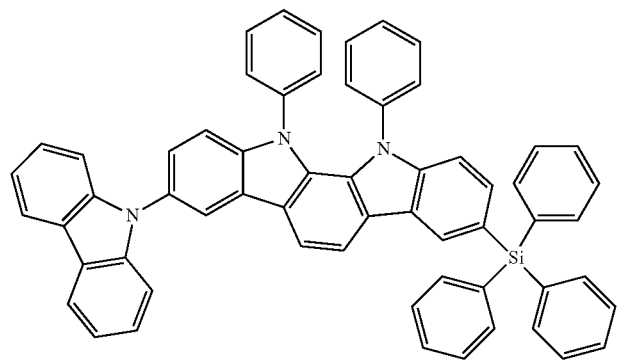

-continued
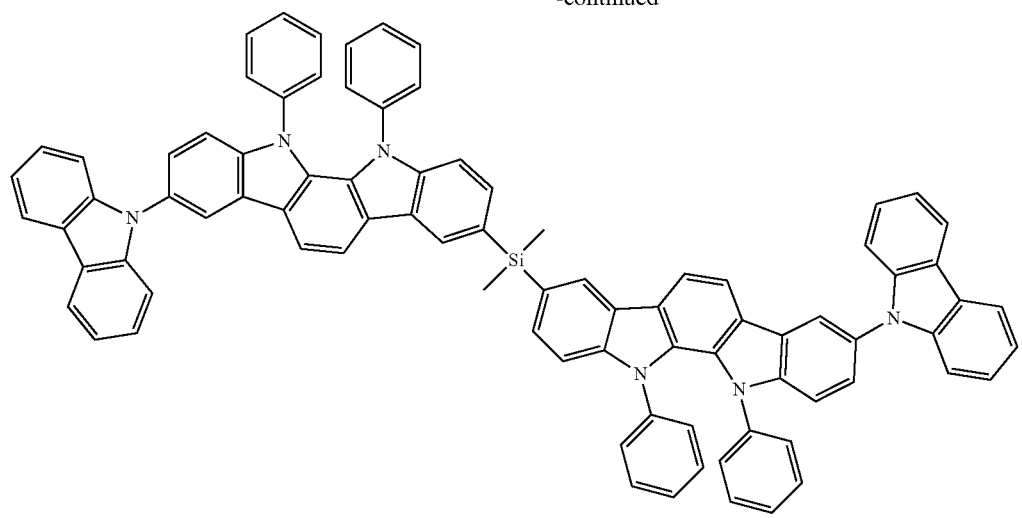
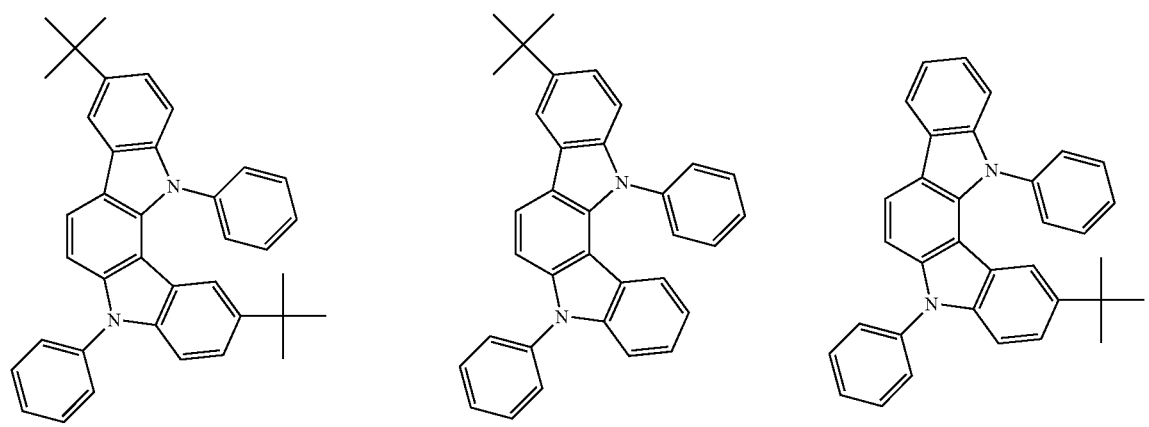
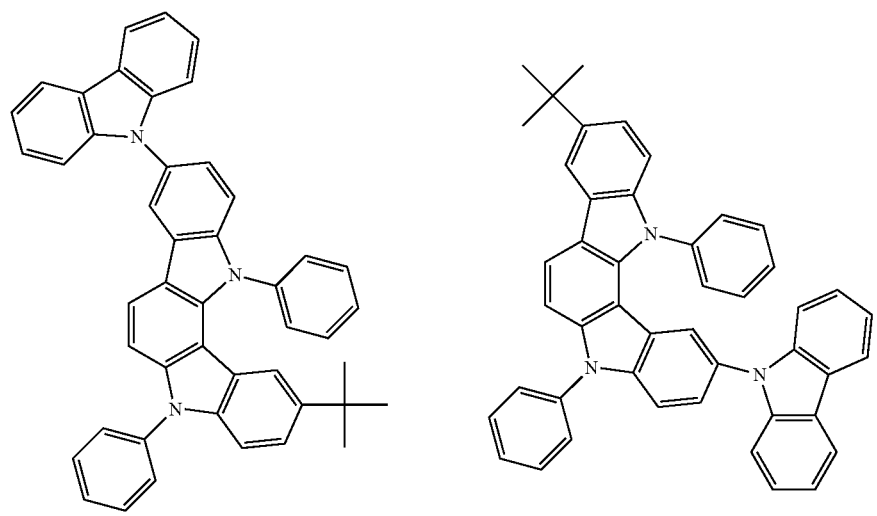

-continued
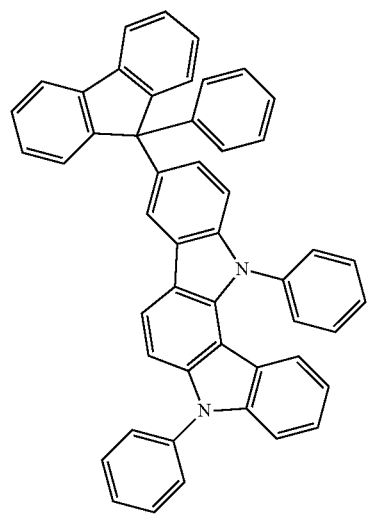
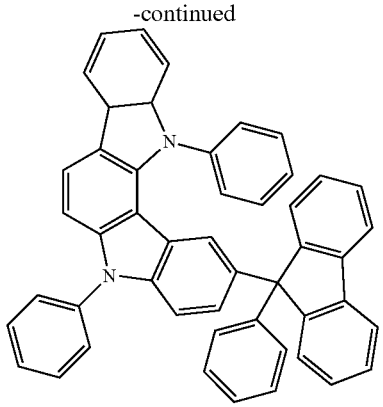
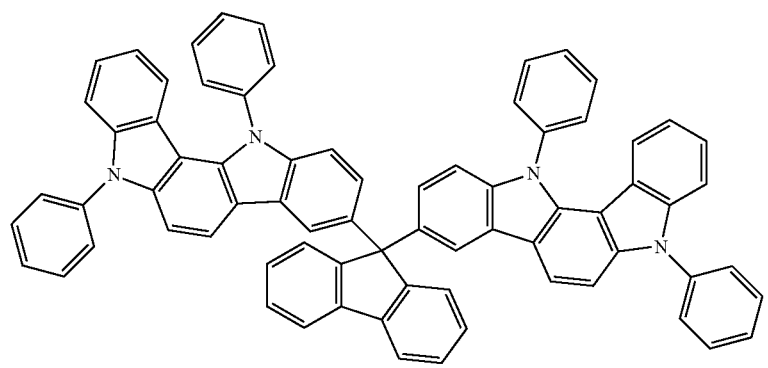
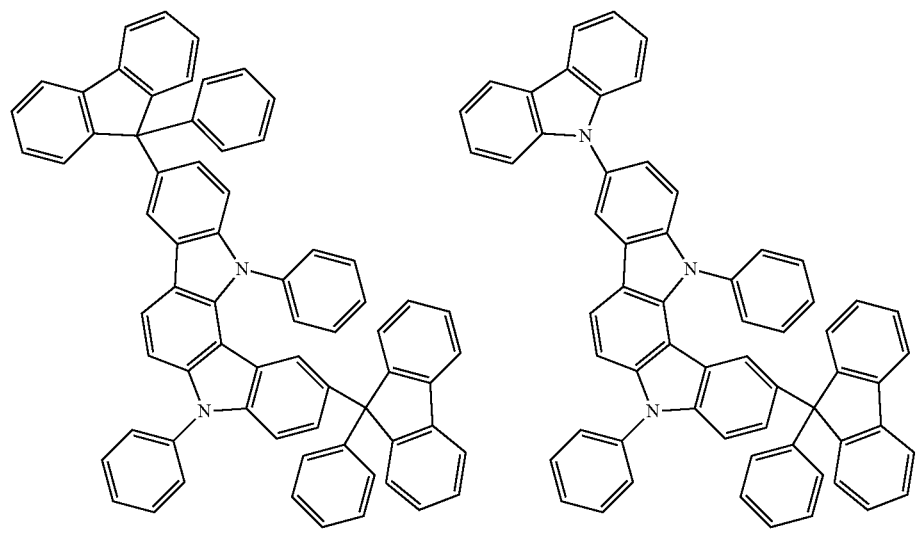

-continued
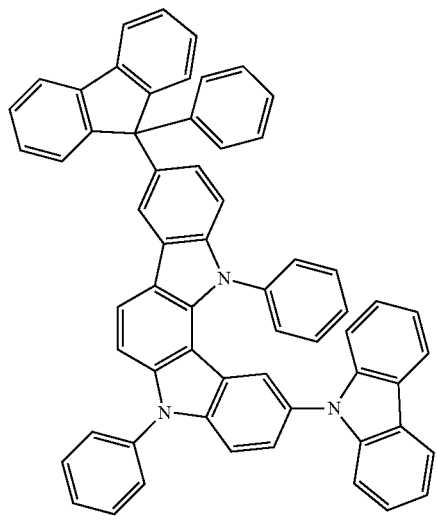
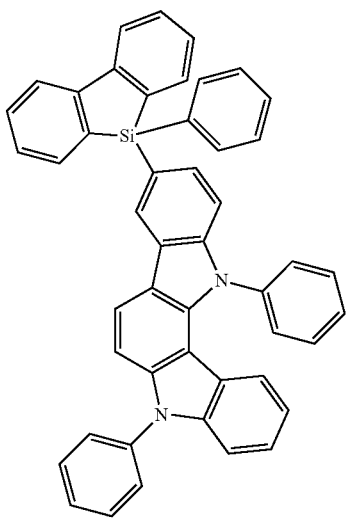
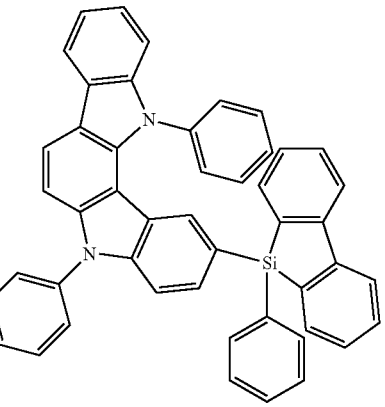
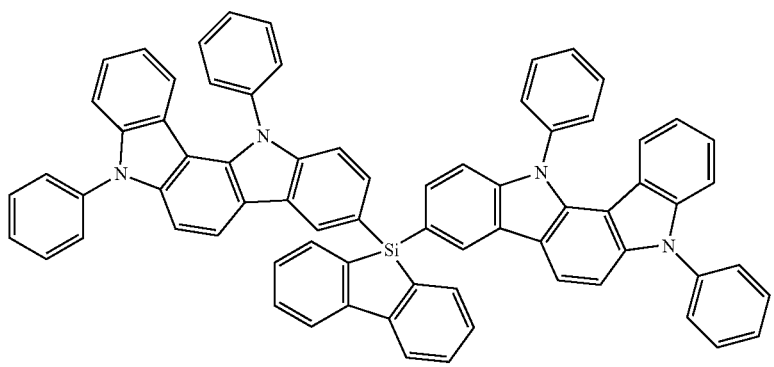
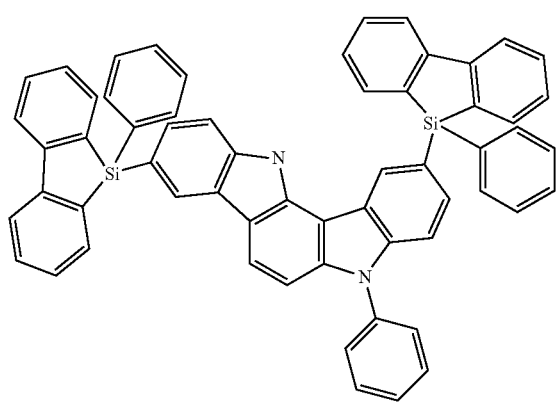
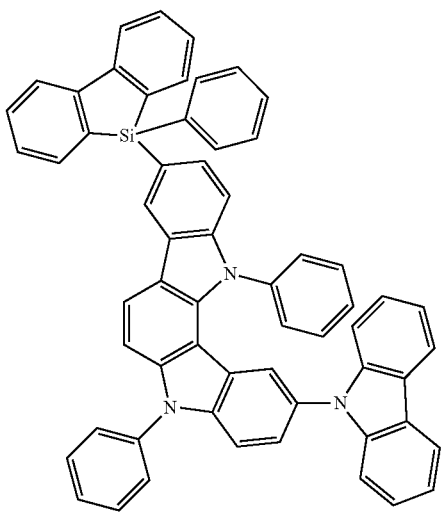

-continued
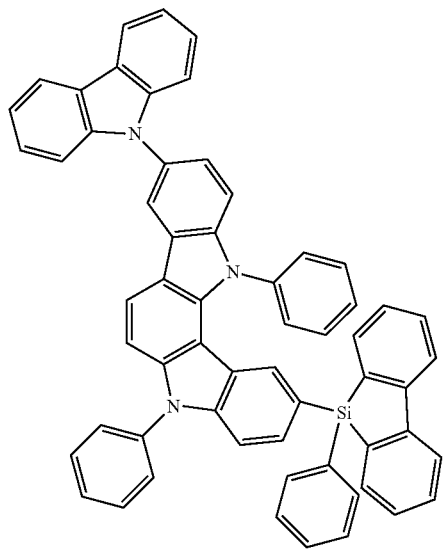
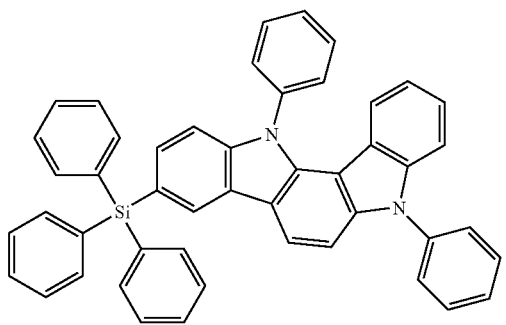
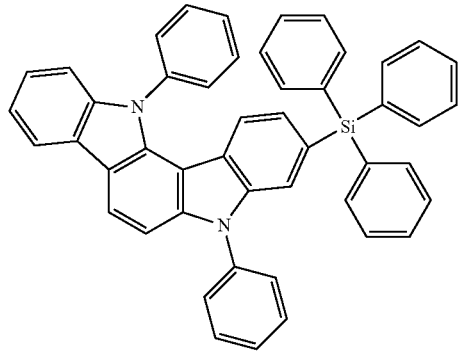
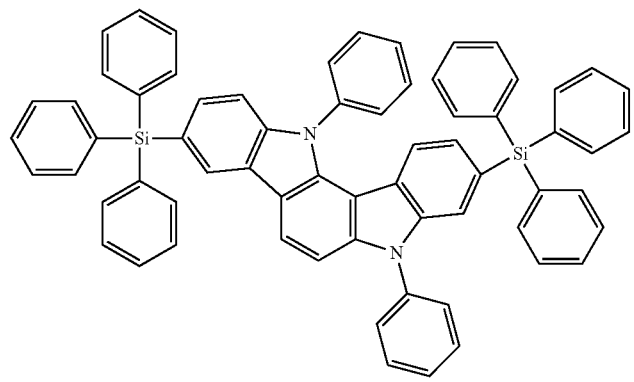
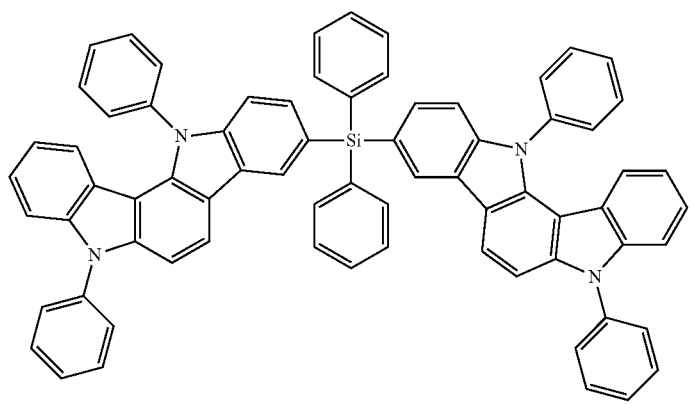
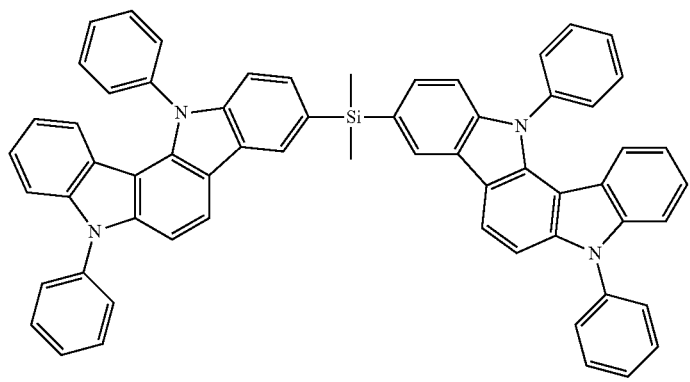

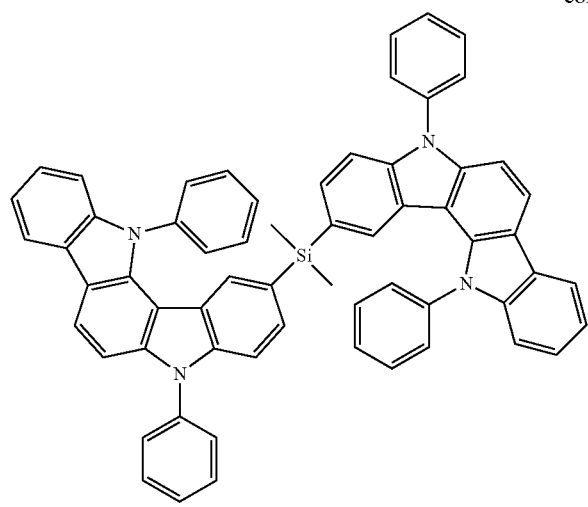
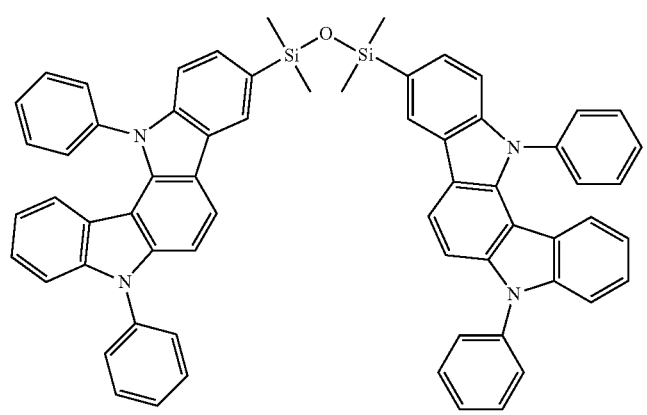
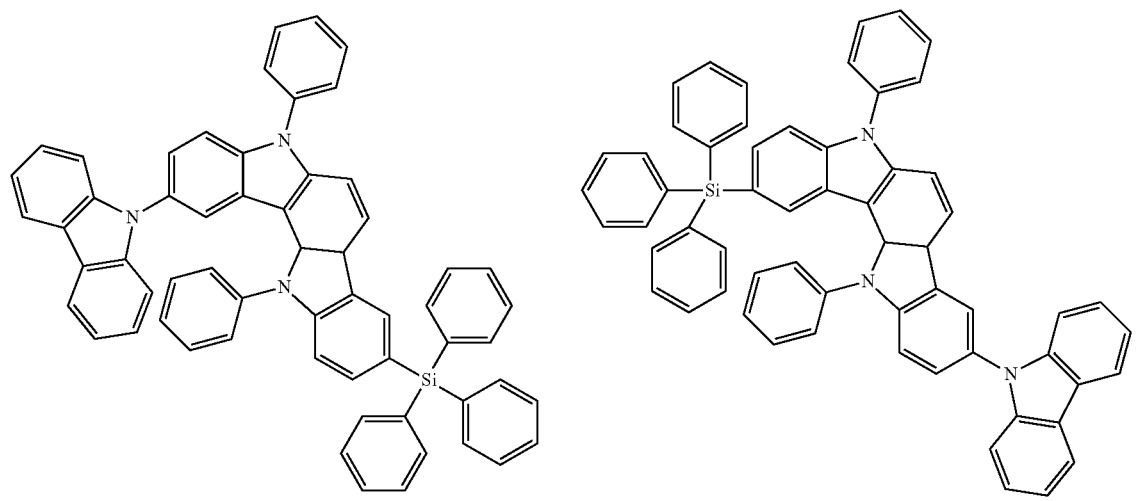

-continued
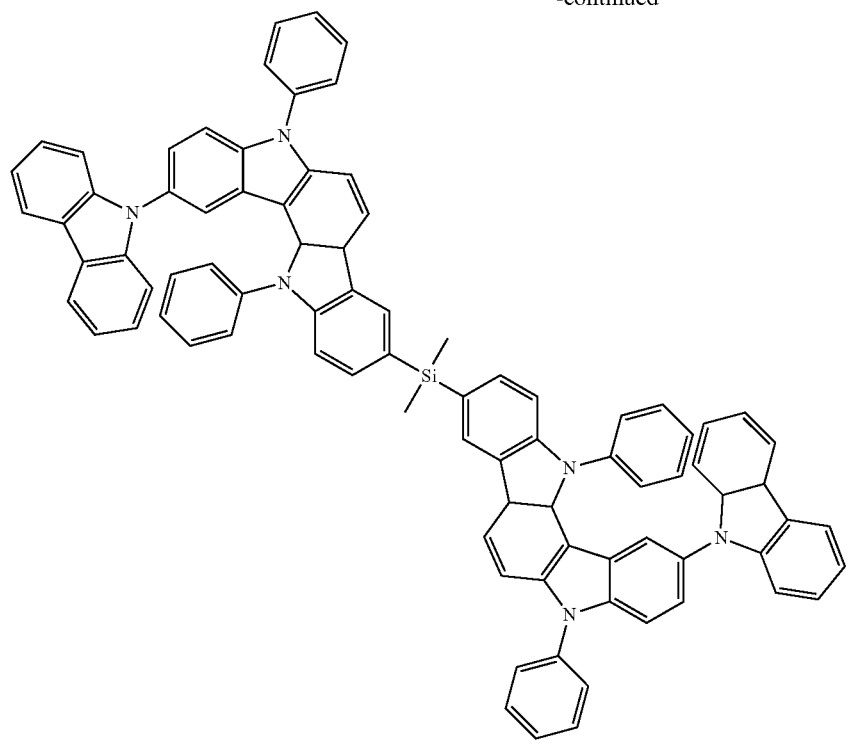
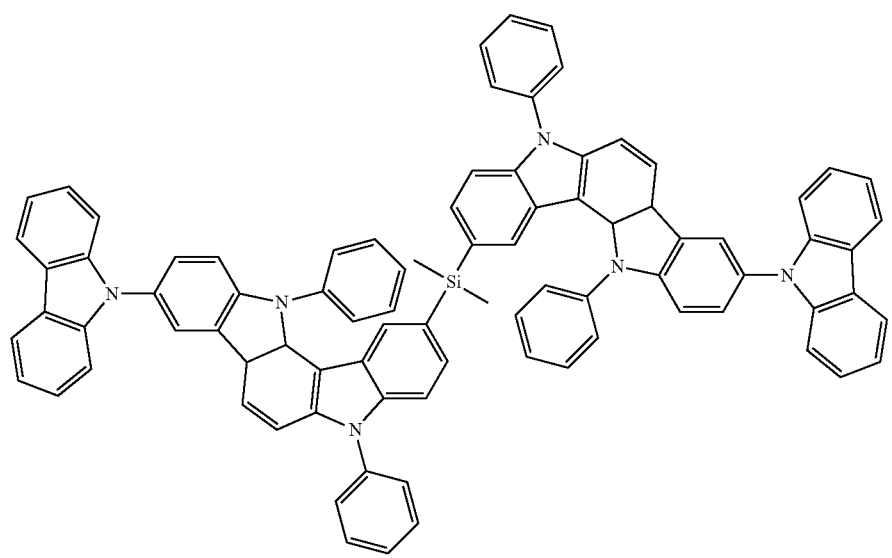

-continued
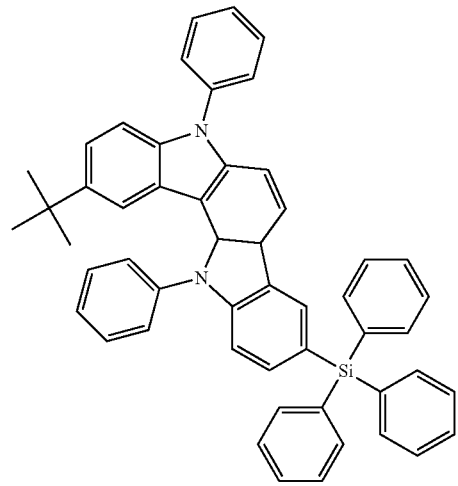
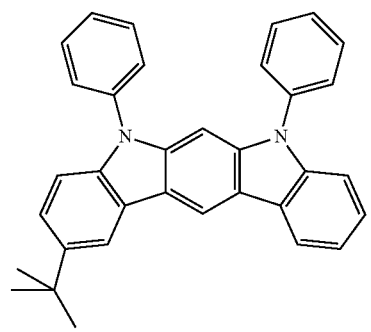
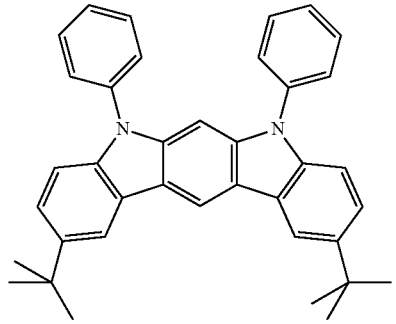
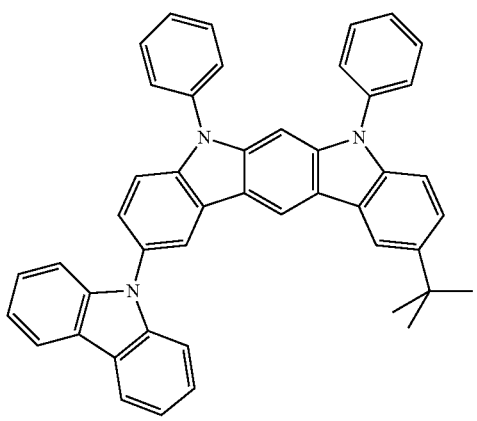
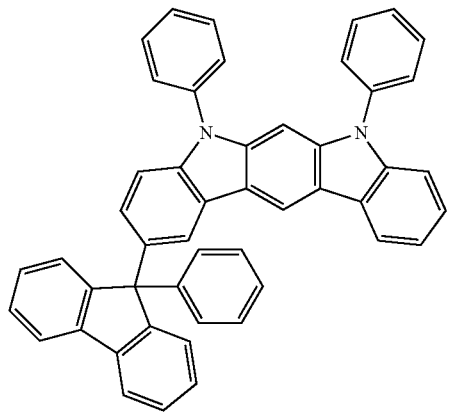
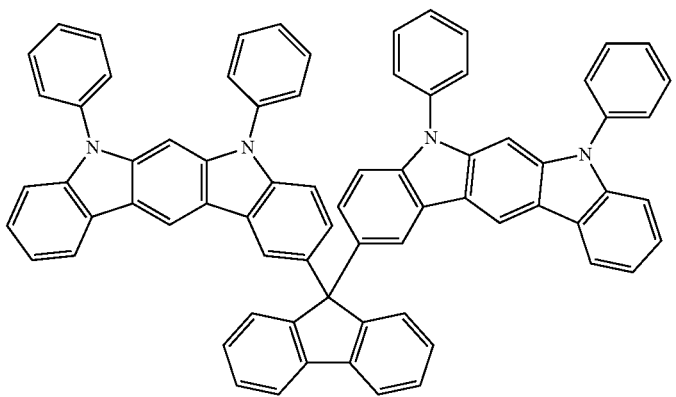
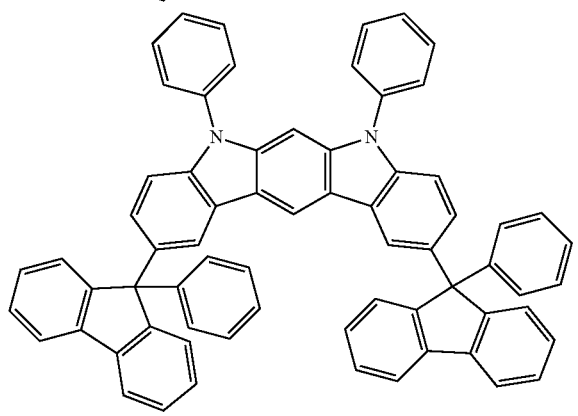
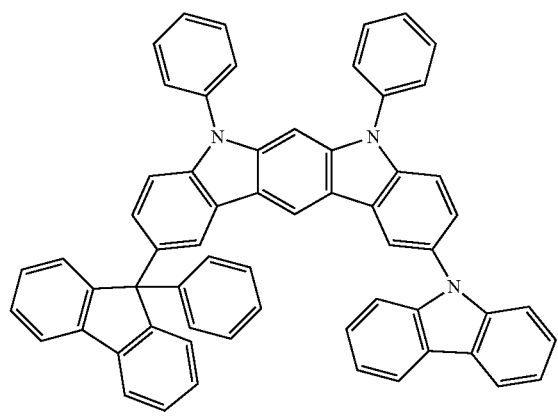

-continued
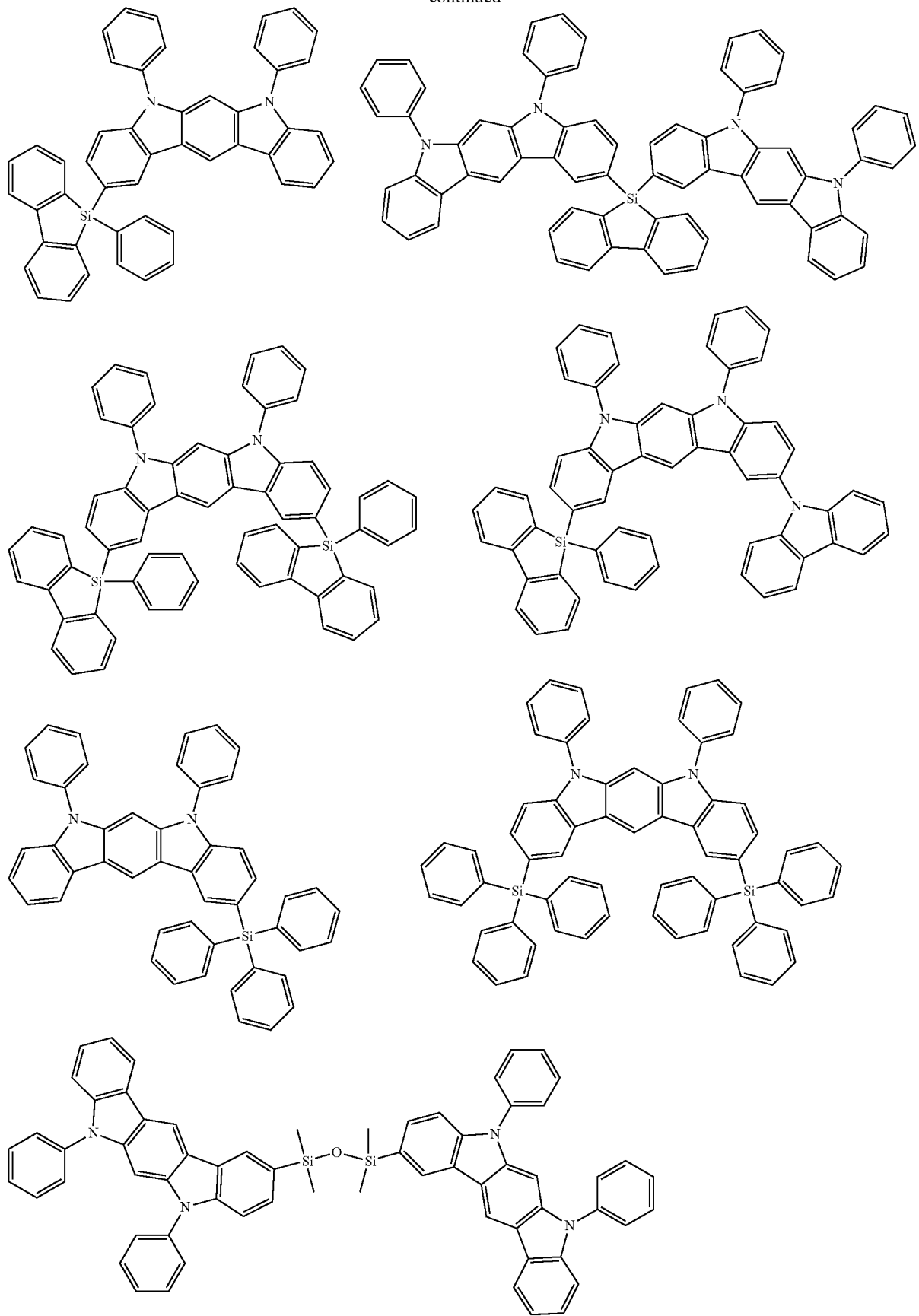

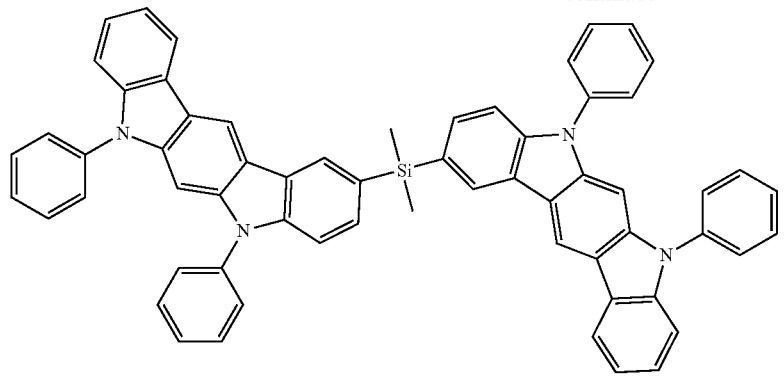
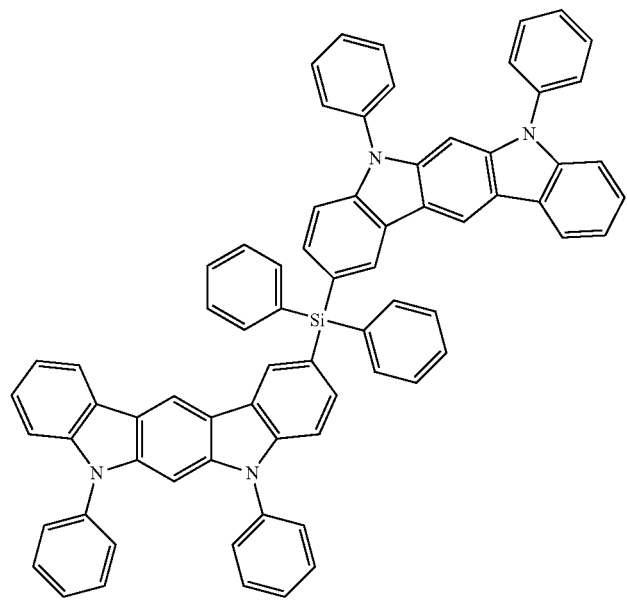
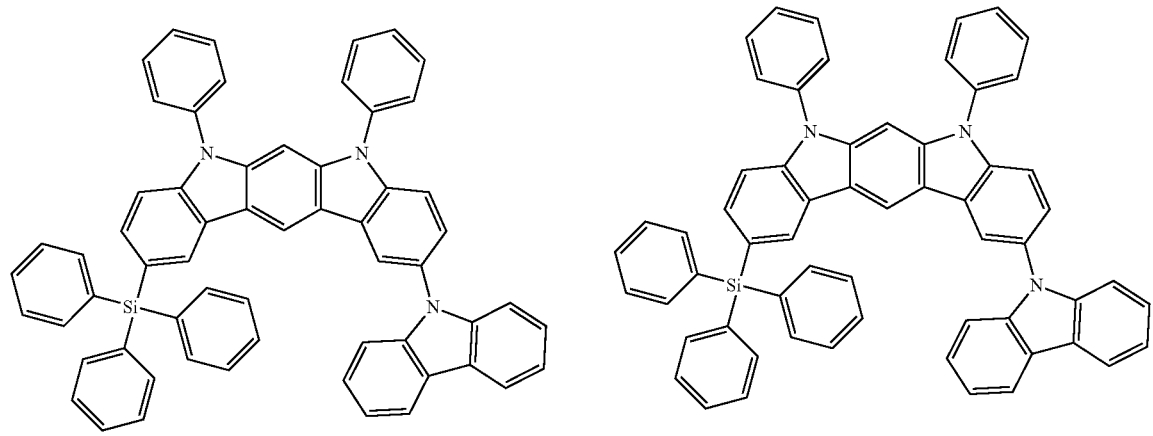

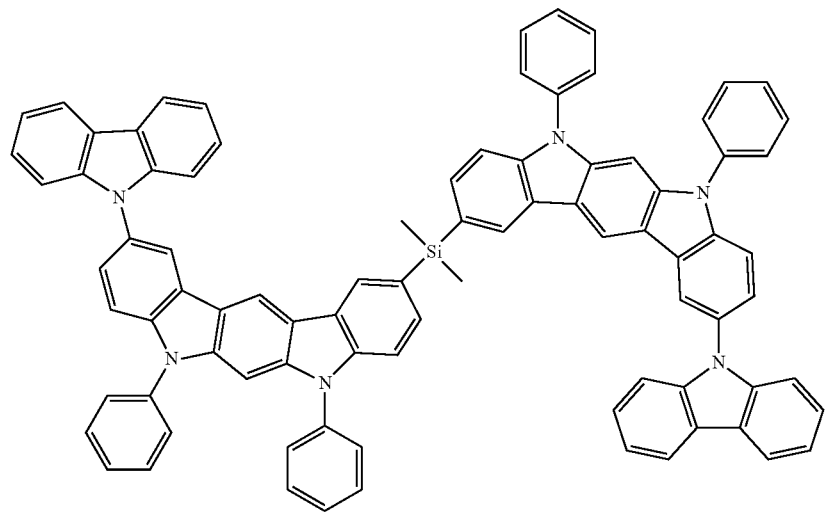 [SMILES: C[Si](C)(c1ccc2c(c1)c1cc3c4cc(-n5c6ccccc6c6ccccc65)ccc4n(-c4ccccc4)c3cc1n2-c1ccccc1)c1ccc2c(c1)c1cc3c4cc(-n5c6ccccc6c6ccccc65)ccc4n(-c4ccccc4)c3cc1n2-c1ccccc1]
Examples of suitable benzofuranyl- and benzothiophenyl-carbazoles are:
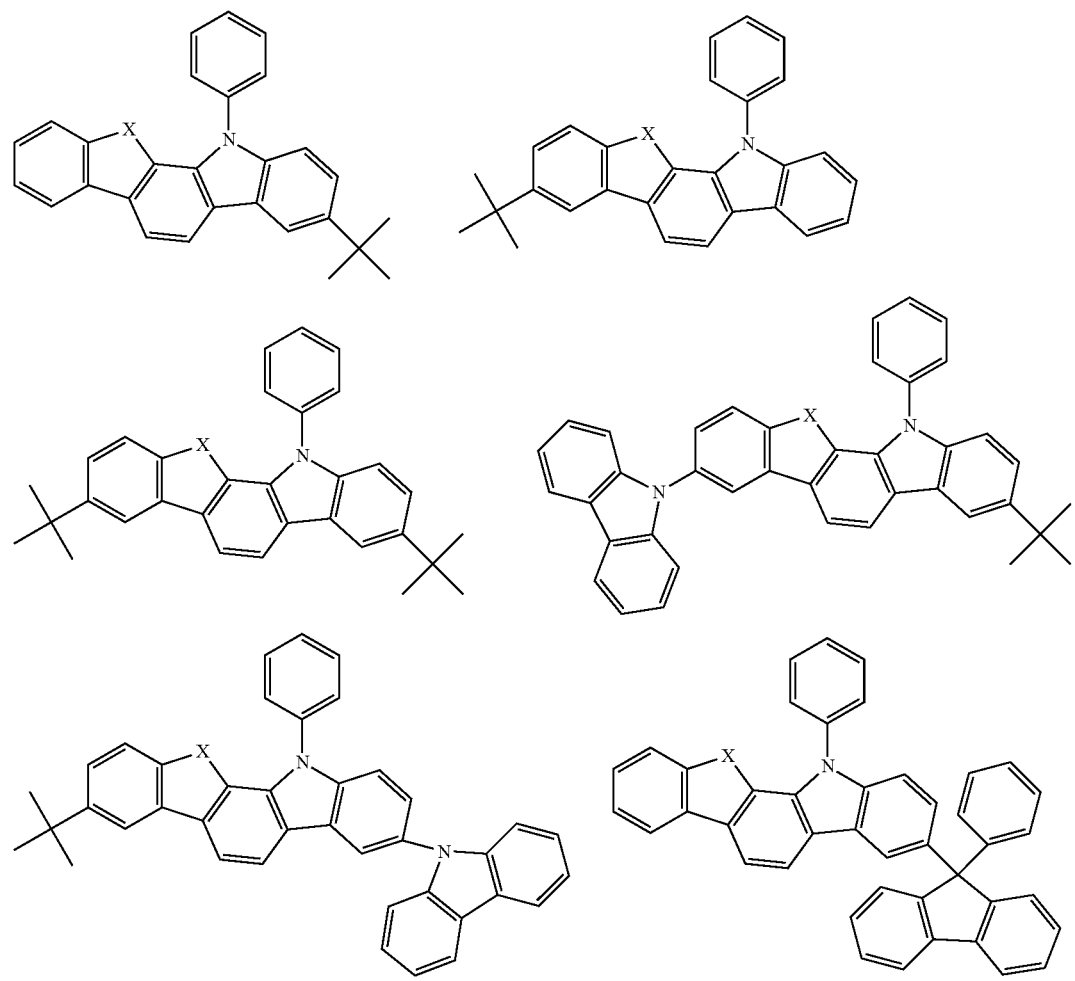

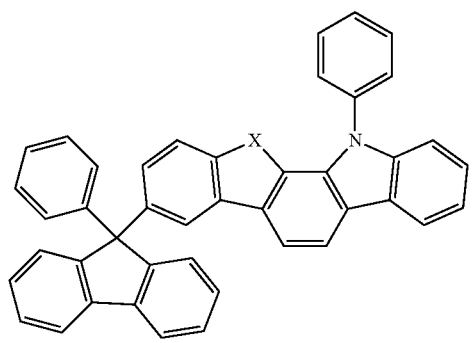
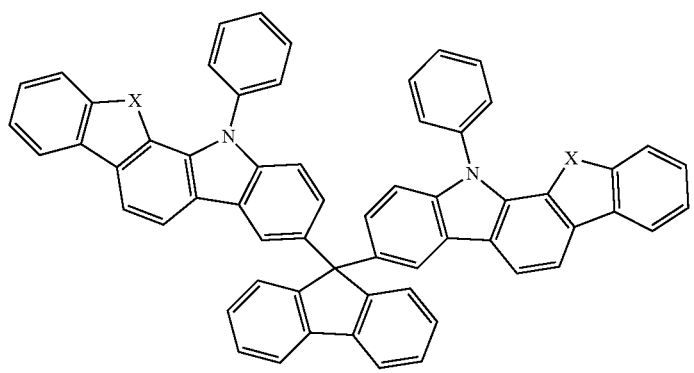
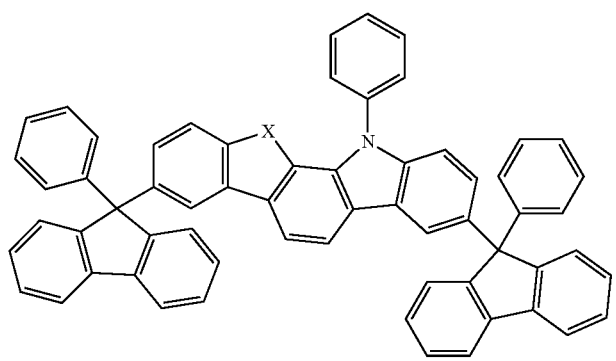
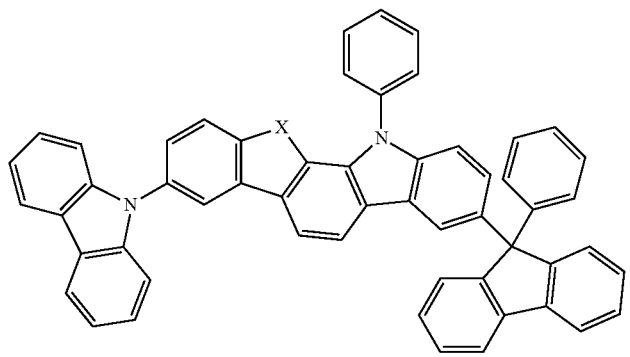

-continued
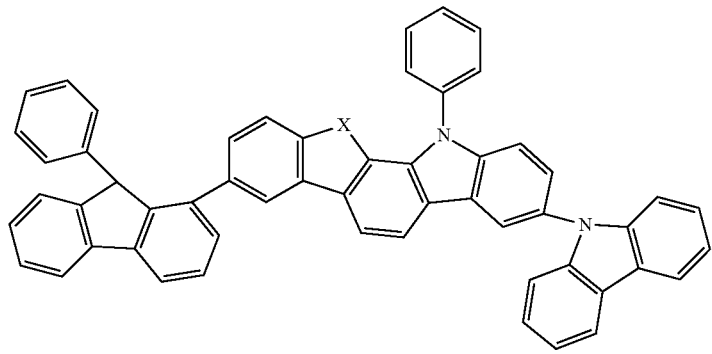
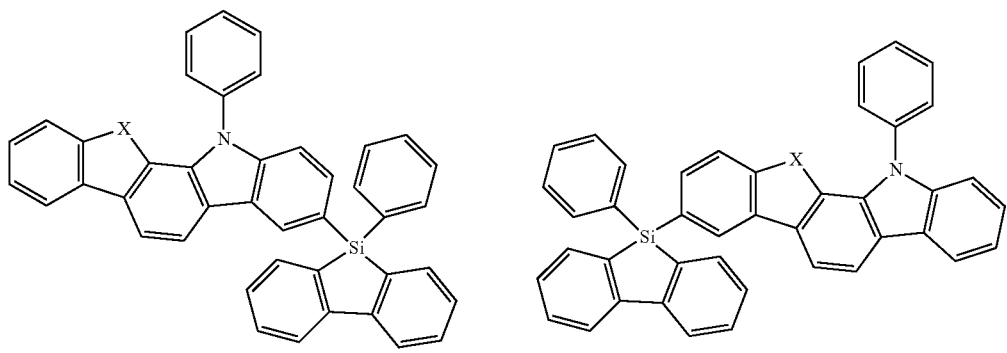
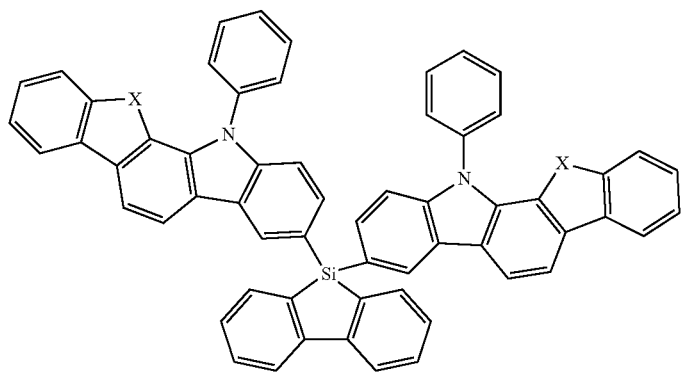
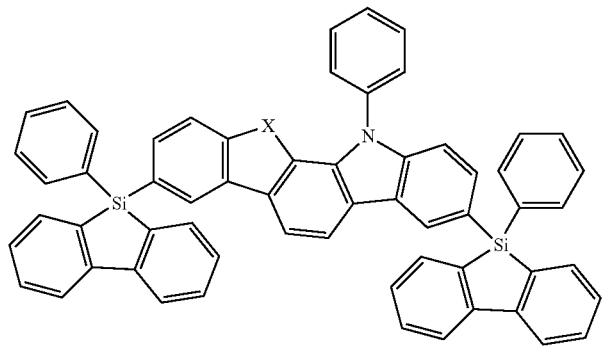

-continued
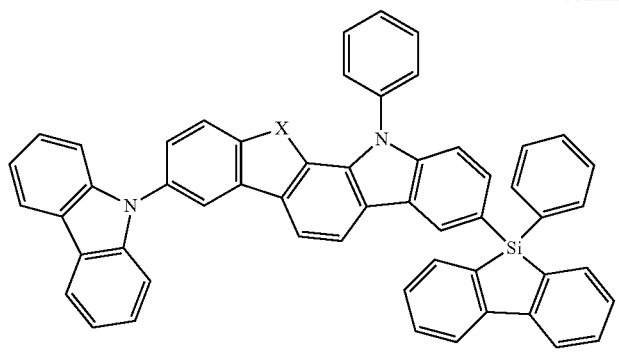
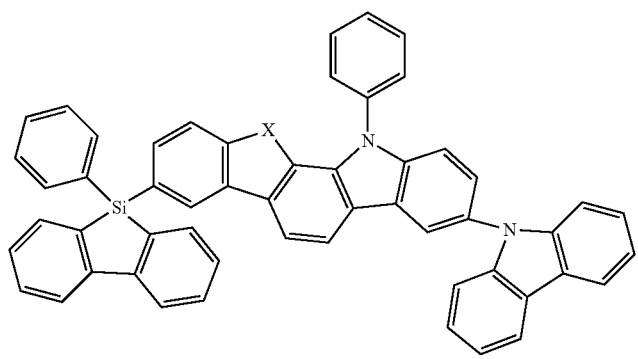
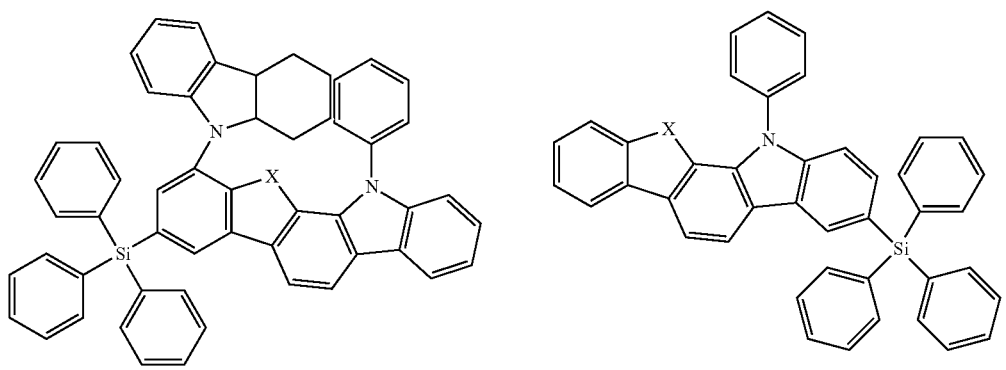
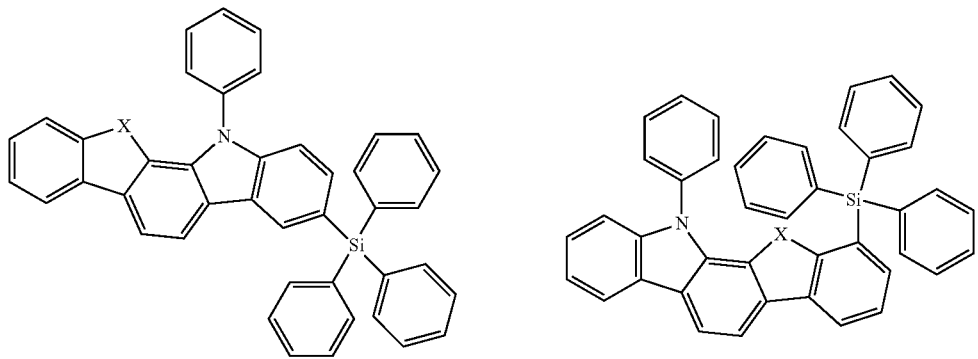

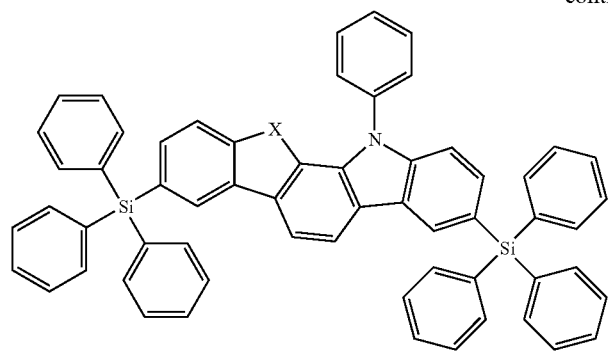
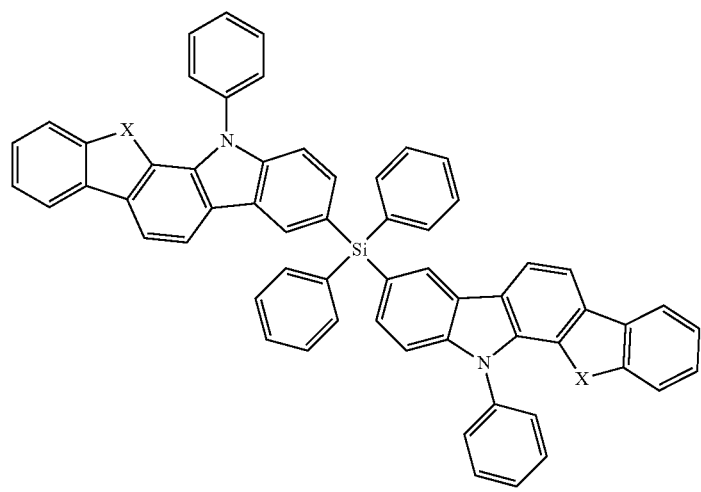
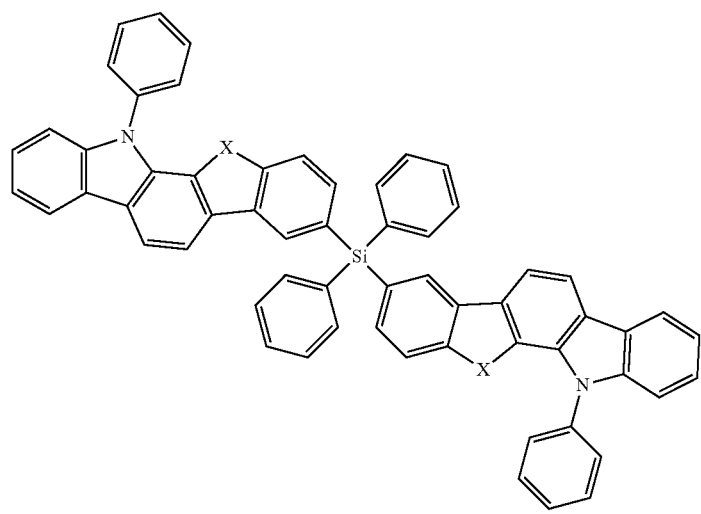

-continued
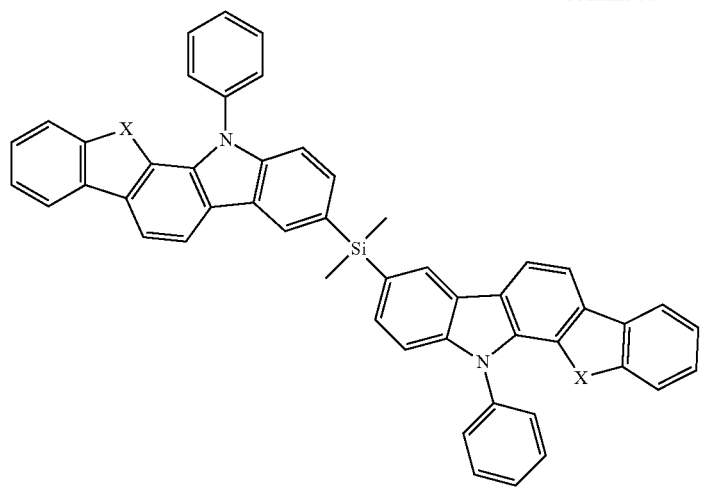
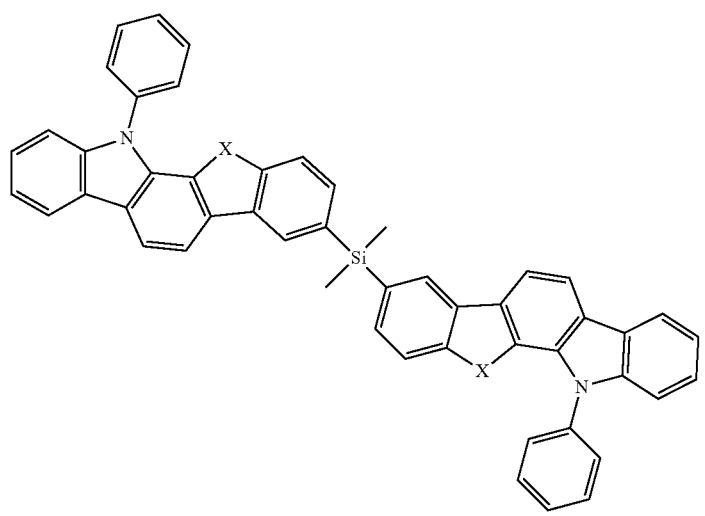
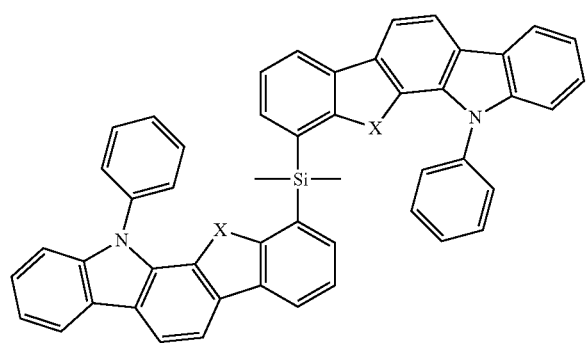
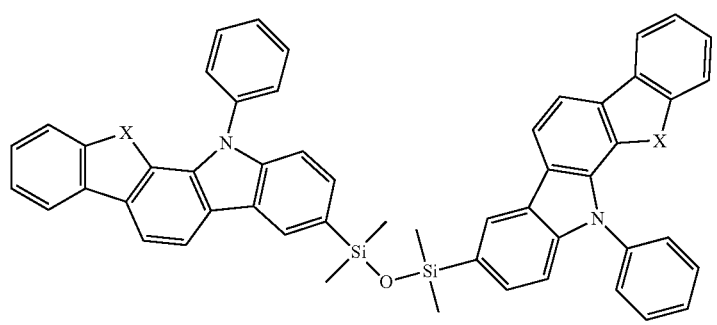

-continued
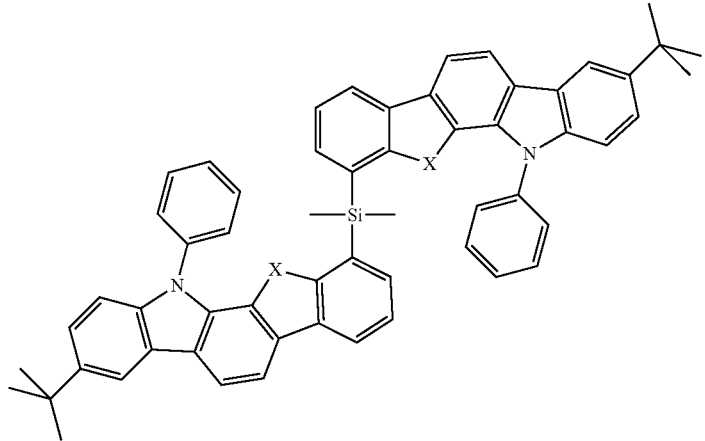
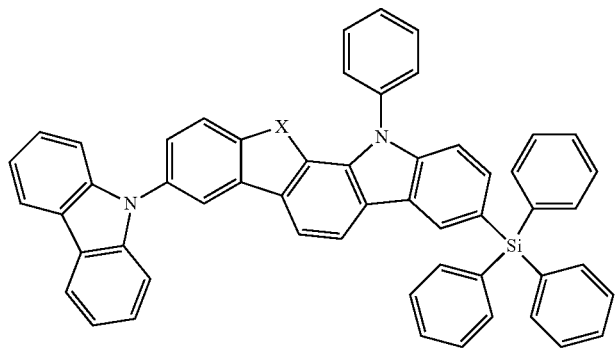
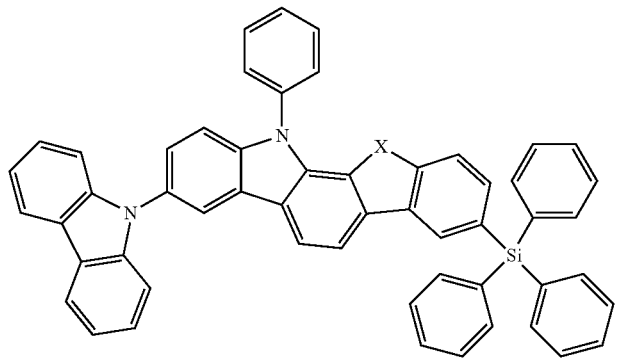
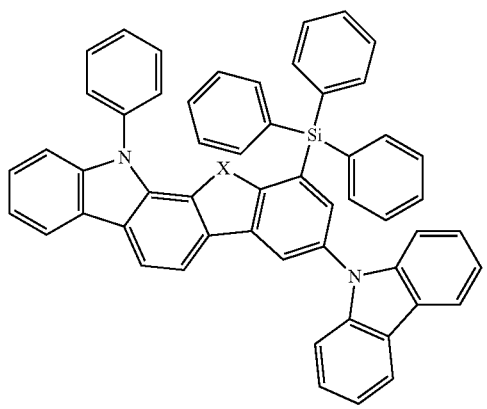

-continued
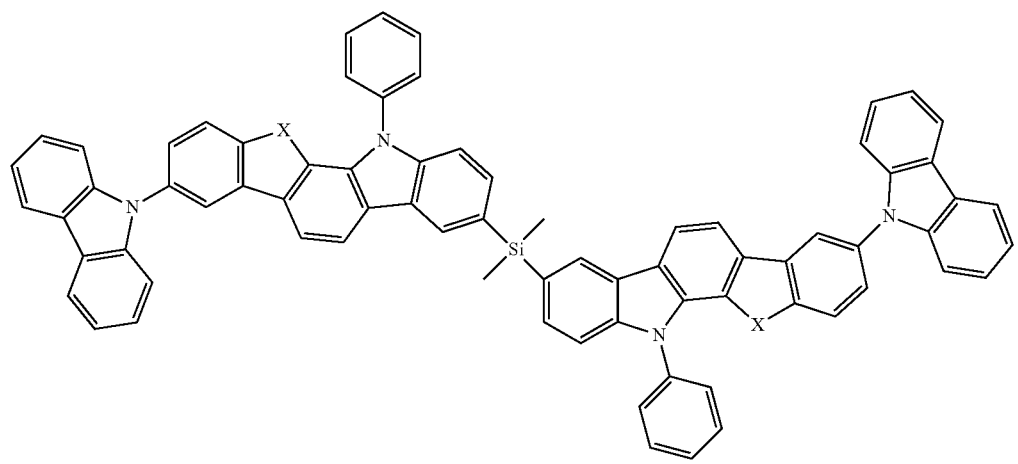
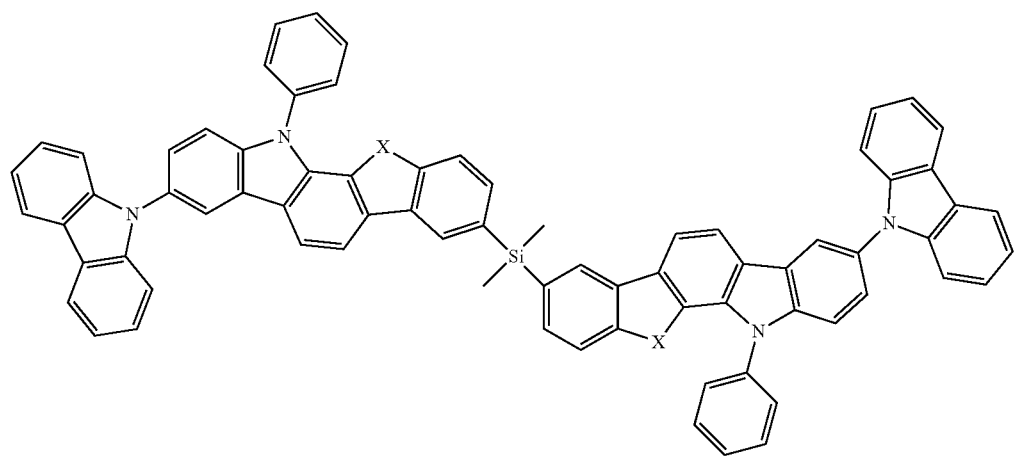
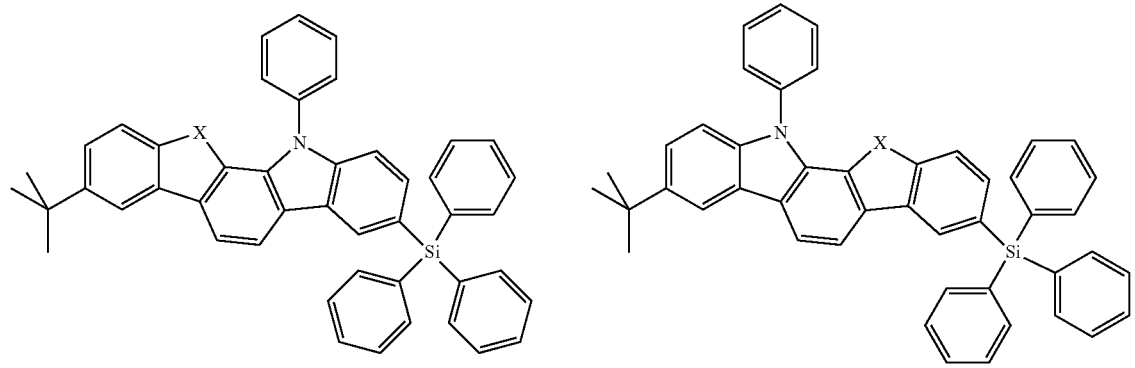
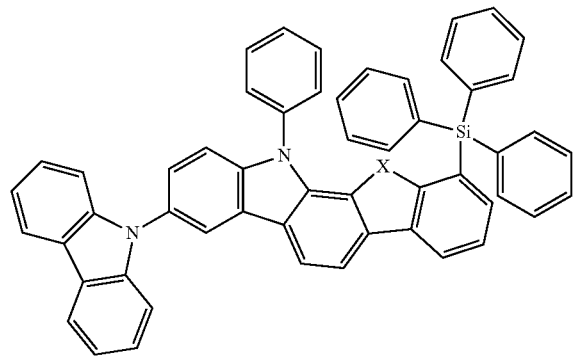

-continued
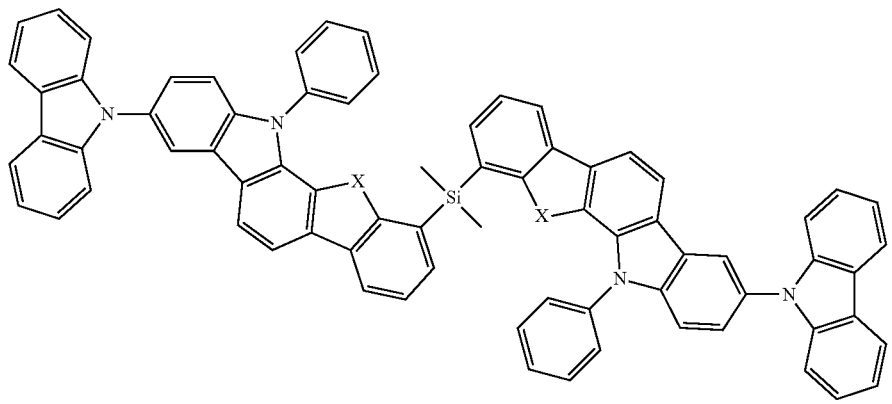
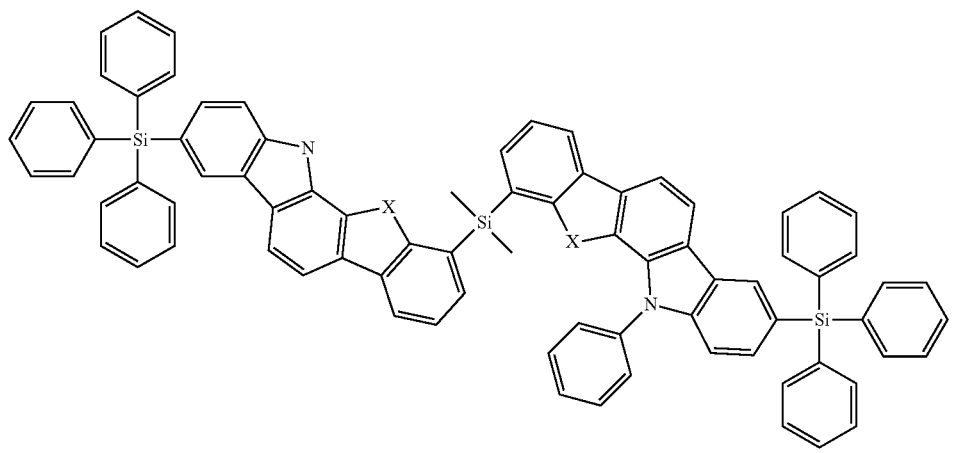
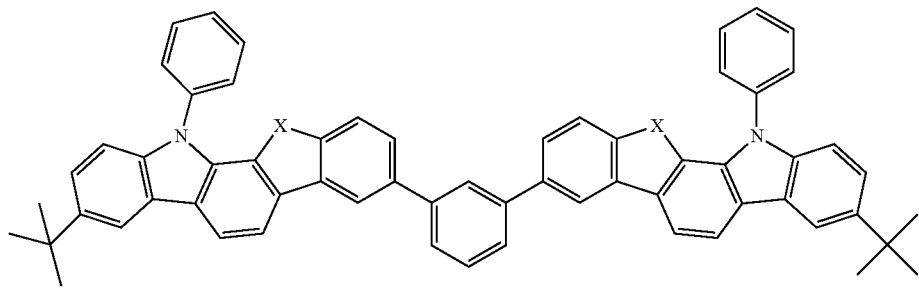
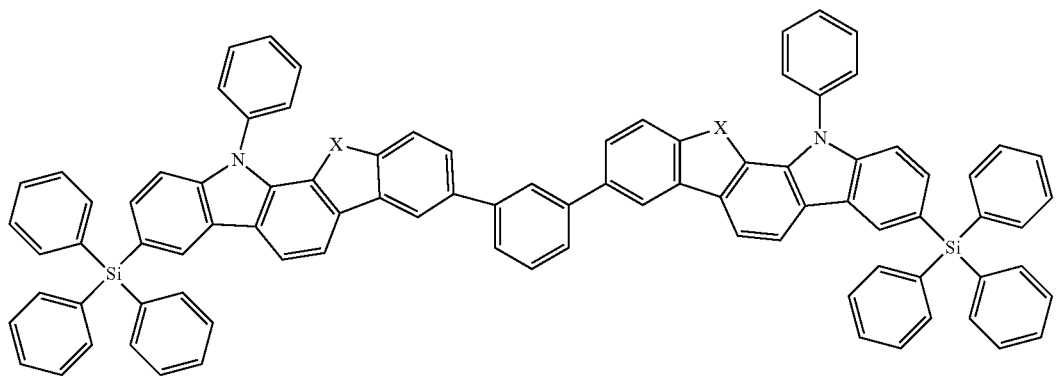

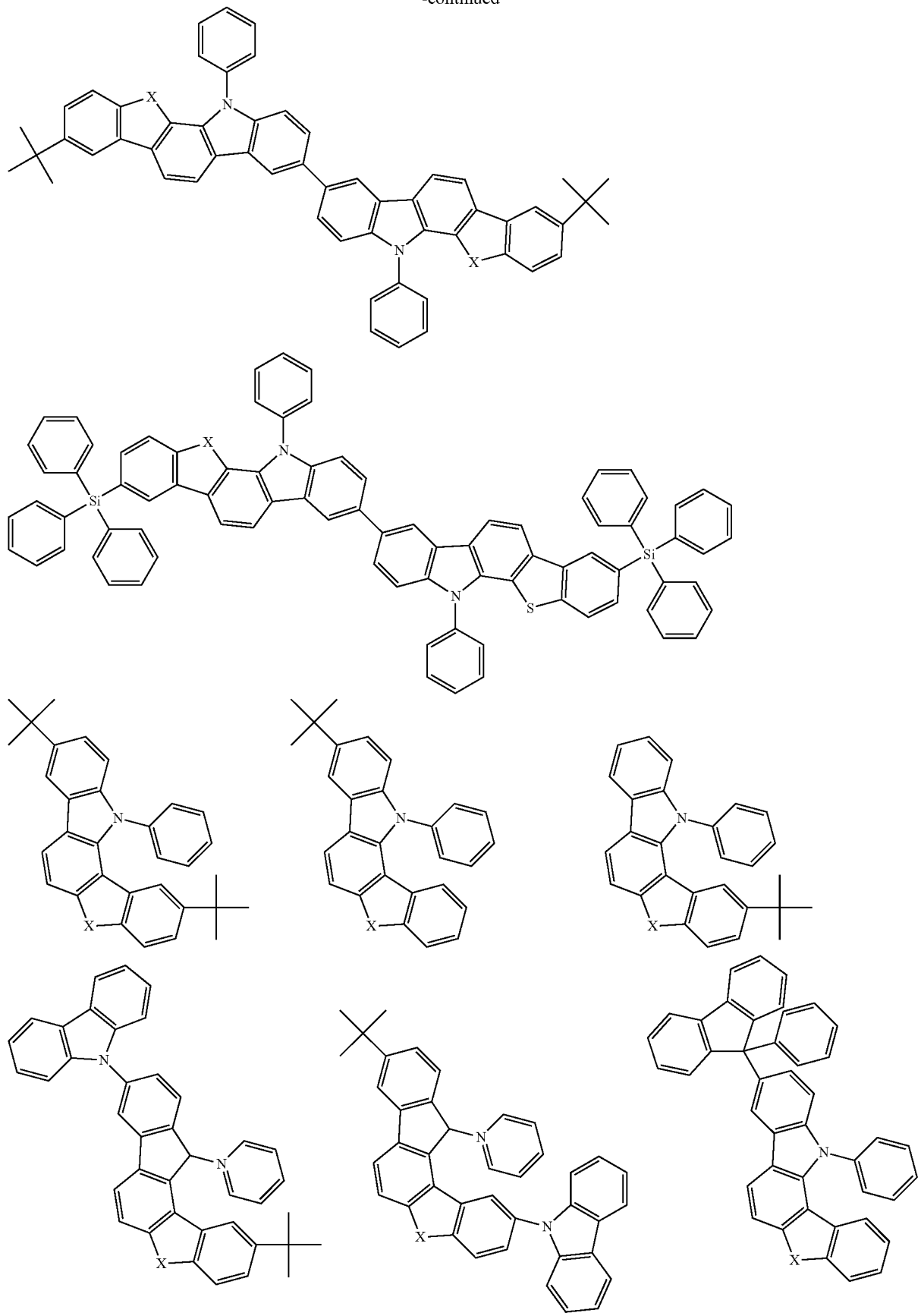

-continued
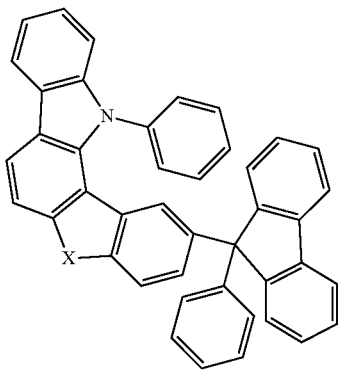 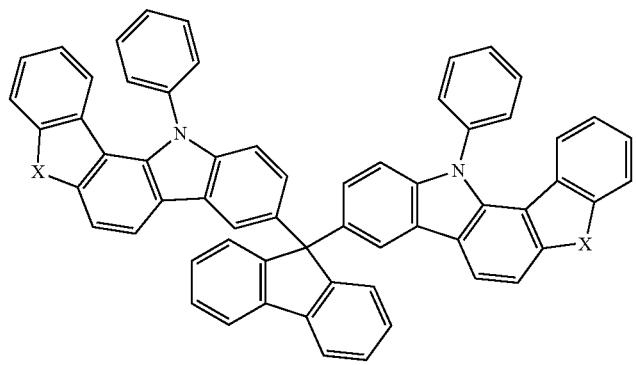
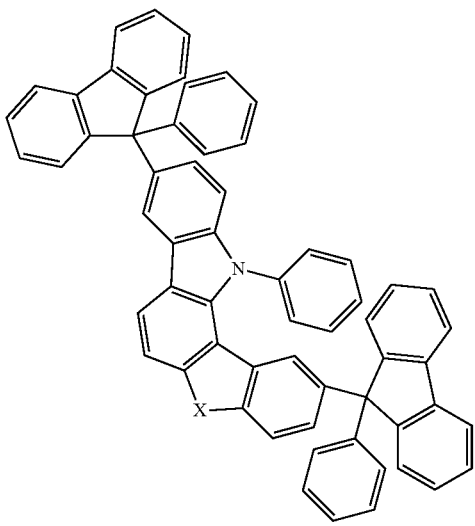 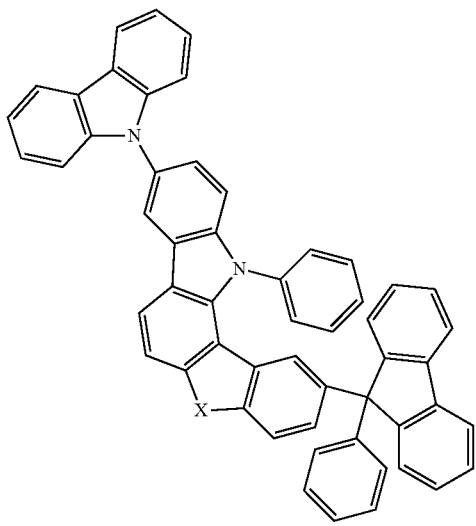
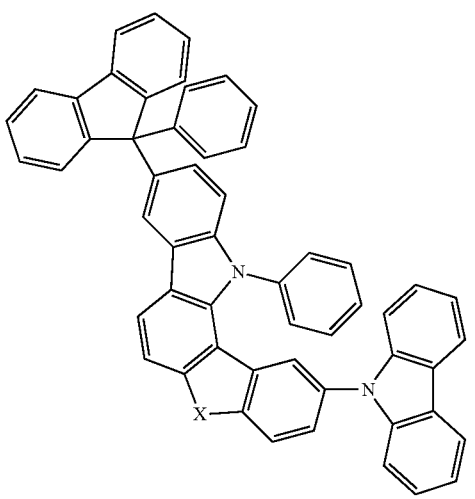 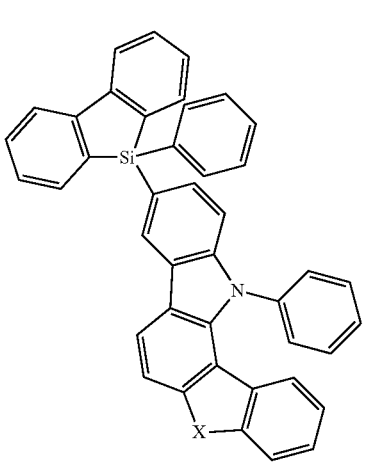

-continued
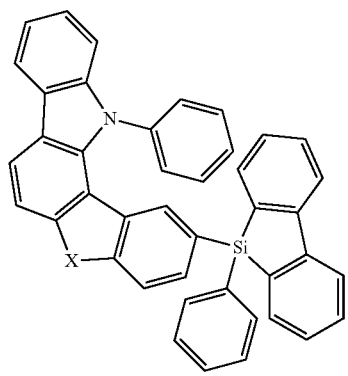
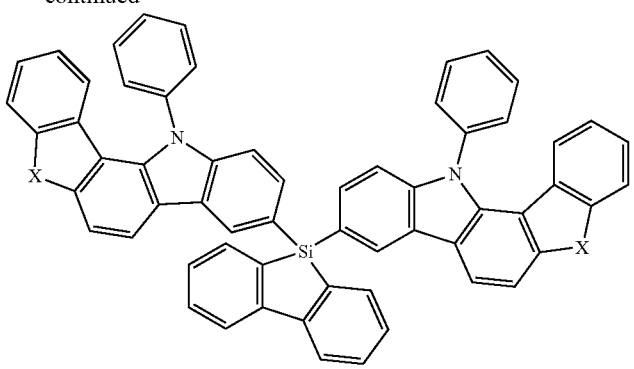
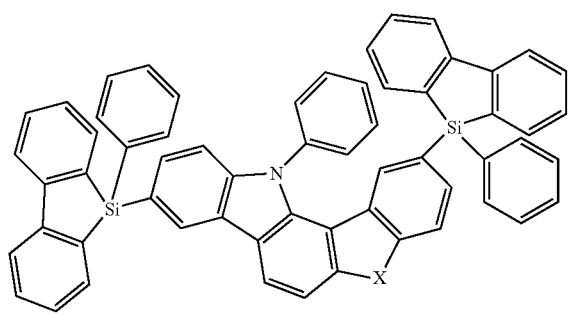
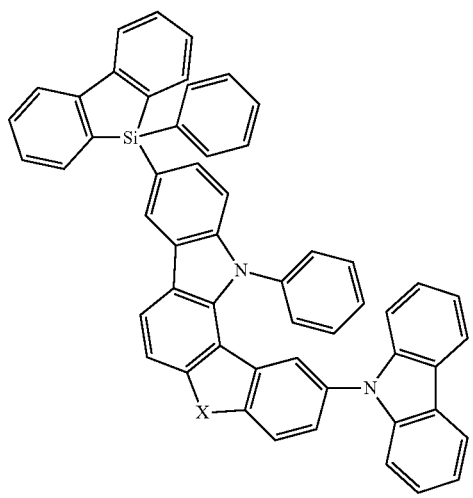
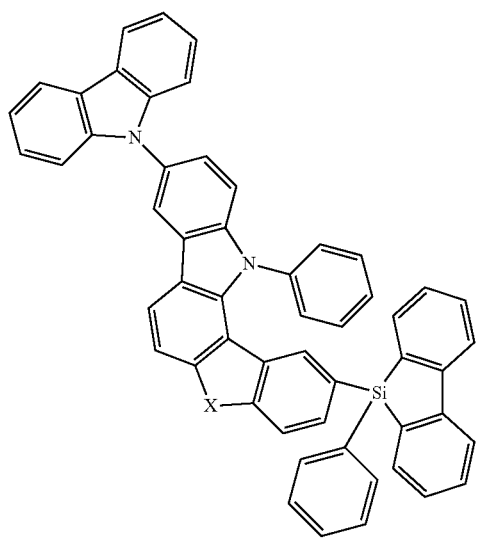
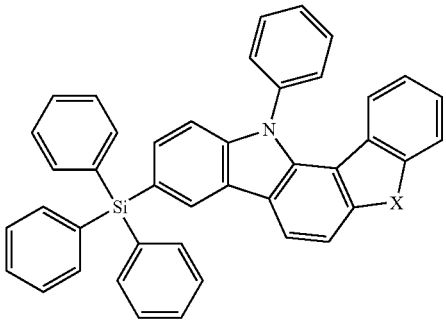

-continued
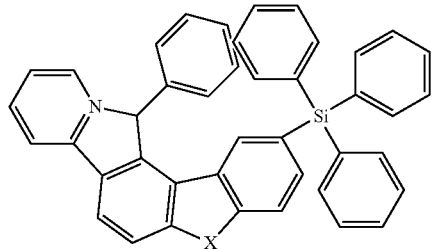
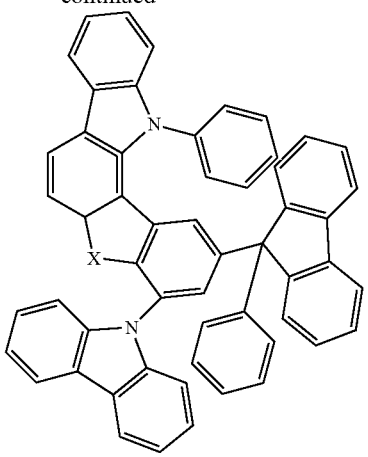
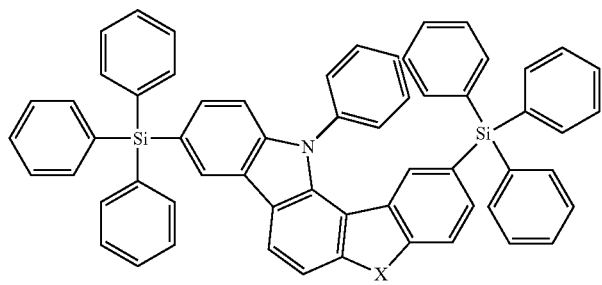
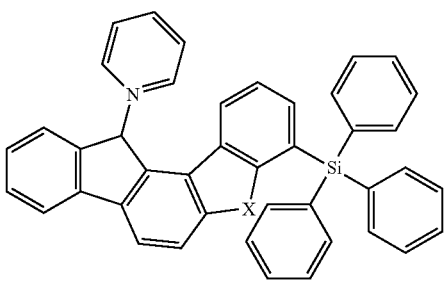
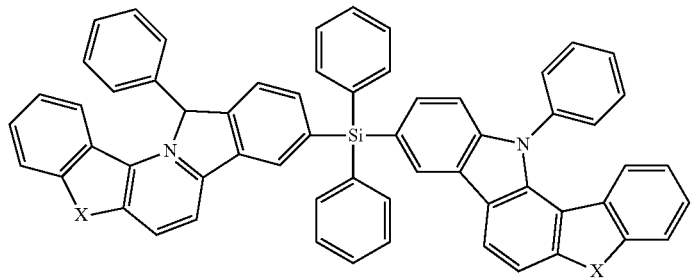
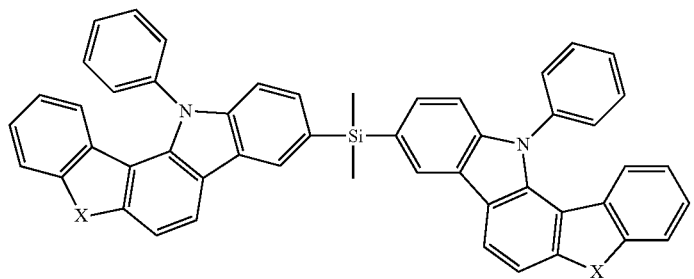
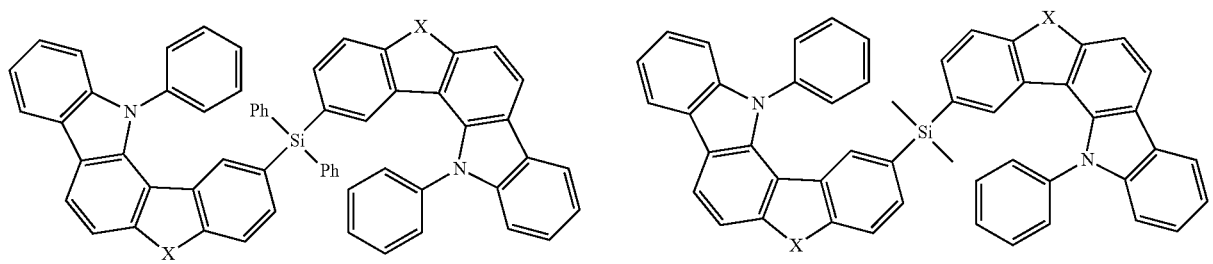

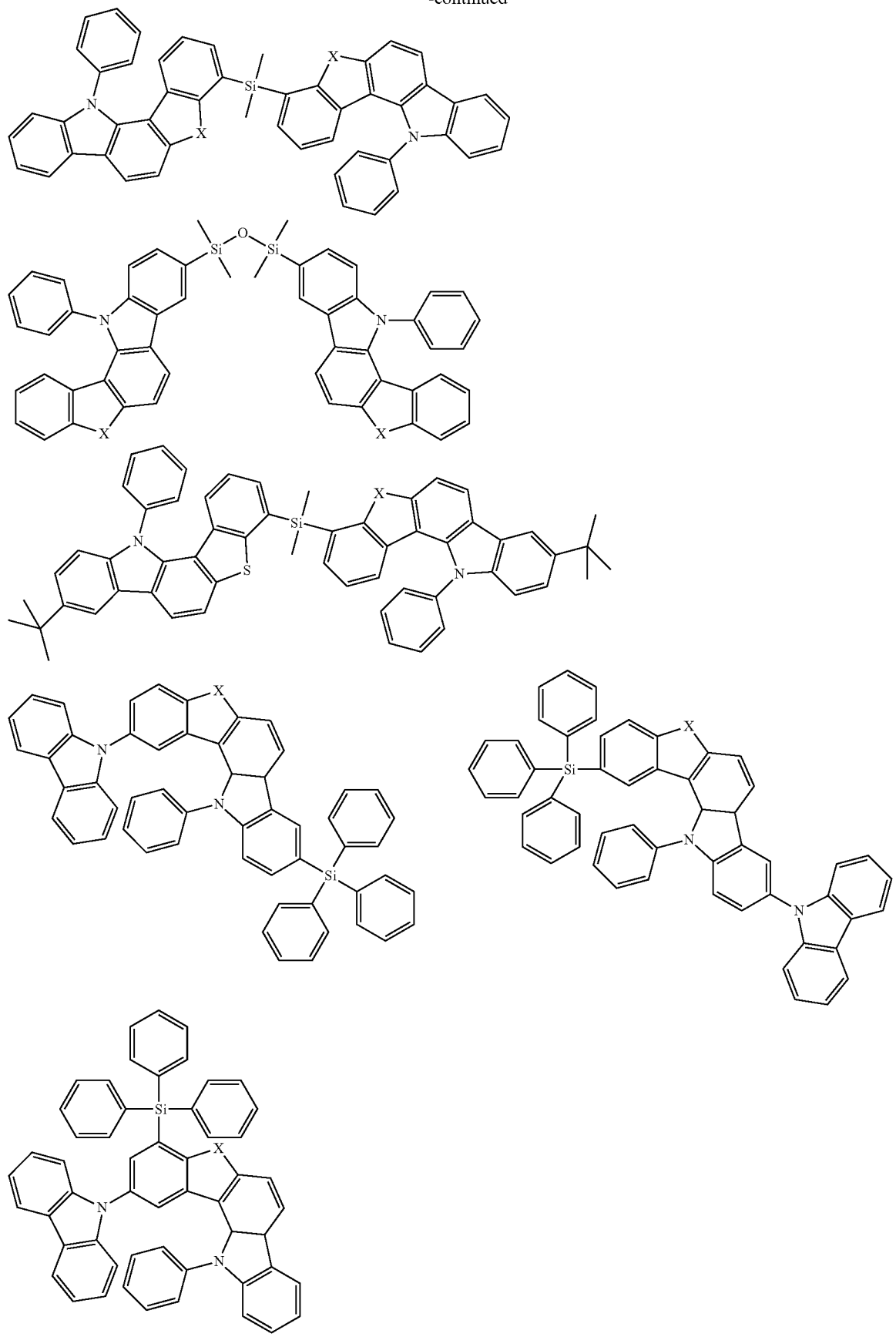

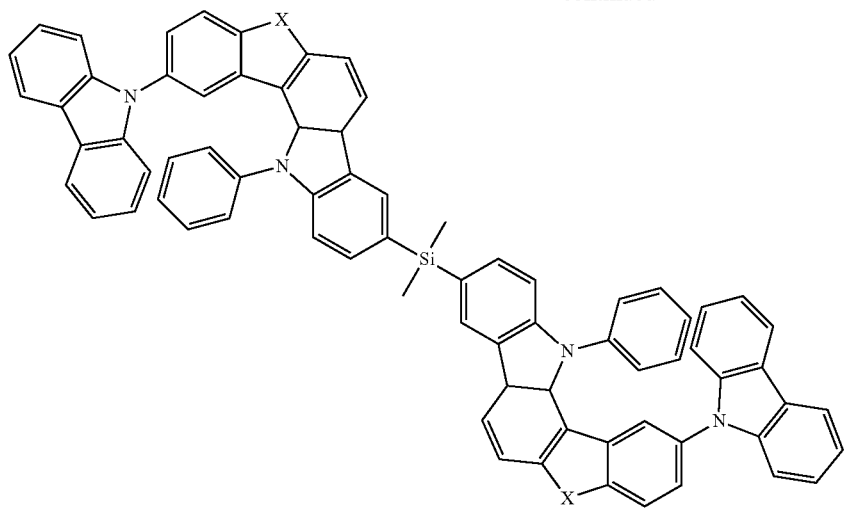
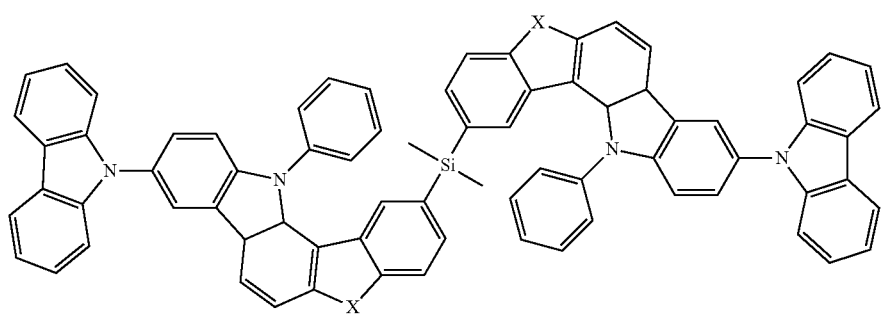
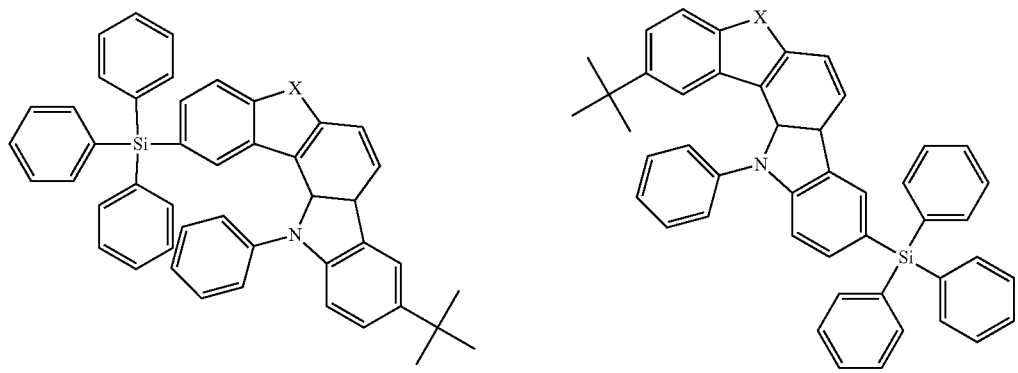
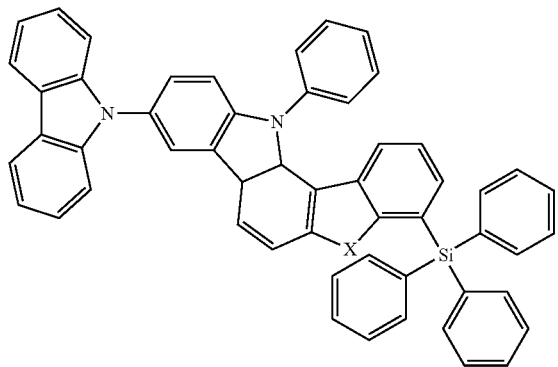

-continued
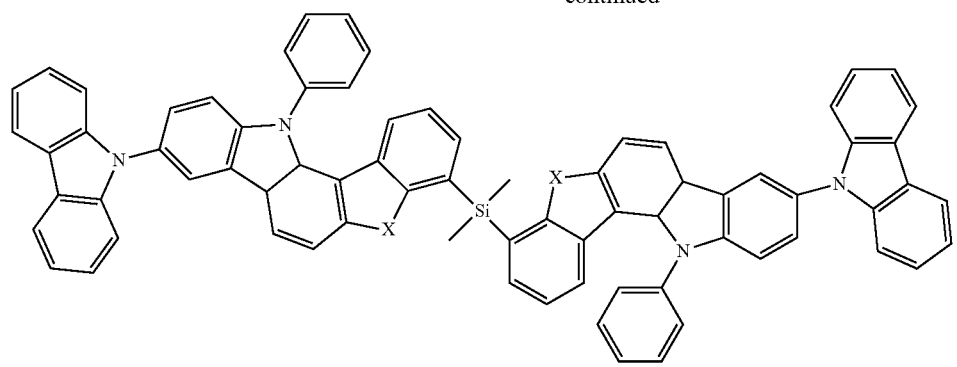
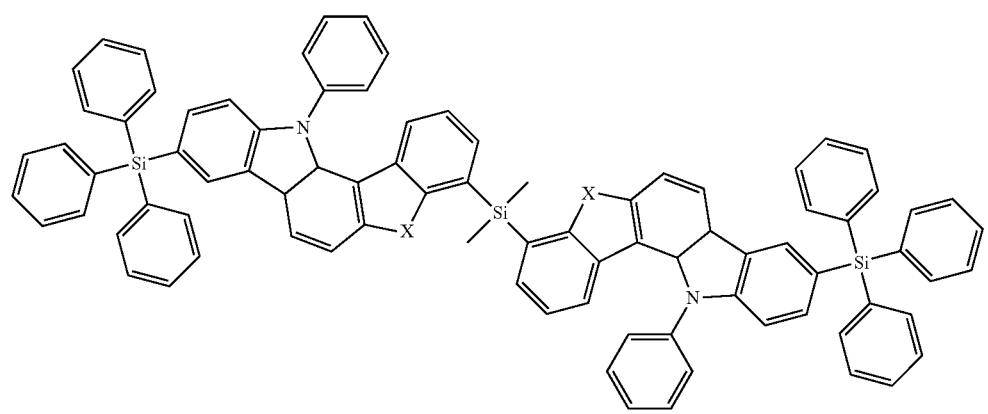
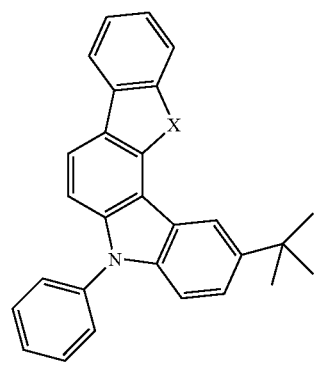 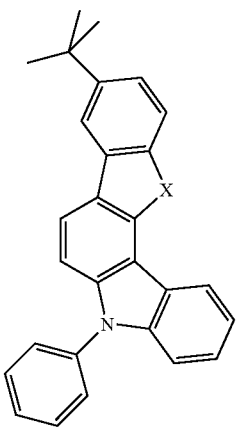 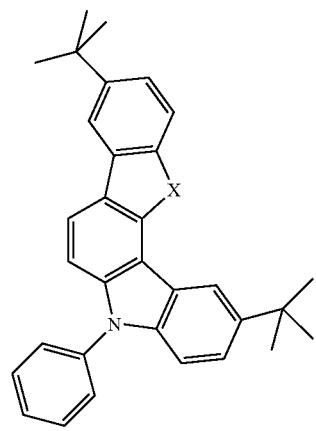
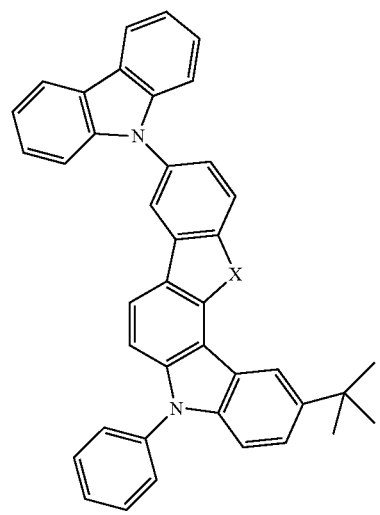 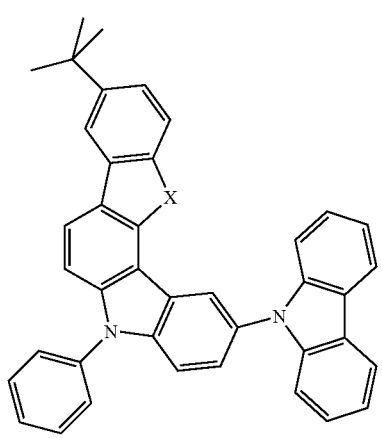

-continued
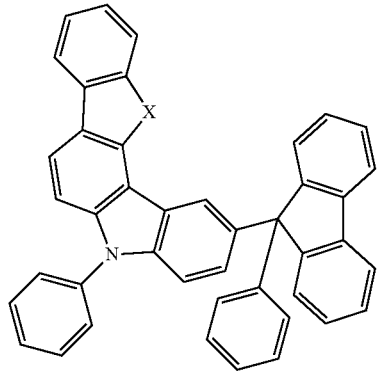
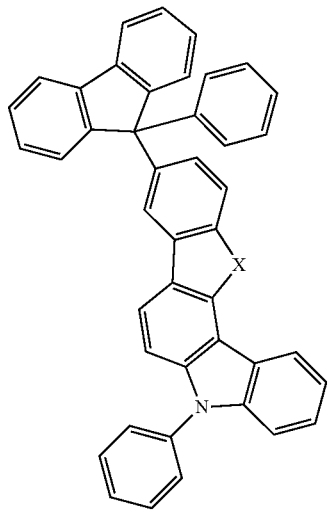
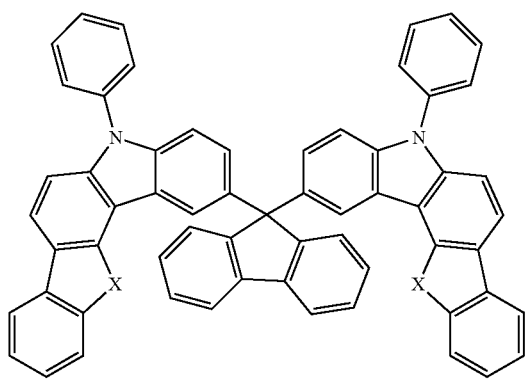
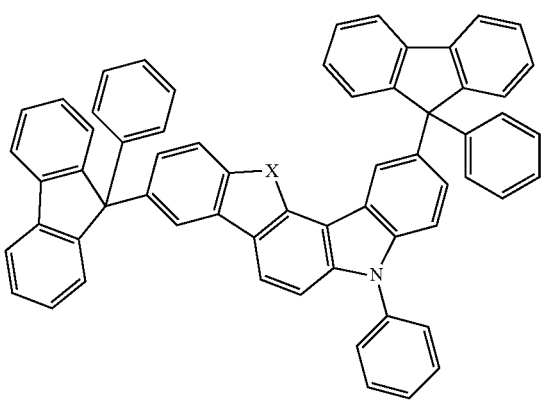
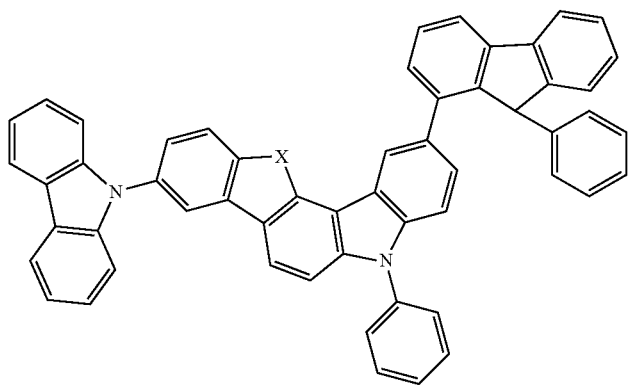
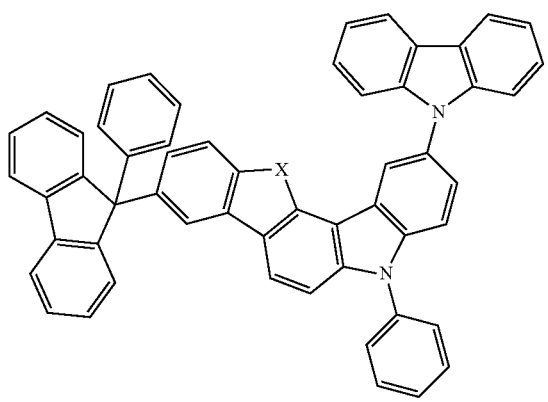
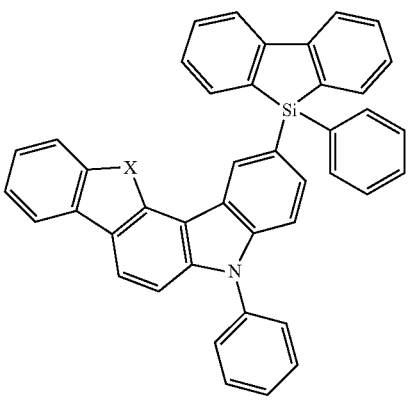

-continued
81
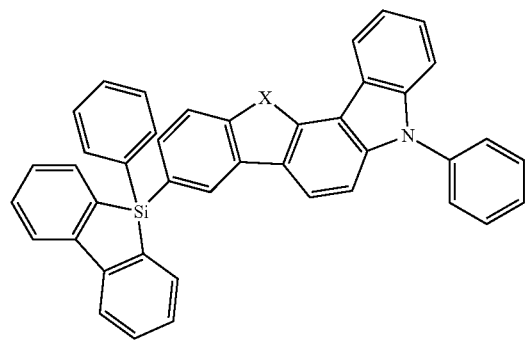
82
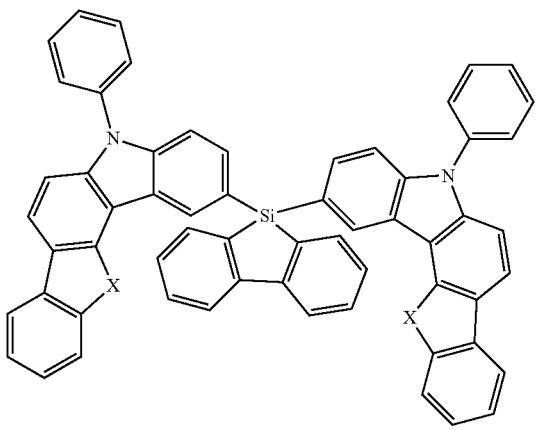
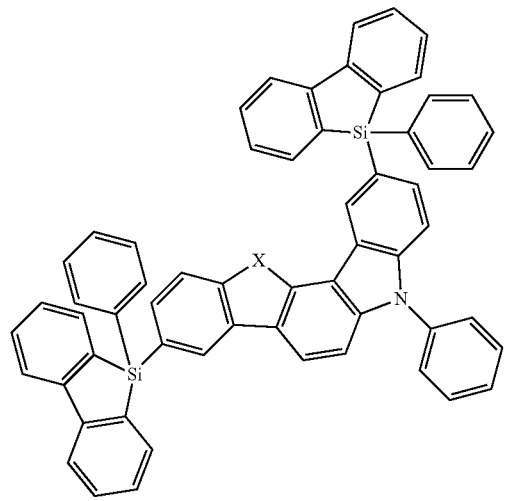
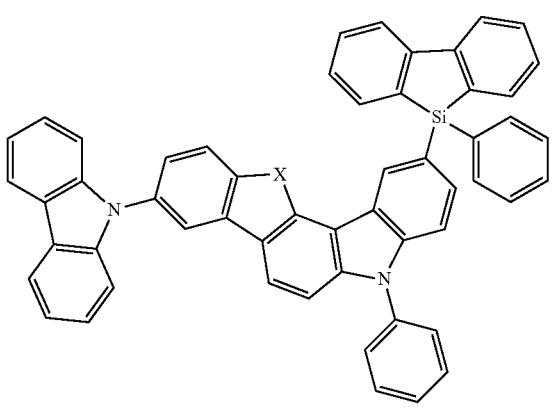
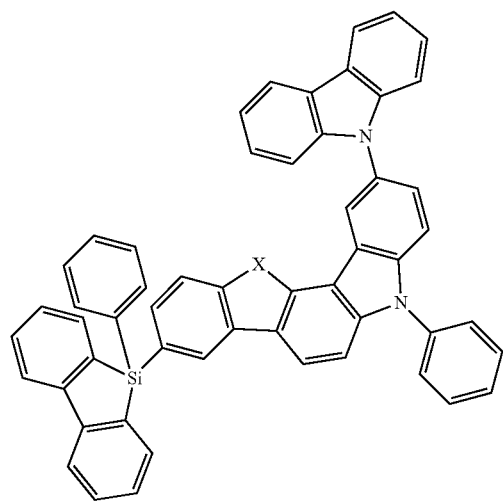
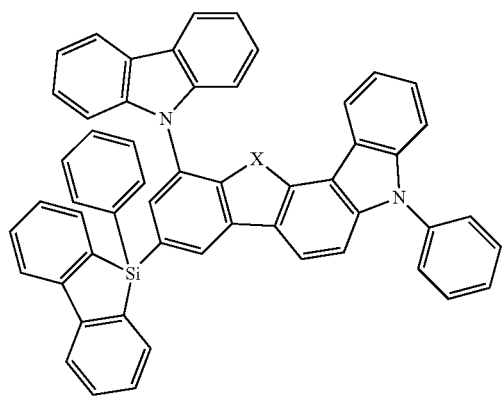

-continued
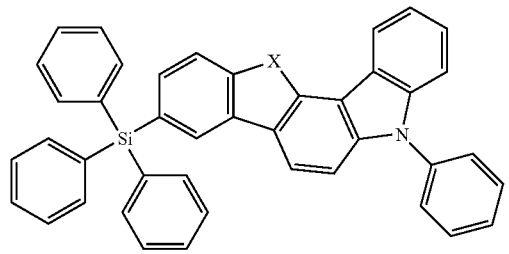
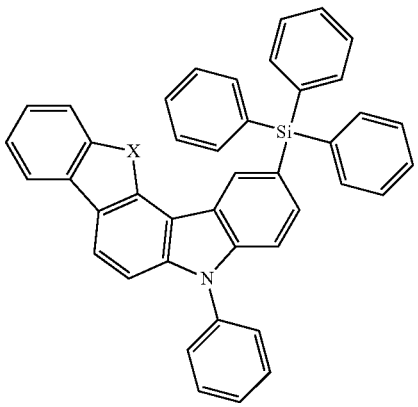
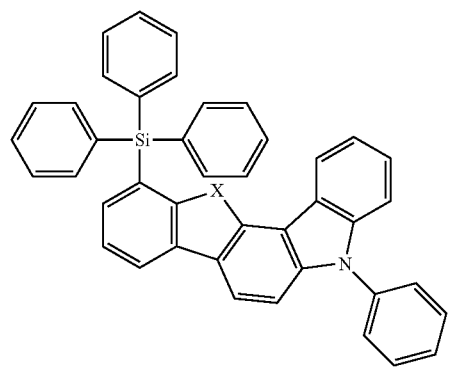
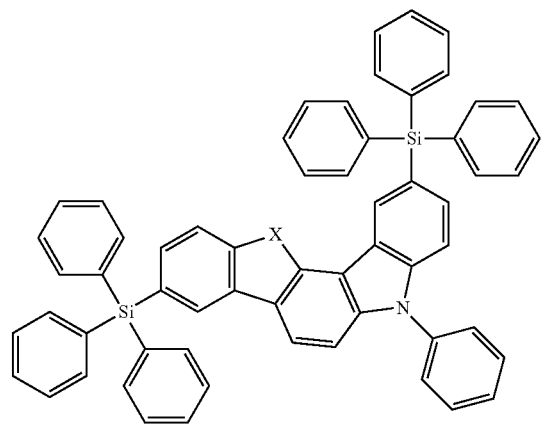
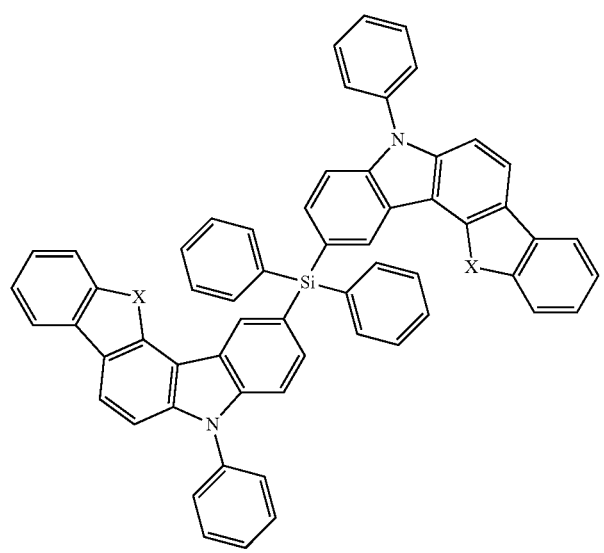
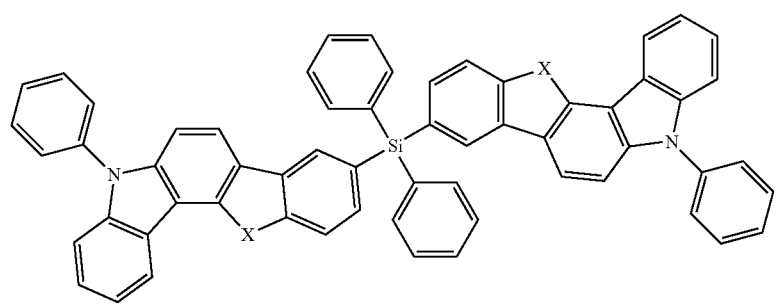

-continued
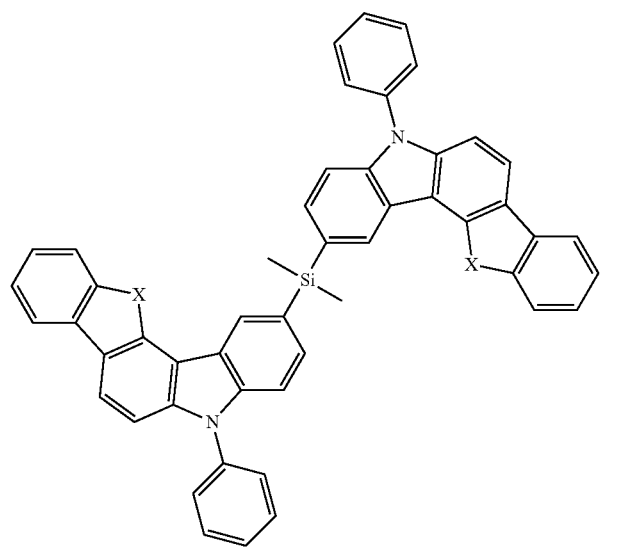
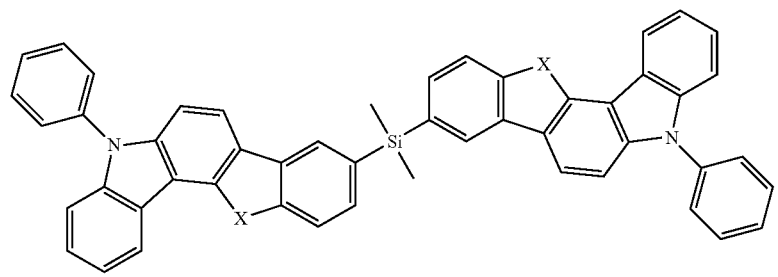
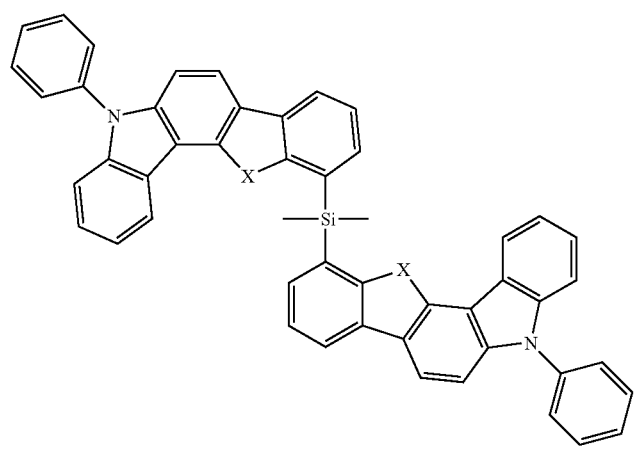
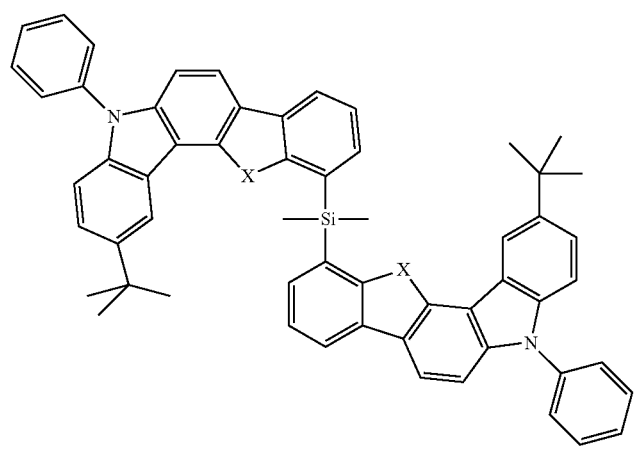

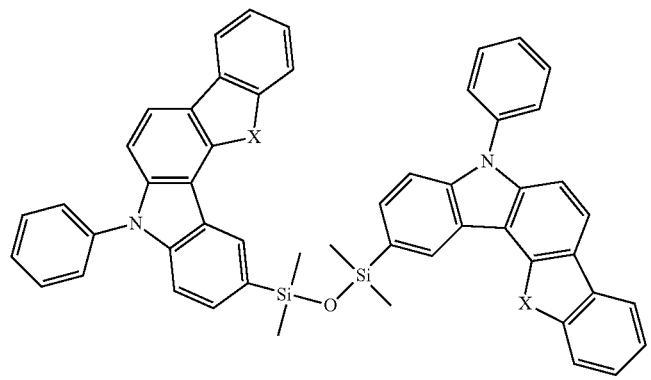
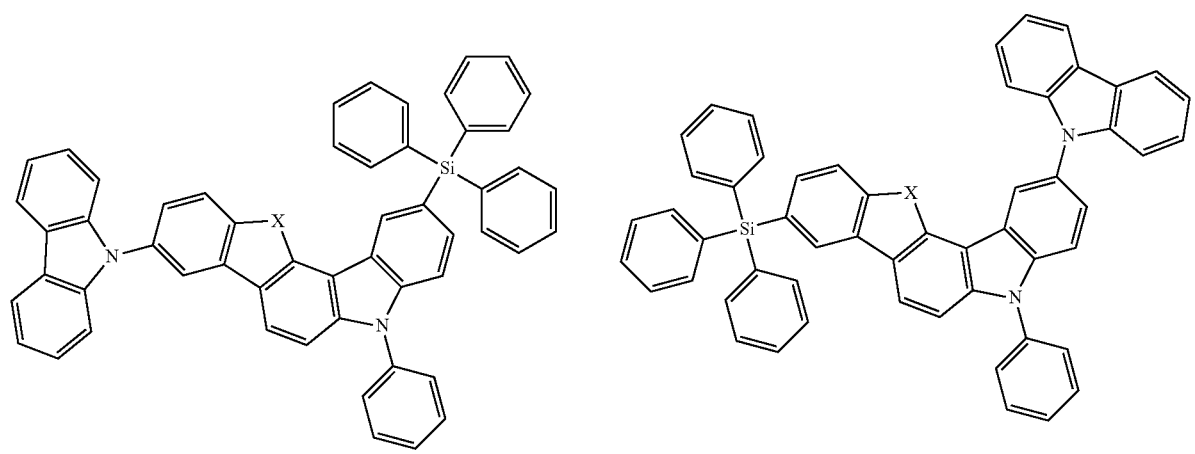
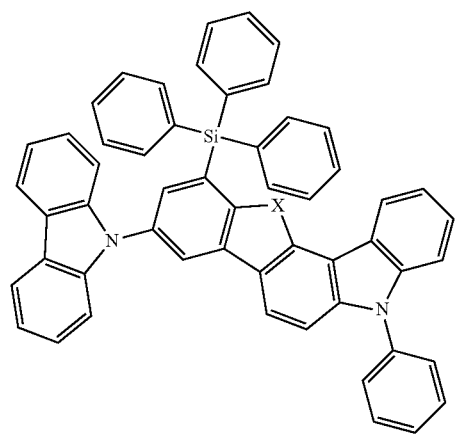

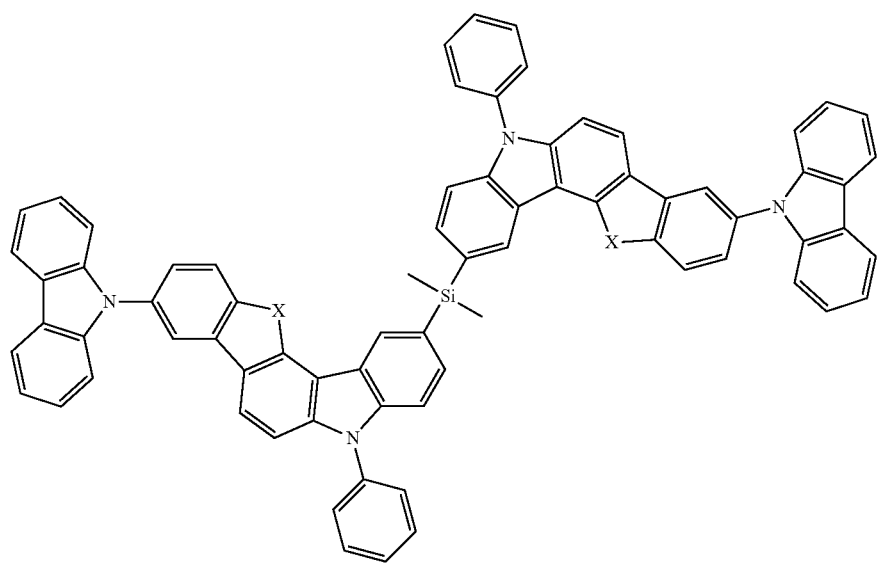
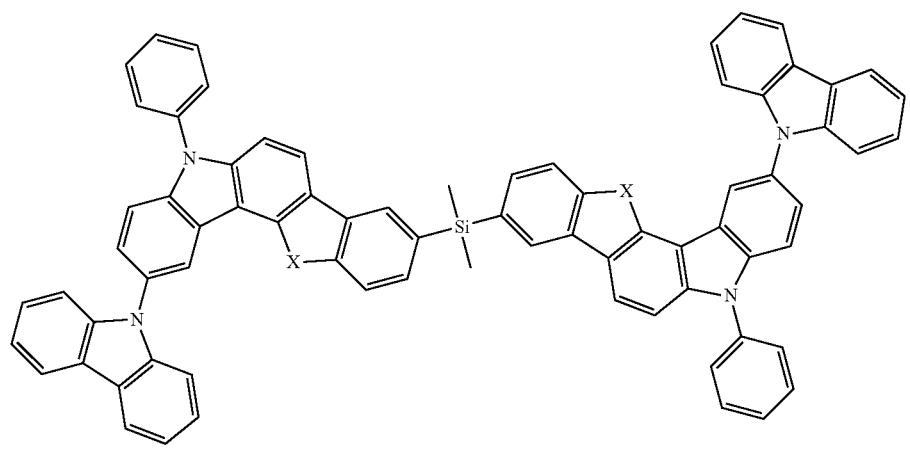
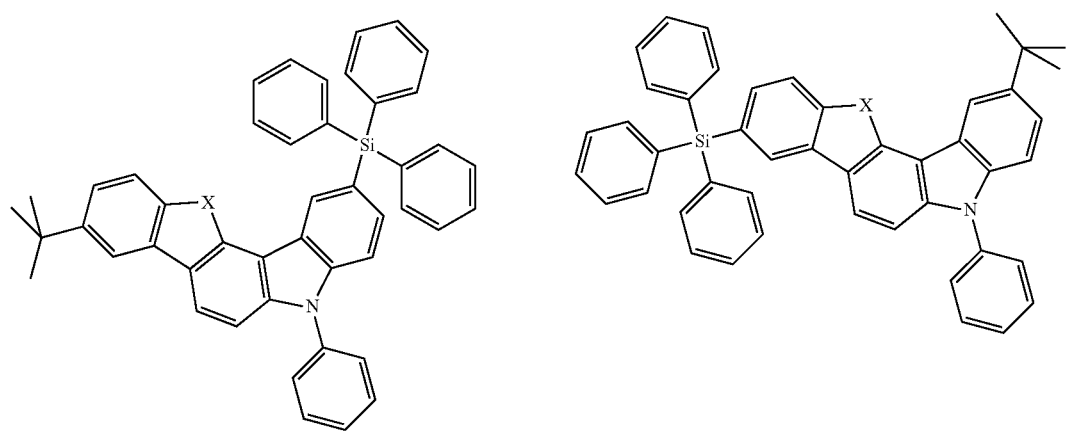

-continued
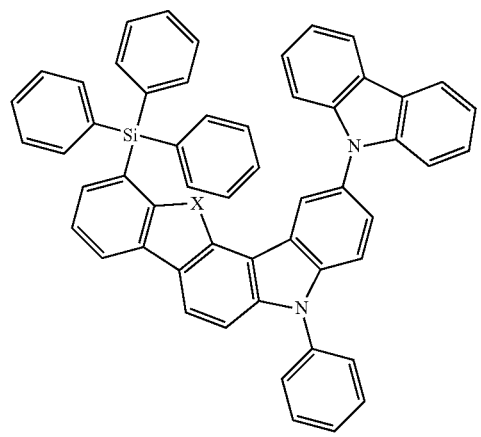
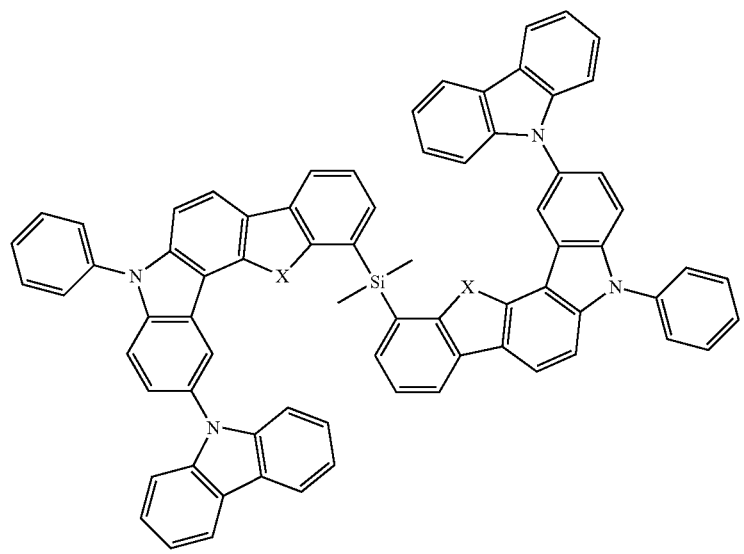
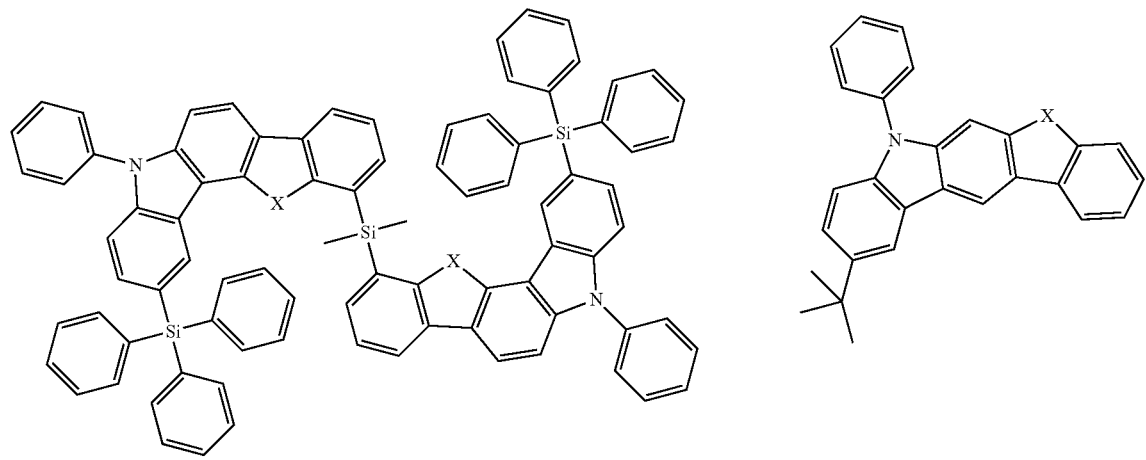

-continued
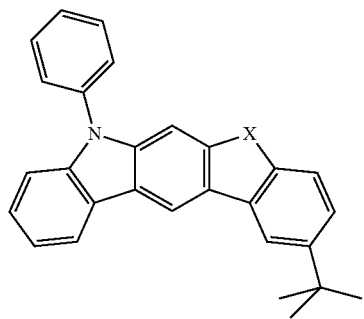
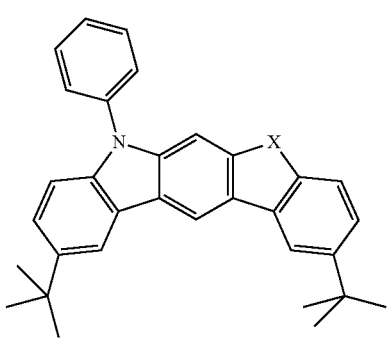
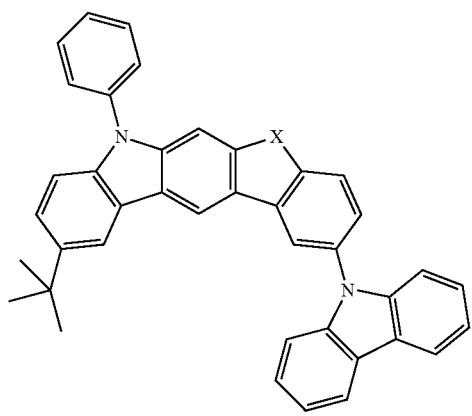
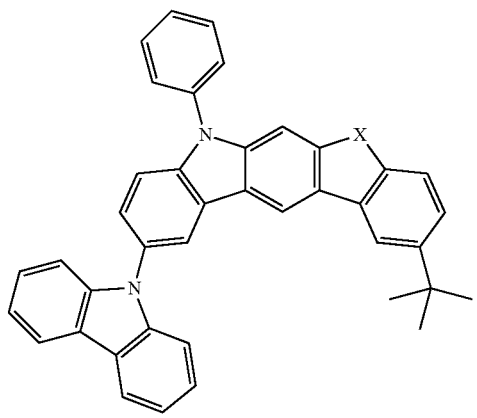
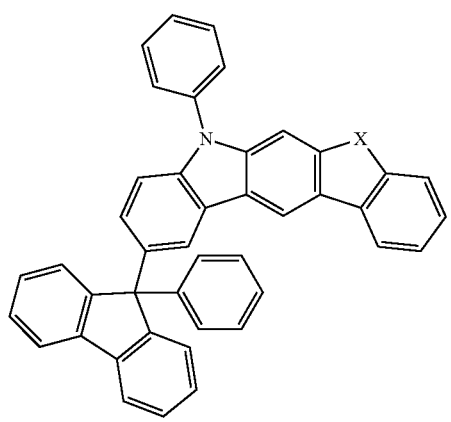
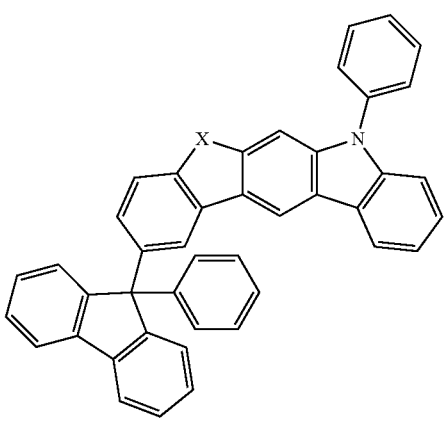
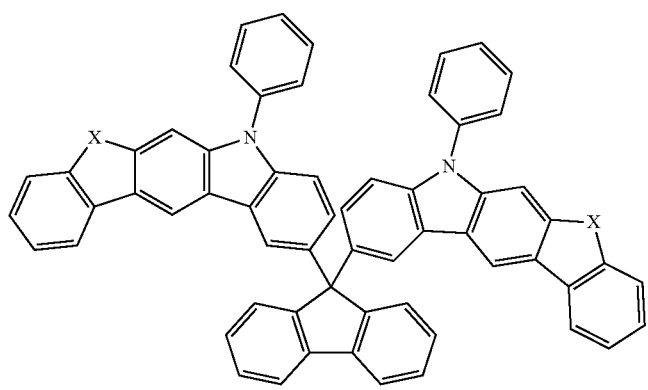

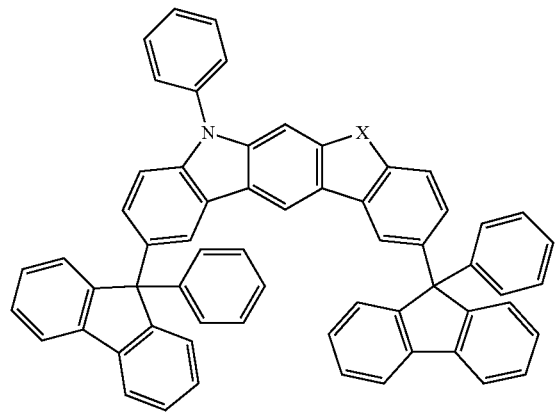
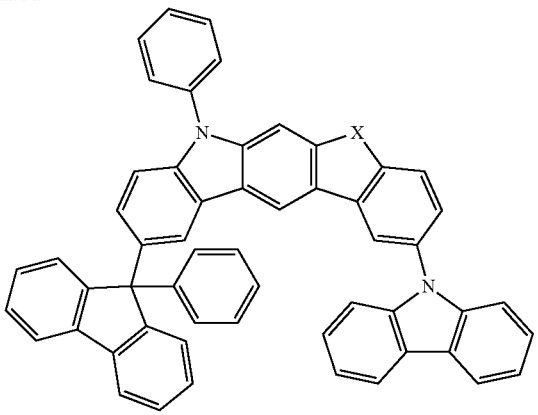
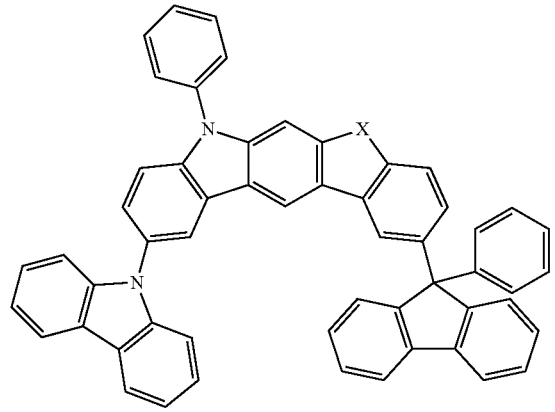
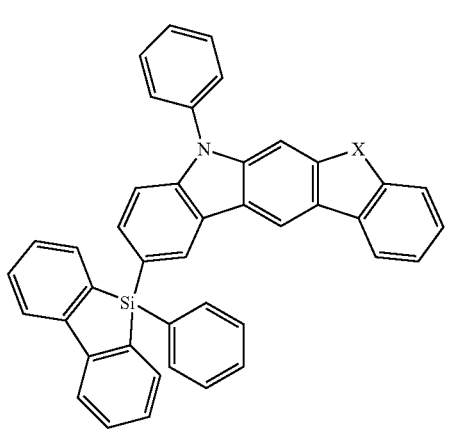
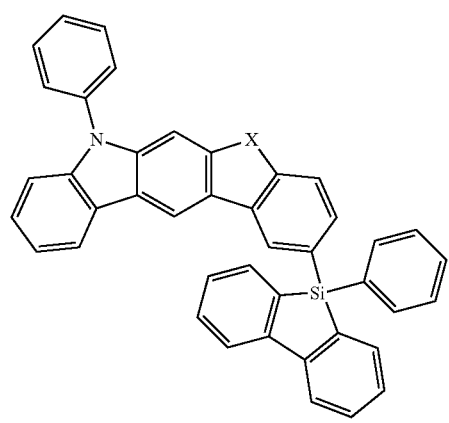
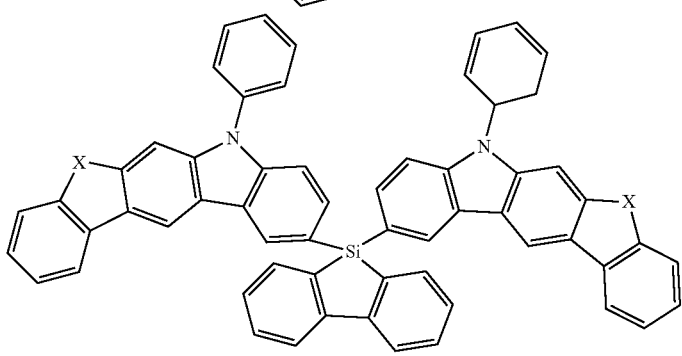
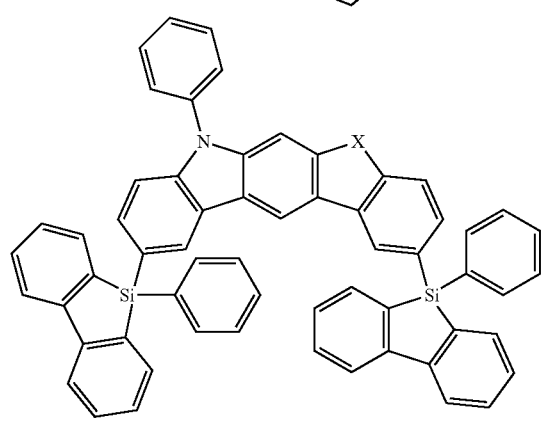
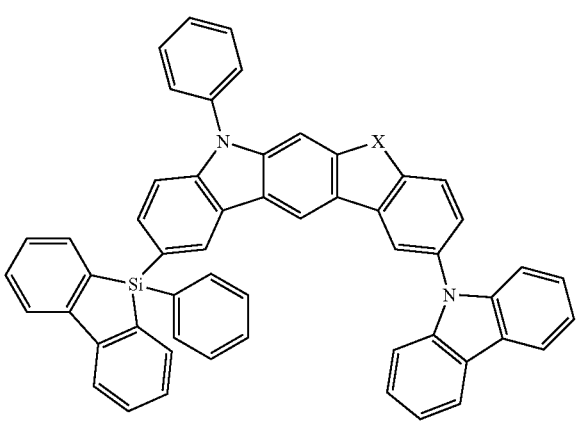

97
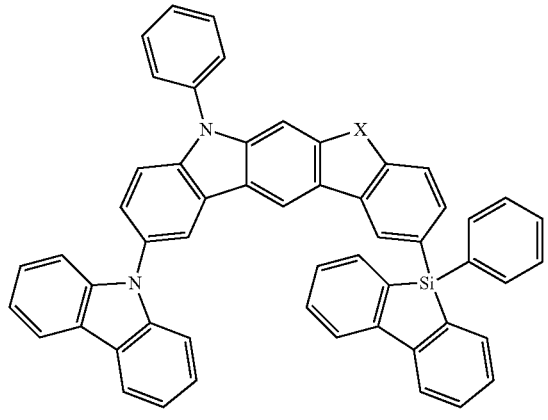
98
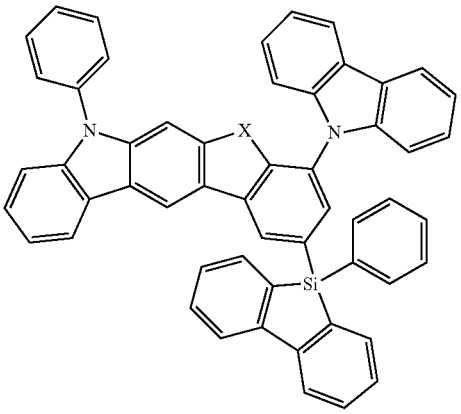
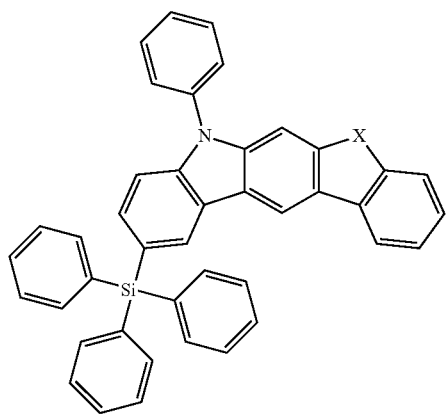
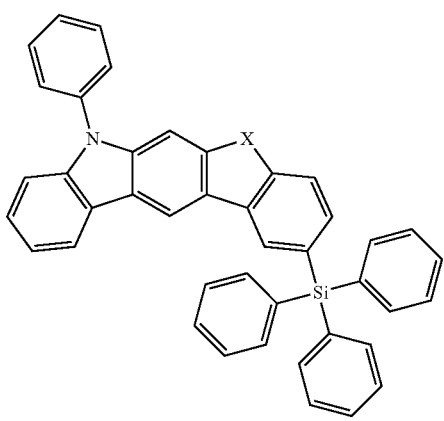
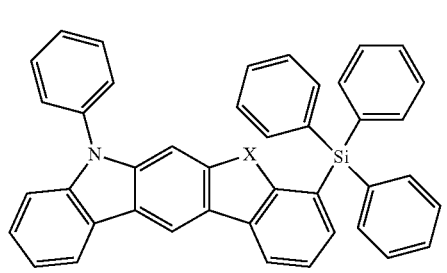
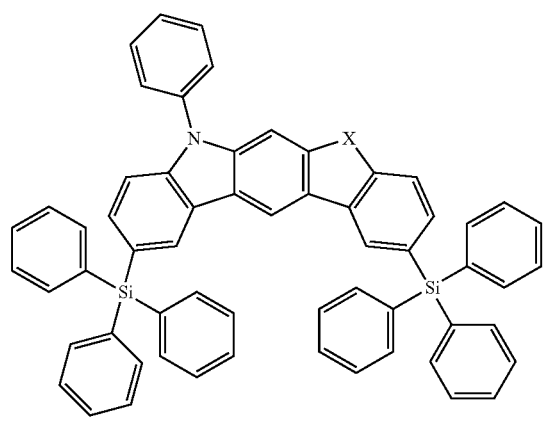

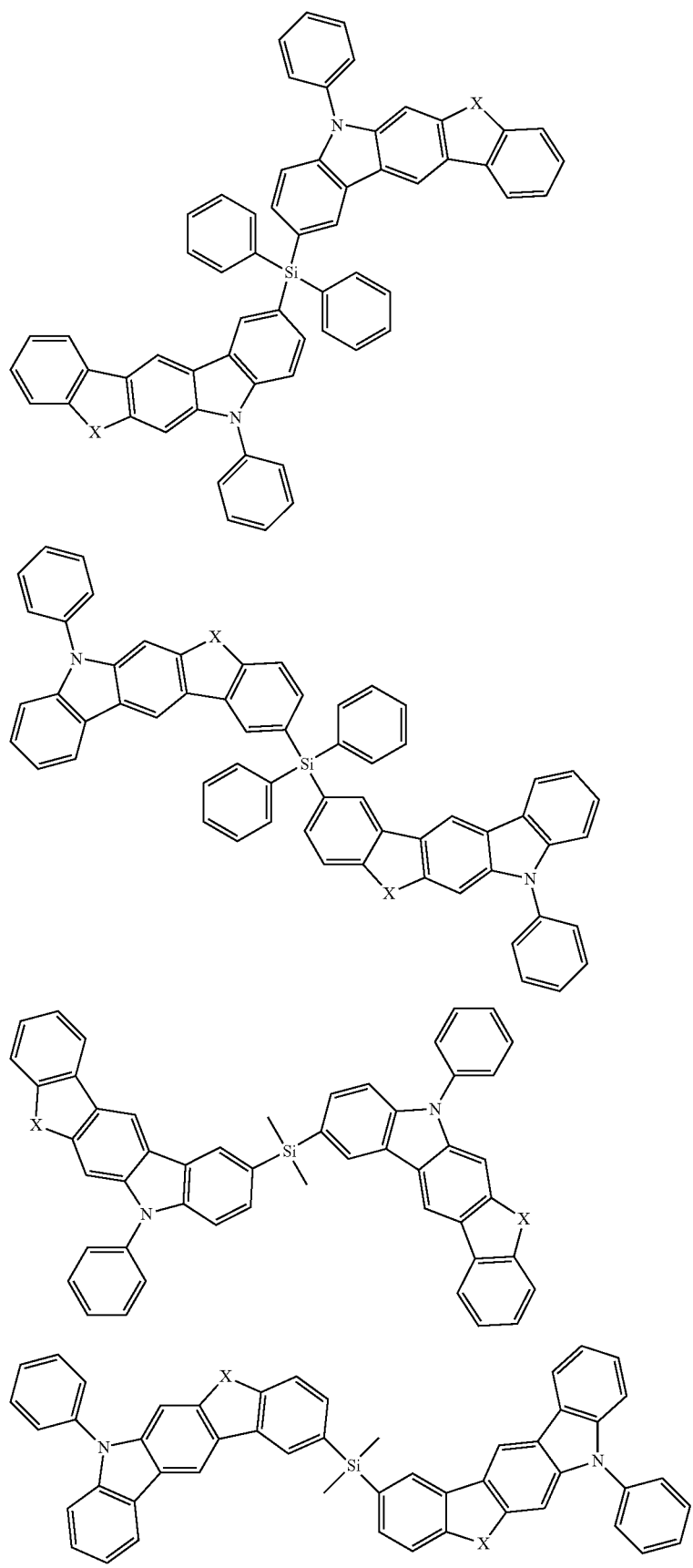

101                                                                                              102
-continued
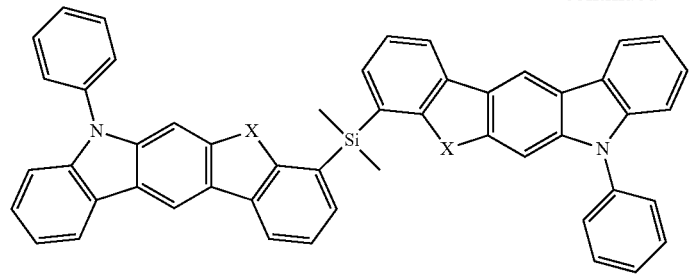
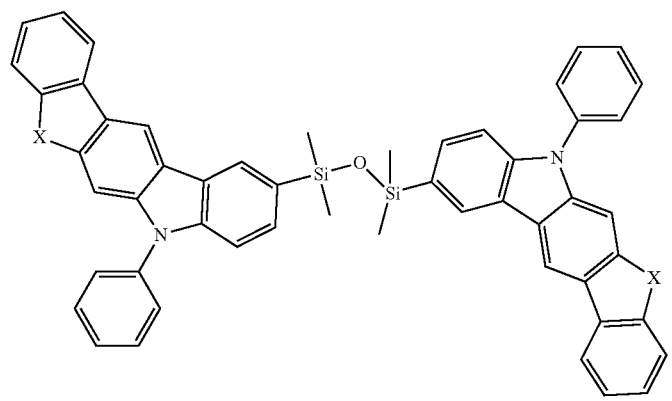
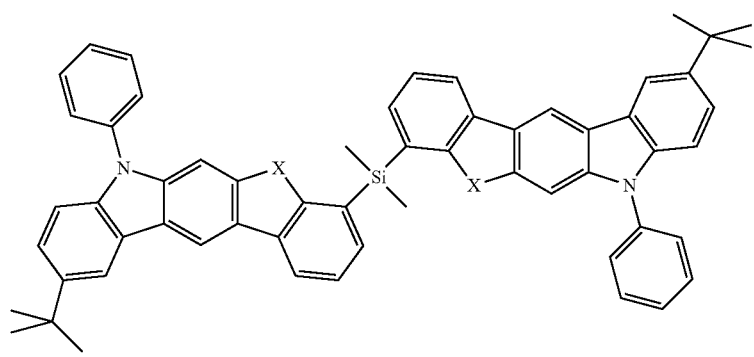
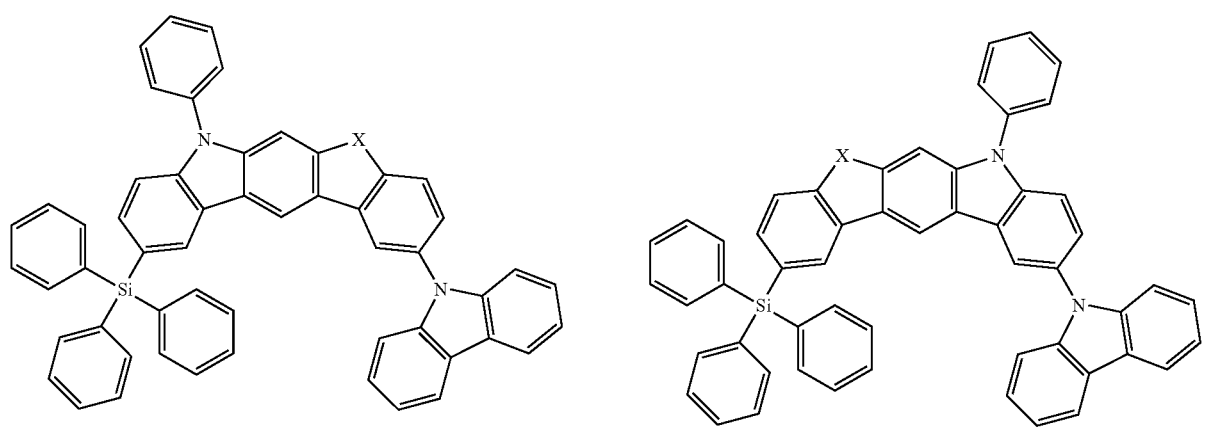

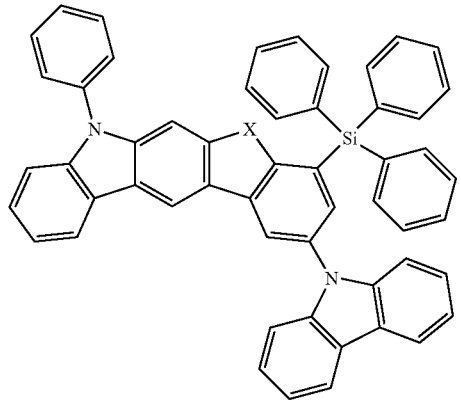
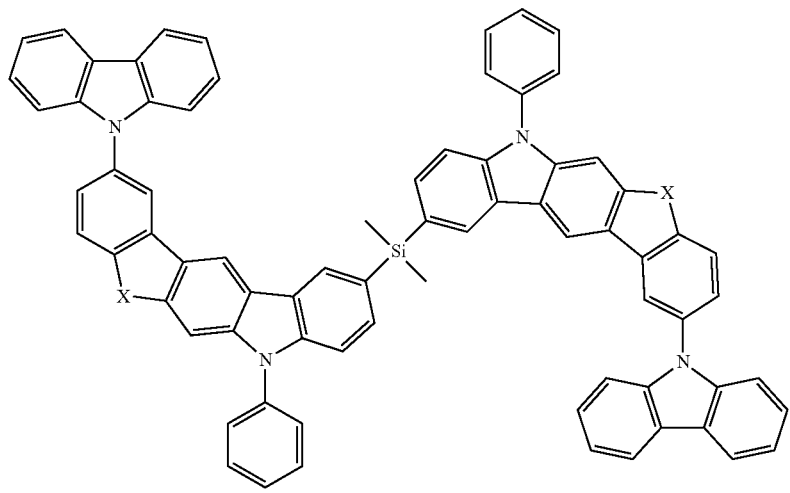
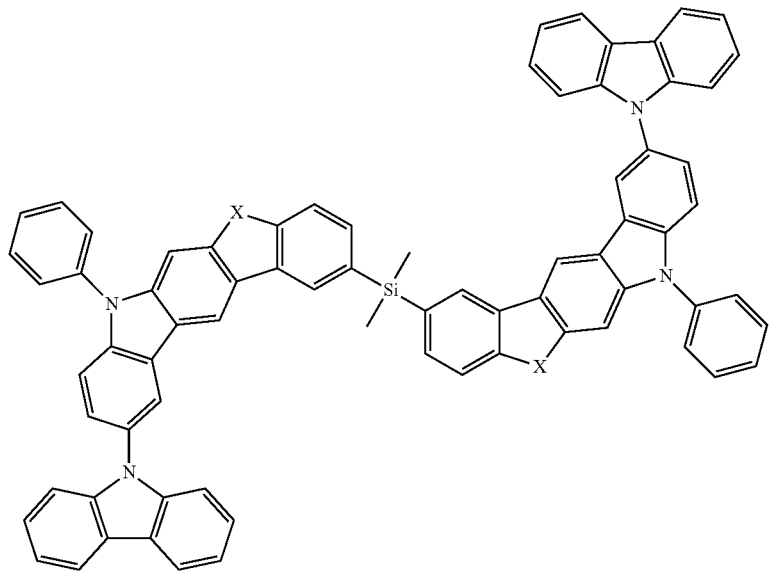

105
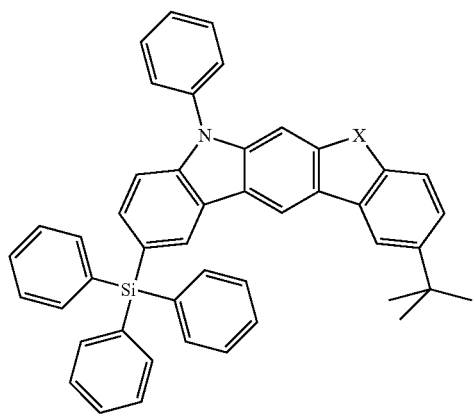
106
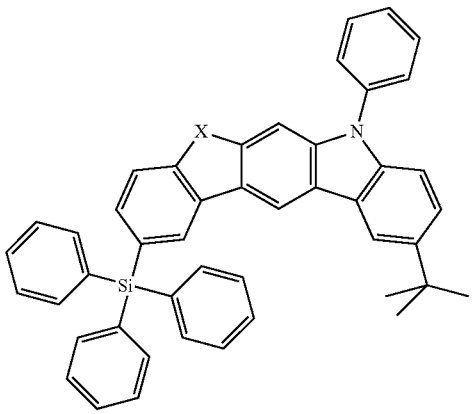
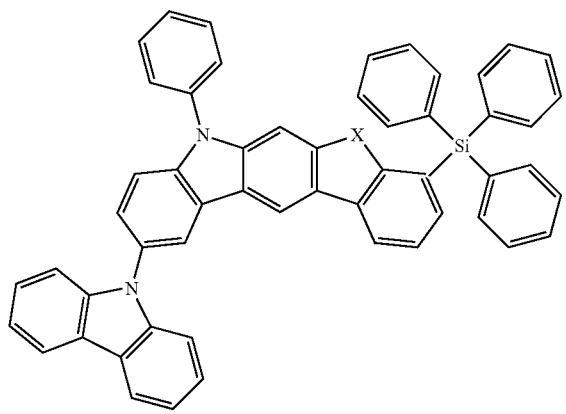
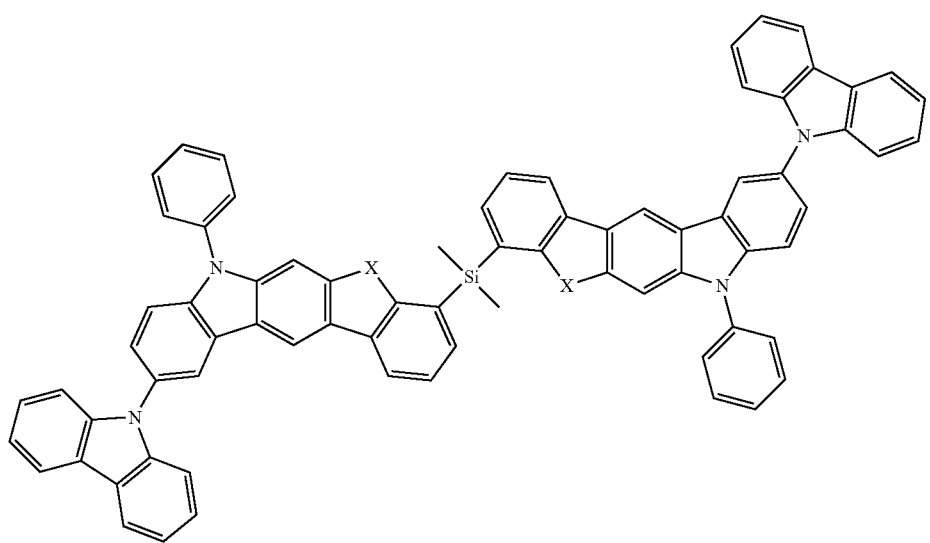

-continued

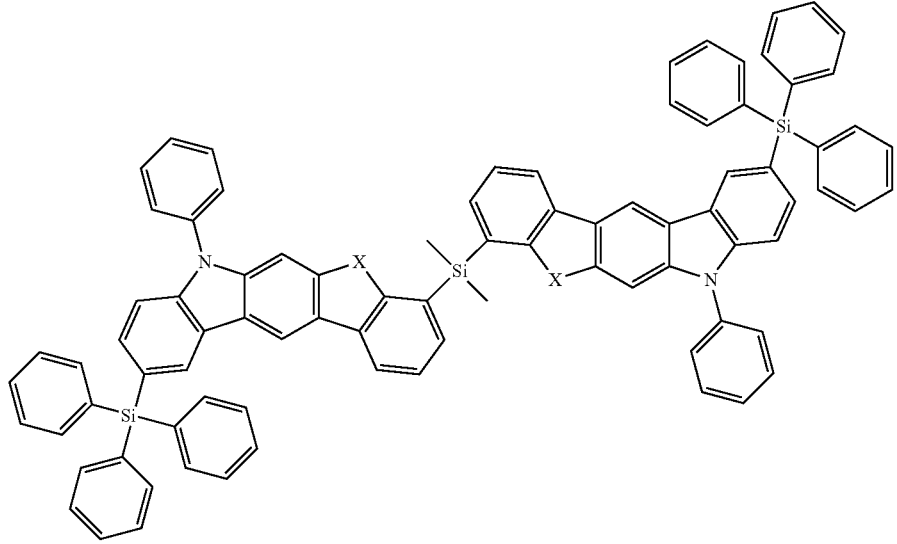

where X is O or S, preferably O.

The present application further provides carbazole derivatives of the general formula (I), (II) or (III)

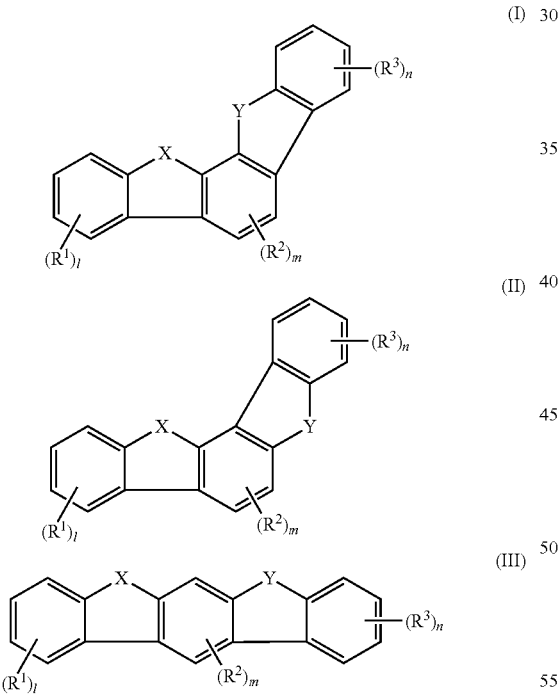

in which

X is $NR^4$, O or S, preferably $NR^4$ or O;

Y is $NR^5$, O or S, preferably $NR^5$ or O;

where at least one of the symbols X and Y is $NR^4$ or $NR^5$;

$R^1$ and $R^3$
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O(O$R^6$)), oxycarbonyl (—OC=O($R^6$)), thiocarbonyl (—SC=O($R^6$)), amino (—$NR^6R^7$), OH, pseudohalogen radicals, amido (—C=O($NR^6$)), —$NR^6$C=O($R^7$), phosphonate (—P(O)(O$R^6$)$_2$), phosphate (—OP(O)(O$R^6$)$_2$), phosphine (—P$R^6R^7$), phosphine oxide (—P(O)$R^6_2$), sulfate (—OS(O)$_2$O$R^6$), sulfoxide (—S(O)$R^6$), sulfonate (—S(O)$_2$O$R^6$), sulfonyl (—S(O)$_2R^6$), sulfonamide (—S(O)$_2NR^6R^7$), NO$_2$, boronic esters (—OB(O$R^6$)$_2$), imino (—C=$NR^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^1$ radicals or two adjacent $R^3$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the $R^1$ or $R^3$ radicals, in the case when it is arranged in the para position to X or Y, is bonded via a heteroatom selected from Si, Ge, O, S or P or via an sp$^3$-hybridized carbon atom;

$R^2$ is substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O(O$R^6$)), oxycarbonyl (—OC=O($R^6$)), thiocarbonyl (—SC=O($R^6$)), amino (—$NR^6R^7$), OH, pseudohalogen radicals, amido (—C=O($NR^6$)), —$NR^6$C=O($R^7$), phosphonate (—P(O)(O$R^6$)$_2$), phosphate (—OP(O)(OR$^6$)$_2$), phosphine (—PR$^6$R$^7$), phosphine oxide (—P(O)R$^6$$_2$), sulfate (—OS(O)$_2$OR$^6$), sulfoxide (—S(O)R$^6$), sulfonate (—S(O)$_2$OR$^6$), sulfonyl (—S(O)$_2$R$^6$), sulfonamide (—S(O)$_2$NR$^6$R$^7$), NO$_2$, boronic esters (—OB(OR$^6$)$_2$), imino (—C=NR$^6$R$^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R$^2$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

l, n are each independently 0, 1, 2, 3 or 4, where at least l or n is 1, 2, 3 or 4;

m is 0, 1 or 2;

R$^4$, R$^5$ are each independently substituted or unsubstituted C$_6$-C$_{30}$-aryl or substituted or unsubstituted C$_1$-C$_{20}$-alkyl;

R$^6$, R$^7$, R$^8$ are each independently substituted or unsubstituted C$_1$-C$_{20}$-alkyl or substituted or unsubstituted C$_6$-C$_{30}$-aryl, substituted or unsubstituted heteroaryl having 5 to 30 ring atoms, —O—Si(C$_1$-C$_{20}$-alkyl)$_3$, —O—Si(C$_6$-C$_{30}$-aryl)$_3$, C$_1$-C$_{20}$-alkoxy, C$_6$-C$_{30}$-aryloxy or halogenated C$_1$-C$_{20}$-alkyl radicals;

or two adjacent R$^6$ and R$^7$, R$^6$ and R$^8$ or R$^7$ and R$^8$ radicals, together with the atom to which they are bonded, form a ring having a total of 3 to 12 atoms, where the ring may be saturated or mono- or polyunsaturated and, as well as the atom to which the R$^6$, R$^7$ or R$^8$ radicals are bonded, may have exclusively carbon atoms or one or more further heteroatoms selected from N, O and P, where the ring may be unsubstituted or mono- or polysubstituted and/or may be fused to further 3- to 12-membered rings.

Preferred X, Y, R$^1$, R$^3$, R$^2$, l, n, m, R$^4$, R$^5$, R$^6$, R$^7$ and R$^8$ radicals and indices correspond to the aforementioned preferred X, Y, R$^1$, R$^3$, R$^2$, l, n, m, R$^4$, R$^5$, R$^6$, R$^7$ and R$^8$ radicals and indices.

More preferably, the at least one substituted carbazole derivative of the general formula (I), (II) or (III) has an R$^1$ substituent or an R$^3$ substituent arranged in the para position to X or Y, or both an R$^1$ substituent and an R$^3$ substituent each arranged in the para position to X or Y.

Particular preference is given to carbazole derivatives of the general formulae

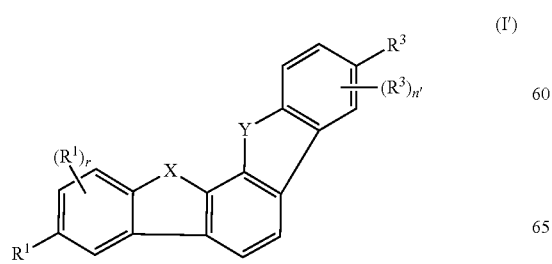
(I')

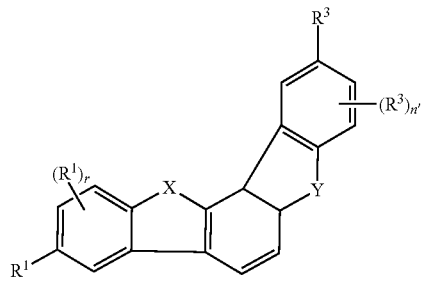
(II')

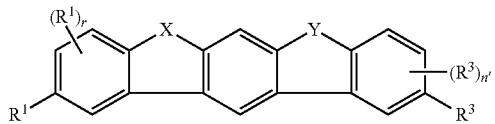
(III')

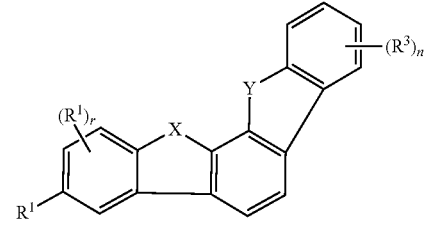
(I")

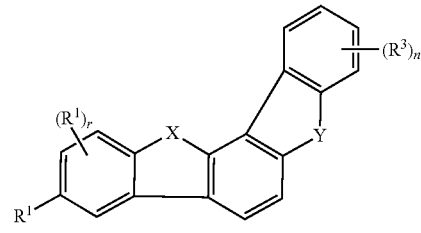
(II")

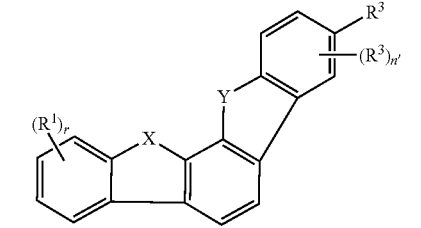
(III")

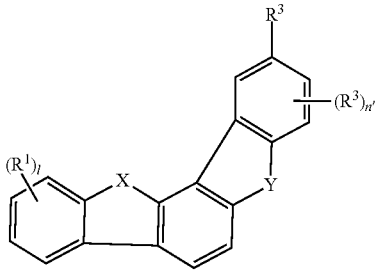
(I''')

(II''')

-continued

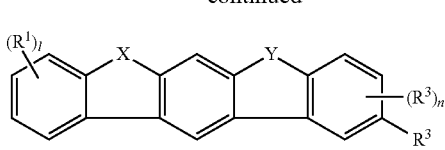
(III'''')

The X, Y, $R^1$, $R^3$, n and l radicals and indices in the compounds of the formulae (I'), (II'), (III'), (I"), (II"), (III"), (I'''), (II''') and (III''') are each as defined above. In a preferred embodiment, n and l are each 0. n' and l' in the compounds of the formulae (I'), (II'), (III'), (I"), (II"), (III"), (I'''), (II''') and (III''') are each independently 0, 1, 2 or 3, preferably 0 or 1, more preferably 0.

Examples of very particularly preferred carbazole derivatives of the formula (I), (II) or (III) are the aforementioned more preferably suitable benzofuranyl- and benzothiophenylcarbazoles mentioned by way of example.

In a preferred embodiment, the present application relates to benzofuranyl- and benzothiophenylcarbazoles of the general formula (I), (II) or (III)

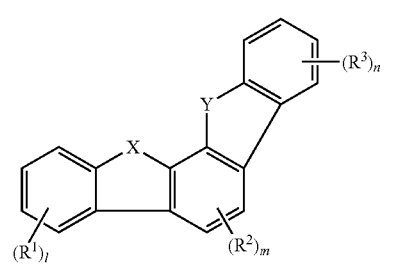
(I)

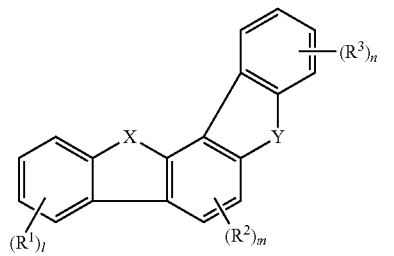
(II)

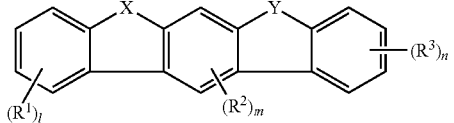
(III)

in which
X is $NR^4$, O or S, preferably $NR^4$ or O;
Y is $NR^5$, O or S, preferably $NR^5$ or O;
where one of the symbols X and Y is $NR^4$ or $NR^5$ and the other of the symbols X and Y is O or S, preferably O;
and the further symbols, radicals and indices are each as defined above.

Preferred benzofuranyl- and benzothiophenylcarbazoles correspond to the aforementioned preferred benzofuranyl- and benzothiophenylcarbazoles.

The compounds of the formulae (I), (II) and (III) can—in the case of the indolocarbazoles (X or Y is $NR^4$ or $NR^5$)—be prepared by the following process comprising steps (i), (ii) and (iii):

(i) preparation of a haloindolocarbazole, preferably of a dibromoindolocarbazole, by reacting 1,2-cyclohexadione, optionally substituted by one or more $R^2$ radicals, with halophenylhydrazine hydrochloride, preferably bromophenylhydrazine hydrochloride, in a Fischer indole synthesis by methods known to those skilled in the art; suitable $R^2$ radicals have been specified above;

(ii) introduction of the $R^4$ or $R^5$ radical at the appropriate nitrogen atoms.

The $R^4$ or $R^5$ radical is introduced by processes known to those skilled in the art.

The $R^4$ or $R^5$ radical is preferably introduced by reaction of the haloindolocarbazole obtained in step (i) with an alkyl halide or aryl halide or heteroaryl halide of the formula $R^4$-Hal or $R^5$-Hal, where $R^4$ and $R^5$ have each already been defined above and Hal is F, Cl, Br or I, preferably Br, I or F, more preferably I.

The $R^4$ or $R^5$ radical is generally introduced in the presence of a base. Suitable bases are known to those skilled in the art and are preferably selected from the group consisting of alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$ or Cs$_2$CO$_3$, and alkali metal alkoxides such as NaOMe, NaOEt. In addition, mixtures of the aforementioned bases are suitable. Particular preference is given to NaOH, KOH, NaH or K$_2$CO$_3$.

N-Alkylation (for example disclosed in M. Tosa et al., Heterocycl. Communications, Vol. 7, No. 3, 2001, p. 277-282) or N-arylation or N-heteroarylation (for example (N-arylation) disclosed in H. Gilman and D. A. Shirley, J. Am. Chem. Soc. 66 (1944) 888; D. Li et al., Dyes and Pigments 49 (2001) 181-186) is preferably performed in a solvent. Suitable solvents are, for example, polar aprotic solvents such as dimethyl sulfoxide, dimethylformamide or alcohols. It is likewise possible to use an excess of the alkyl halide or (hetero)aryl halide used as a solvent. The reaction can additionally be performed in a nonpolar aprotic solvent, for example toluene, when a phase transfer catalyst, for example tetra-n-butylammonium hydrogen sulfate, is present (as disclosed, for example, in I. Gozlan et al., J. Heterocycl. Chem. 21 (1984) 613-614).

The N-(hetero)arylation can be effected, for example, by copper-catalyzed coupling of the haloindolocarbazole obtained in step (i) with a (hetero)aryl halide, for example an aryl iodide (Ullmann reaction).

Preferably, the $R^4$ or $R^5$ radical is introduced by reaction of the haloindolocarbazole obtained in step (i) with an alkyl, aryl or heteroaryl fluoride in the presence of NaH in DMF (nucleophilic substitution) or by reaction with an alkyl, aryl or heteroaryl bromide or iodide under Cu/base (Ullmann, see above) or Pd catalysis.

The molar ratio of the haloindolocarbazole obtained in step (i) to the alkyl halide or (hetero)aryl halide of the formula $R^4$-Hal or $R^5$-Hal is generally 1:1 to 1:15, preferably 1:1 to 1:6, more preferably 1:4.

The N-alkylation or N-(hetero)arylation is performed generally at a temperature of from 0 to 220° C., preferably from 20 to 200° C. The reaction time is generally from 0.5 to 48 h, preferably from 1 to 24 h. In general, the N-alkylation or N-arylation is performed at standard pressure.

The resulting crude product is worked up by processes known to those skilled in the art.

(iii) Introduction of the $R^1$ or $R^3$ Radicals

The $R^1$ and $R^3$ radicals can, for example, be introduced by:
(iiia) halogen/metal exchange and subsequent silylation (in the case that $R^1$ or $R^3$ are silyl radicals); or (iiib) coupling.

(iiia): Halogen/Metal Exchange and Subsequent Silylation

Step (iiia) can be effected, in a first step, by halogen/metal exchange, by reaction of the haloindolocarbazole obtained in step (ii) with alkyllithium compounds or Mg at temperatures of generally −80° C. to +80° C., preferably at −40° C. to 30° C. (for alkyllithium compounds) or 0° C. to 80° C. (for Mg), more preferably of 0° C. to 40° C. (for Mg). Particular preference is given to using alkyllithium compounds, especially n-BuLi or tert-BuLi.

The reaction is generally effected in a solvent, preferably in THF or ethers, preferably diethyl ether. According to the invention, the synthesis yields are particularly good when diethyl ether is used as the solvent.

Therefore, the process for preparing the indolocarbazoles is preferably performed in such a way that the halogen-metal exchange on the haloindolocarbazole obtained in step (ii) is performed in diethyl ether as a solvent.

In a further embodiment, in step (iiia), the halogen/metal exchange is replaced by a metalation, preferably a lithiation, more preferably an ortho-lithiation. A lithiation, preferably an ortho-lithiation, is known per se to those skilled in the art, for example at a temperature of 100° C. to 25° C., preferably at −78° C. to RT, more preferably −40° C. to 0° C. The inventive metalation is preferably performed in an aprotic solvent, for example in THF. On completion of metalation, in a second step, the appropriate silane reagent is subsequently added in a solvent, for example in THF. This is explained in detail hereinafter.

In a directly subsequent second step, silylation is effected to give the compounds of the formula (I), (II) or (III), preferably by reaction with $SiR_mCl_{(4-m)}$ or $SiR_mH_{(4-m-n)}Cl_n$, where m is 0, 1, 2 or 3 and n is 0, 1, 2 and n+m is ≤3. The use of Si—H compounds is described in H. Gilman, W. J. Trepka *J. Org. Chem.* 1962, 27(4), 1418-1422. Si—H compounds are generally more stable than the chlorosilanes. The silylation is generally carried out in a solvent. Preferred solvents are THF or ethers, preferably diethyl ether. In general, the silylation is effected directly after the reaction in the first step, without workup or isolation of the product obtained after the first step.

(iiib): Coupling

The introduction of the $R^1$ or $R^3$ radicals can be performed by the processes specified for the introduction of the $R^4$ or $R^5$ radicals. In general, the $R^1$ or $R^3$ radicals are introduced in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. In addition, mixtures of the aforementioned bases are suitable. Particular preference is given to NaOH, KOH, NaH or $K_2CO_3$.

Heteroarylation can be effected, for example, by copper-catalyzed coupling of the $R^1$ or $R^3$ radicals with the haloindolocarbazole (Ullmann reaction).

The N-arylation was, for example, disclosed in H. Gilman and D. A. Shirley, J. Am. Chem. Soc. 66 (1944) 888; D. Li et al., Dyes and Pigments 49 (2001) 181-186. The reaction can be performed in solvent or in a melt. Suitable solvents are, for example, (polar) aprotic solvents such as dimethyl sulfoxide, dimethylformamide, NMP, tridecane or alcohols.

Preference is given to introducing the $R^1$ or $R^3$ radicals by conversion of the haloindolocarbazole in the presence of NaH in DMF (nucleophilic substitution) or by reaction under Cu/base (Ullmann, see above) or Pd catalysis conditions.

The N-alkylation or N-(hetero)arylation is performed generally at a temperature of from 0 to 220° C., preferably from 20 to 200° C. The reaction time is generally 0.5 to 76 h, preferably 1 to 48 h.

The resulting crude product is worked up by processes known to those skilled in the art.

Alternatively, it is also possible to perform additional halogenation steps on the desired compound of the formula (I), (II) or (III), followed by couplings and/or silylations, in order to introduce any further $R^1$ and $R^3$ radicals.

Substituents attached via phosphorus are introduced by means of a halogen/metal exchange, as described above, and a subsequent reaction with a chlorophosphine compound. When the target product is a phosphine oxide, subsequent oxidation is effected with, for example, $H_2O_2$ in water or mCPBA in $CH_2Cl_2$.

In a further embodiment, the $R^1$ and/or $R^3$ radicals can also be introduced on nonhalogenated indolocarbazoles by means of a Friedel-Crafts alkylation, especially in the cases when $R^1$ and/or $R^3$ are tert-butyl or fluorenyl. This means that, instead of the haloindolocarbazole prepared in step (i), a nonhalogenated indolocarbazole is used. The reaction conditions of the Friedel-Crafts alkylation are known to those skilled in the art. The alkylating reagents used may be alkyl halides, alcohols or alkenes, preference being given to alkyl halides, e.g. alkyl bromides or alkyl chlorides. The catalyst used is generally a Lewis acid, suitable Lewis acids being known to those skilled in the art. Suitable Lewis acids are zinc chloride, zinc bromide, aluminum chloride, aluminum bromide, iron(III)chloride and iron(III)bromide. In addition, it is possible to use Eaton's reagent ($P_2O_5$ in methanesulfonic acid), phosphoric acid, sulfuric acid, hydrogen fluoride and mercury(II) sulfate as catalysts. Zinc chloride and aluminum chloride are preferred. The fluorenylation is preferably performed with fluoroenols, which are reacted, for example, with the strong acid Eaton's reagent ($P_2O_5$ in methanesulfonic acid).

Further processes for preparing the compounds of the formulae (I), (II) and (III) can be performed in an analogous manner to the processes specified in the synthesis examples A1 to A8.

The compounds of the formulae (I), (II) and (III) in which X or Y is $PR^4$ or $PR^5$ and the further X or Y group in each case is $NR^4$ or $NR^5$, and the compounds of the formulae (I), (II) and (III) in which X and Y are each $PR^4$ and $PR^5$, can be prepared in an analogous manner to the indolocarbazoles.

The inventive benzofuranyl- and benzothiophenylcarbazoles of the formulae (I), (II) and (III) can be prepared, for example, by the following process:

(i) preparation of a halogenated benzofuranyl- or benzothiophenylindole;

(ii) preparation of a halogenated benzofuranyl- or benzothiophenylcarbazole proceeding from the benzofuranyl- or benzothiophenylindole prepared in step (i);

(iii) nitrogen substitution of the halogenated benzofuranyl- or benzothiophenylcarbazole prepared in step (ii);

(iv) introduction of the $R^1$ or $R^3$ radical(s) to prepare the compounds of the formula (I), (II) or (III).

A general process scheme is detailed hereinafter, where X in the compounds of the formula (I), (II) or (III) is O or S, preferably O, and Y is $NR^5$. It is possible in an analogous manner to prepare compounds of the formula (I), (II) or (III) in which X is $NR^4$ and Y is O or S, preferably O. The process scheme shows, by way of example, the preparation of compounds of the formula (I). The compounds of the formulae (II) and (III) can be prepared in an analogous manner. Examples for preparation of compounds of the formulae (II) and (III) are given in the Examples section of the present application.

Step (i)

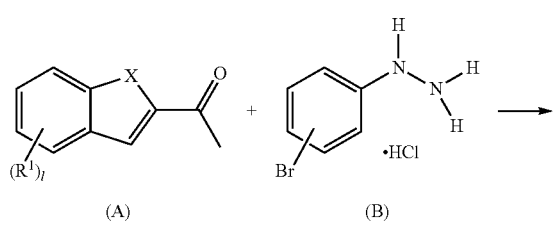

Step (ii)

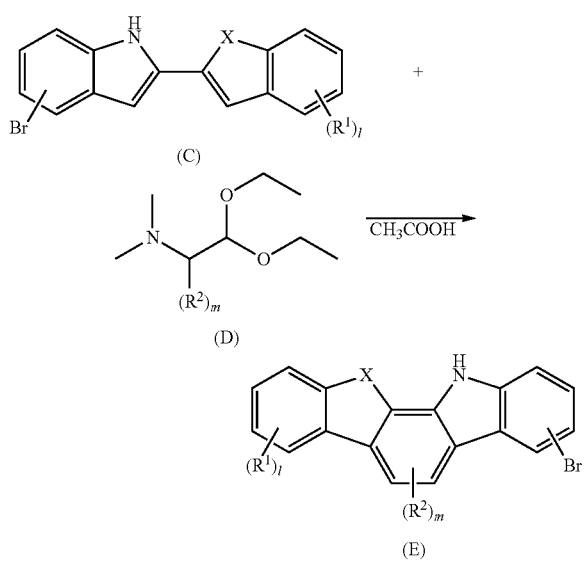

Step (iii)

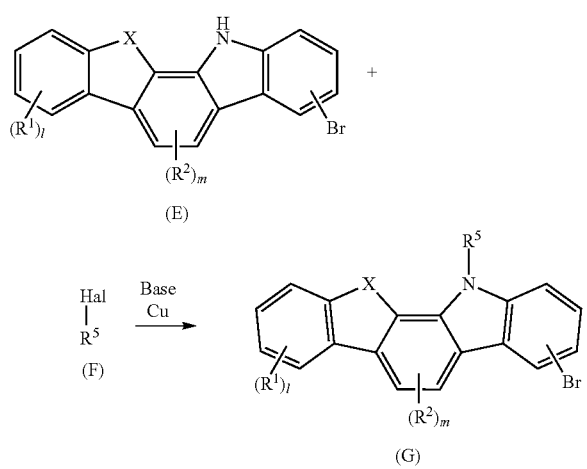

Step (iv)

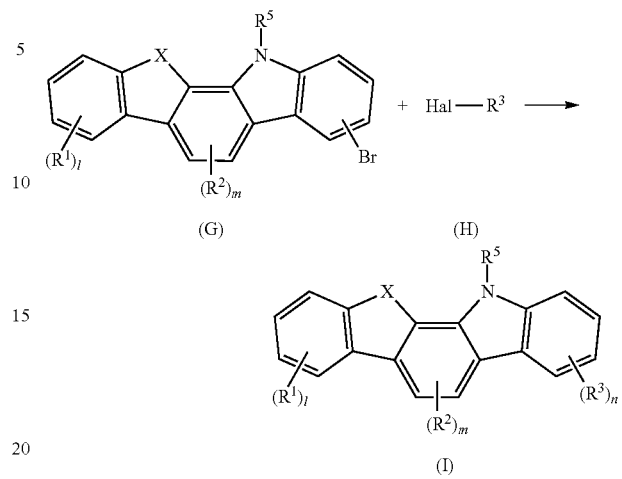

Step (i)

In step (i), 2-acetylbenzofuran or 2-acetylbenzothiophene optionally substituted by one or more $R^1$ radicals is reacted with halophenylhydrazine hydrochloride, preferably bromophenylhydrazine hydrochloride, in a Fischer indole synthesis by processes known to those skilled in the art; suitable $R^1$ radicals have been specified above.

Step (ii)

In step (ii), the compound (C) obtained in step (i) is bridged with an acetal (D) optionally substituted by an $R^2$ radical. Suitable $R^2$ radicals have been specified above. The bridging can be performed, for example, by dissolving the compound (C) in acetic acid under reflux and then adding the acetal (D). The acetal (D) is preferably added in a molar excess in relation to compound (C). For example, the molar ratio of compound (C) to the acetal (D) is 1:1.1-20, preferably 1:2-15, more preferably 1:5-12. The workup is effected by processes known to those skilled in the art.

Similar processes for preparing indolocarbazoles by bridging with an acetal are disclosed, for example, in Tetrahedron Letters 47, 2006, 6385-6388 and Tetrahedron 1999, 2371-2380.

Alternatively, the compound (C) obtained in step (i) can be bridged with an acetylene (D'), in an analogous manner to the process described in J. Am. Chem. Soc. 2008, 130, 15823-15835

Step (iii): Nitrogen Substitution of the Halogenated Benzofuranyl- or Benzothiophenylcarbazole Prepared in Step (ii)

The $R^5$ radical is introduced by processes known to those skilled in the art.

The radical is preferably introduced by reaction of the compound (E) obtained in step (ii) with an alkyl halide or aryl halide or heteroaryl halide of the formula $R^5$-Hal (F), where $R^5$ has already been defined above and Hal is F, Cl, Br or I, preferably Br, I or F, more preferably I.

The $R^5$ radical is generally introduced in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as NaNH$_2$, alkali metal or alkaline earth metal carbonates such as K$_2$CO$_3$ or Cs$_2$CO$_3$, and alkali metal alkoxides such as NaOMe, NaOEt. In addition, mixtures of the aforementioned bases are suitable. Particular preference is given to NaOH, KOH, NaH or K$_2$CO$_3$.

N-Alkylation (for example disclosed in M. Tosa et al., Heterocycl. Communications, Vol. 7, No. 3, 2001, p. 277-282) or N-arylation or N-heteroarylation (for example (N-arylation) disclosed in H. Gilman and D. A. Shirley, J. Am. Chem. Soc. 66 (1944) 888; D. Li et al., Dyes and Pigments 49 (2001) 181-186) is preferably performed in a solvent. Suitable solvents are, for example, polar aprotic solvents such as dimethyl sulfoxide, dimethylformamide or alcohols. It is likewise possible to use an excess of the alkyl halide or (hetero)aryl halide used as a solvent. The reaction can additionally be performed in a nonpolar aprotic solvent, for example toluene, when a phase transfer catalyst, for example tetra-n-butylammonium hydrogen sulfate, is present (as disclosed, for example, in I. Gozlan et al., J. Heterocycl. Chem. 21 (1984) 613-614).

The N-(hetero)arylation can be effected, for example, by copper-catalyzed coupling of the compound (E) obtained in step (ii) with a (hetero)aryl halide, for example an aryl iodide (Ullmann reaction).

The R$^5$ radical is preferably introduced by reaction of the compound (E) obtained in step (ii) with an alkyl, aryl or heteroaryl fluoride in the presence of NaH in DMF (nucleophilic substitution) or by reaction with an alkyl, aryl or heteroaryl bromide or alkyl, aryl or heteroaryl iodide under Cu/base (Ullmann, see above) or Pd catalysis.

The molar ratio of the compound (E) obtained in step (ii) to the alkyl halide or (hetero)aryl halide of the formula R$^5$-Hal is generally 1:1 to 1:15, preferably 1:1 to 1:6, more preferably 1:4.

The N-alkylation or N-(hetero)arylation is performed generally at a temperature of from 0 to 220° C., preferably 20 to 200° C. The reaction time is generally 0.5 to 48 h, preferably 1 to 24 h. In general, the N-alkylation or N-arylation is performed at standard pressure.

The resulting crude product is worked up by processes known to those skilled in the art.

(iv) Introduction of the R$^3$ Radical:

The R$^3$ radical can, for example, be introduced by:
(iva) halogen/metal exchange and subsequent silylation (in the case that R$^3$ is a silyl radical); or
(ivb) coupling.

(iva): Halogen/Metal Exchange and Subsequent Silylation

Step (iva) can be effected, in a first step, by halogen/metal exchange, by reaction of the compound (G) obtained in step (iii) with alkyllithium compounds or Mg at temperatures of generally −80° C. to +80° C., preferably at −40° C. to 30° C. (for alkyllithium compounds) or 0° C. to 80° C. (for Mg), more preferably of 0° C. to 40° C. (for Mg). Particular preference is given to using alkyllithium compounds, especially n-BuLi or tert-BuLi.

The reaction is generally effected in a solvent, preferably in THF or ethers, preferably diethyl ether. According to the invention, the synthesis yields are particularly good when diethyl ether is used as the solvent.

The present invention therefore preferably relates to the process according to the invention wherein a halogen-metal exchange is carried out on the compound (G) obtained in step (iii) in diethyl ether as a solvent.

In a further embodiment, in step (iva), the halogen/metal exchange is replaced by a metalation, preferably a lithiation, more preferably an ortho-lithiation. A lithiation, preferably an ortho-lithiation, is known per se to those skilled in the art, for example at a temperature of 100° C. to 25° C., preferably at −78° C. to RT, more preferably −40° C. to 0° C. The inventive metalation is preferably performed in an aprotic solvent, for example in THF. On completion of metalation, in a second step, the appropriate silane reagent is subsequently added in a solvent, for example in THF. This is explained in detail hereinafter.

In a directly subsequent second step, silylation is effected to give the compounds of the formula (I), (II) or (III), preferably by reaction with SiR$_m$Cl$_{(4-m)}$ or SiR$_m$H$_{(4-m-n)}$Cl$_n$, where m is 0, 1, 2 or 3 and n is 0, 1, 2 and n+m is ≤3. The use of Si—H compounds is described in H. Gilman, W. J. Trepka J. Org. Chem. 1962, 27(4), 1418-1422. Si—H compounds are generally more stable than the chlorosilanes. The silylation is generally carried out in a solvent. Preferred solvents are THF or ethers, preferably diethyl ether. In general, the silylation is effected directly after the reaction in the first step, without workup or isolation of the product obtained after the first step.

(ivb): Coupling

The introduction of the R$^3$ radical can be performed by the processes specified for the introduction of the R$^5$ radical. In general, the R$^3$ radical is introduced in the presence of a base. Suitable bases are known to those skilled in the art and are preferably selected from the group consisting of alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$ or Cs$_2$CO$_3$, and alkali metal alkoxides such as NaOMe, NaOEt. In addition, mixtures of the aforementioned bases are suitable. Particular preference is given to NaOH, KOH, NaH or K$_2$CO$_3$.

Heteroarylation can be effected, for example, by copper-catalyzed coupling of the R$^3$ radical with the haloindolocarbazole (Ullmann reaction).

The N-arylation was, for example, disclosed in H. Gilman and D. A. Shirley, J. Am. Chem. Soc. 66 (1944) 888; D. Li et al., Dyes and Pigments 49 (2001) 181-186. The reaction can be performed in solvent or in a melt. Suitable solvents are, for example, (polar) aprotic solvents such as dimethyl sulfoxide, dimethylformamide, NMP, tridecane or alcohols. It is likewise possible to use an excess of the haloindolocarbazole as a solvent.

The R$^3$ radical is preferably introduced by conversion of the haloindolocarbazole in the presence of NaH in DMF (nucleophilic substitution) or by reaction under Cu/base (Ullmann, see above) or Pd catalysis conditions.

The N-alkylation or N-(hetero)arylation is performed generally at a temperature of 0 to 220° C., preferably 20 to 200° C. The reaction time is generally 0.5 to 76 h, preferably 1 to 48 h.

The resulting crude product is worked up by processes known to those skilled in the art.

Alternatively, it is also possible to perform additional halogenation steps on the desired compound of the formula (I), (II) or (III), followed by couplings and/or silylations, in order to introduce any further R$^1$ and R$^3$ radicals.

In a further embodiment, the R$^3$ radical can also be introduced on nonhalogenated benzofuranyl- and benzothiophenylcarbazoles by means of a Friedel-Crafts alkylation, especially in the cases when R$^3$ is tert-butyl or fluorenyl. This means that, instead of the halogenated benzofuranyl- and benzothiophenylcarbazole prepared in steps (i) and (ii), a nonhalogenated benzofuranyl- and benzothiophenylcarbazole is used. The reaction conditions of the Friedel-Crafts alkylation are known to those skilled in the art. The alkylating reagents used may be alkyl halides, alcohols or alkenes, preference being given to alkyl halides, e.g. alkyl bromides or alkyl chlorides. The catalyst used is generally a Lewis acid, suitable Lewis acids being known to those skilled in the art. Suitable Lewis acids are zinc chloride, zinc bromide, aluminum chloride, aluminum bromide, iron(III)chloride and iron(III)bromide. In addition, it is possible to use Eaton's reagent ($P_2O_5$ in methanesulfonic acid), phosphoric acid, sulfuric acid, hydrogen fluoride and mercury(II)sulfate as catalysts. Zinc chloride and aluminum chloride are preferred. The fluorenylation is preferably performed with fluoroenols, which are reacted, for example, with the strong acid Eaton's reagent ($P_2O_5$ in methanesulfonic acid).

The present application thus further provides a process for preparing benzofuranyl- and benzothiophenylcarbazoles of the formulae (I), (II) and (III), comprising the steps of:
 (i) preparation of a halogenated benzofuranyl- or benzothiophenylindole;
 (ii) preparation of a halogenated benzofuranyl- or benzothiophenylcarbazole proceeding from the benzofuranyl- or benzothiophenylindole prepared in step (i);
 (iii) nitrogen substitution of the halogenated benzofuranyl- or benzothiophenylcarbazole prepared in step (ii);
 (iv) introduction of the $R^1$ or $R^3$ radical(s) to prepare the compounds of the formula (I), (II) or (III).

Suitable structures of the organic electronics applications are known to those skilled in the art and are specified below.

The organic transistor generally includes a semiconductor layer formed from an organic layer with hole transport capacity and/or electron transport capacity; a gate electrode formed from a conductive layer; and an insulation layer introduced between the semiconductor layer and the conductive layer. A source electrode and a drain electrode are mounted on this arrangement in order thus to produce the transistor element. In addition, further layers known to those skilled in the art may be present in the organic transistor. The compounds of the formula (I), (II) or (III) may be present in any desired layer of the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor character or hole transport capacity, and a layer formed with n-type semiconductor character or electron transport capacity. In addition, it is possible for further layers known to those skilled in the art to be present in the organic solar cell. The compounds of the formula (I), (II) or (III) may be present in any desired layer of the organic solar cell.

In a further embodiment, the present invention relates to an organic light-emitting diode comprising at least one compound of the formula (I), (II) or (III). The compounds of the formula (I), (II) or (III) can be used in the organic light-emitting diode as matrix material and/or hole/exciton blocker material and/or electron/exciton blocker material and/or hole injection material and/or electron injection material and/or hole conductor material and/or electron conductor material, preferably as matrix material and/or hole/exciton blocker material. The indolocarbazoles covered by the compounds of the formulae (I), (II) and (III) can additionally also preferably be used as hole conductors and electron/exciton blockers.

In a preferred embodiment of the invention, compounds of the general formula (I), (II) or (III) are used in a mixture, for example together with another hole conductor or electron conductor in the hole-conducting or electron-conducting layer. Further hole conductors or electron conductors used may generally be materials known to those skilled in the art, especially the hole conductors or electron conductors mentioned below.

In a further embodiment, the present invention relates to an organic light-emitting diode in which the compounds of the formula (I), (II) or (III) are used as electron/exciton blockers, preferably in a blocking layer for electrons, as hole conductors or in the light-emitting layer, preferably as matrix material.

It is likewise possible that the compounds of the formula (I), (II) or (III) are present both in the light-emitting layer (preferably as matrix material) and in the blocking layer for electrons (as electron/exciton blockers).

The inventive benzofuranyl- and benzothiophenylcarbazoles of the formula (I), (II) or (III) may additionally be present as hole/exciton blocker in a blocking layer for holes.

The present invention further provides an organic light-emitting diode comprising an anode An and a cathode Ka and a light-emitting layer E arranged between the anode An and the cathode Ka, and optionally at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula (I), (II) or (III) is present in the light-emitting layer E and/or in at least one of the further layers. The at least one compound of the formula (I), (II) or (III) is preferably present in the light-emitting layer and/or the blocking layer for electrons and/or the hole conductor layer.

The inventive benzofuranyl- and benzothiophenylcarbazoles of the formula (I), (II) or (III) may additionally be present as hole/exciton blocker in a blocking layer for holes.

The present application further relates to a light-emitting layer comprising at least one compound of the formula (I), (II) or (III).

The present invention further relates to an OLED comprising an inventive light-emitting layer.

The present invention further relates to a blocking layer for electrons/excitons comprising at least one compound of the formula (I), (II) or (III).

The present invention further relates to a blocking layer for holes/excitons comprising at least one inventive benzofuranyl- or benzothiophenylcarbazole of the formula (I), (II) or (III).

Structure of the Inventive OLED

The inventive organic light-emitting diode (OLED) thus generally has the following structure:
an anode (An) and a cathode (Ka) and a light-emitting layer E arranged between the anode (An) and the cathode (Ka).

The inventive OLED may, for example—in a preferred embodiment—be formed from the following layers:
 1. anode
 2. hole conductor layer
 3. light-emitting layer
 4. blocking layer for holes/excitons
 5. electron conductor layer
 6. cathode Layer sequences different from the aforementioned construction are also possible, and are known to those skilled in the art. For example, it is possible that the OLED does not have all of the layers mentioned; for example, an OLED with the layers (1) (anode), (3) (light-emitting layer) and (6) (cathode) are likewise suitable, in which case the functions of the layers (2) (hole conductor layer) and (4) (blocking layer for holes/excitons) and (5) (electron conductor layer) are assumed by the adjoining layers. OLEDs which have layers (1), (2), (3) and (6), or layers (1), (3), (4), (5) and (6), are likewise suitable. In addition, the OLEDs may have a blocking layer for electrons/excitons between the anode (1) and the hole conductor layer (2).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the Periodic Table of the Elements (old IUPAC version) are used, for example indium tin oxide (ITO). It is likewise possible that the anode (1) comprises an organic material, for example polyaniline, as described, for example, in Nature, vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, vol. 18, pages 837 to 860, 1996. Both hole-transporting molecules and polymers can be used as hole transport material. Hole-transporting molecules typically used are selected from the group consisting of tris[N-(1-naphthyl)-N-(phenylamino)]triphenylamine(1-NaphDATA), 4,4'-bis[N-(1-naphthyl)-N-phenylamino]biphenyl (α-NPD), N,N'-diphenyl-N,N'-bis(3-methylphenyl)-[1,1-biphenyl]-4,4'-diamine (TPD), 1,1-bis[(di-4-tolylamino)-phenyl]cyclohexane (TAPC), N,N'-bis(4-methylphenyl)-N,N'-bis(4-ethylphenyl)[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl)](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenyiamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (spiro-TPD), N,N'-bis(naphthalen-1-yl)-N,N'-bis(phenyl)-9,9-spirobifluorene (spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris(N-(2-naphthyl)-N-phenylamino)triphenylamine, pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-spiro-TPD), 2,2'-bis[N,N-bis(4-methoxyphenyl)amino]-9,9-spirobifluorene (2,2'-MeO-spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NPBAPF), 2,2',7,7'-tetrakis[N-naphthalenyl(phenyl)amino]-9,9'-spirobifluorene (spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (spiro-5), 2,2'-bis[N,N-bis(biphenyl-4-yl)amino]-9,9-spirobifluorene (2,2'-spiro-DBP), 2,2'-bis(N,N-diphenylamino)-9,9-spirobifluorene (spiro-BPA), 2,2',7,7'-tetra(N,N-ditolyl)aminospirobifluorene (spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole conductor materials, the band gap of the at least one hole conductor material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/113704, WO 2007/115970, WO 2007/115981 and WO 2008/000727. One example of a suitable carbene complex is Ir(dpbic)$_3$ with the formula:

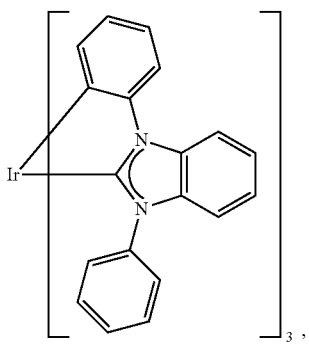

which is disclosed, for example, in WO2005/019373. In principle, it is possible that the hole conductor layer comprises at least one compound of the formula (I), (II) or (III) as a hole conductor material.

It is likewise possible to use mixtures in the hole-transporting (hole-conducting) layer, in particular mixtures which lead to electrical p-doping of the hole-transporting layer. p-Doping is achieved by the addition of oxidizing materials. These mixtures may, for example, be mixtures of the abovementioned hole transport materials with $MoO_2$, $MoO_3$, $WO_x$, $ReO_3$, $V_2O_5$, 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquinodimethane, 2,5-difluoro-7,7,8,8-tetracyanoquinodimethane, dicyanomethylene-(1,3,4,5,7,8-hexafluoro-6H-naphthalen-2-ylidene)malononitrile ($F_6$-TNAP), Mo(tfd)$_3$ (from Kahn et al., J. Am. Chem. Soc. 2009, 131 (35), 12530-12531), and with quinone compounds as mentioned in EP 09153776.1.

The light-emitting layer (3) comprises at least one emitter material. This may in principle be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula (I), (II) or (III) can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981 and WO 2008/000727.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)(pyridinato-N,C$^{3'}$)(acetylacetonate), tris(2-phenylquinoline)iridium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato)iridium(III), iridium(III) bis(dibenzo[f,h]quinoxaline)-(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-ylpyridine)(acetylacetonato)iridium(III).

In addition, the following commercially available materials are suitable: tris(dibenzoylacetonato)mono(phenanthroline)europium(III), tris(dibenzoylmethane)-mono(phenanthroline)europium(III), tris(dibenzoylmethane)mono(5-aminophenanthroline)europium(III), tris(di-2-naphthoylmethane)mono(phenanthroline)europium(III), tris(4-bromobenzoylmethane)mono(phenanthroline)europium (III), tris(di(biphenyl)-methane)mono(phenanthroline)europium(III), tris(dibenzoylmethane)mono(4,7-diphenylphenanthroline)europium(III), tris(dibenzoylmethane)mono(4,7-dimethylphenanthroline)europium(III), tris(dibenzoylmethane)mono(4,7-dimethylphenanthrolinedisulfonic acid)europium(III) disodium salt, tris[di(4-(2-(2-ethoxyethoxy)ethoxy)-benzoylmethane)]mono(phenanthroline)europium(III) and tris [di[4-(2-(2-ethoxyethoxy)ethoxy)benzoylmethane]]mono (5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole)-dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)pyrazolato) dimethylphenylphosphine, tris[4,4'-di-tert-butyl(2,2') bipyridine]-ruthenium(III), osmium(II) bis(2-(9,9-dibutylfluorenyl)-1-isoquinoline)(acetylacetonate).

Suitable triplet emitters are, for example, carbene complexes. In one embodiment of the present invention, the compounds of the formula (I), (II) or (III) are used in the light-emitting layer as a matrix material together with carbene complexes as triplet emitters. Suitable carbene complexes are, for example, carbene complexes of the general formula (IV)

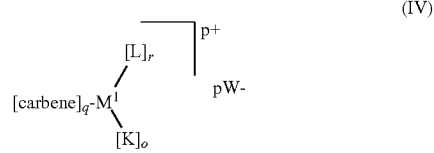

in which the symbols are each defined as follows:
M$^1$ is a metal atom selected from the group consisting of metals of group IB, IIB, IIIB, IVB, VB, VIB, VIIB, the lanthanides and IIIA of the Periodic Table of the Elements (CAS version) in any oxidation state possible for the particular metal atom;

carbene is a carbene ligand which may be uncharged or monoanionic and mono-, bi- or tridentate; the carbene ligand may also be a bis- or triscarbene ligand;

L is a mono- or dianionic ligand, preferably monoanionic ligand, which may be mono- or bidentate;

K is an uncharged mono- or bidentate ligand;

q is the number of carbene ligands, where n is at least 1 and the carbene ligands in the complex of the formula I when q>1 may be the same or different;

r is the number of ligands L, where m may be 0 or ≥1, and the ligands L when r>1 may be the same or different;

o is the number of ligands K, where o may be 0 or ≥1, and the ligands K, when o>1, may be the same or different;

p is the charge of the complex: 0, 1, 2, 3 or 4; preferably 0, 1 or 2, more preferably 0;

W is a monoanionic counterion;

where the sum of q+r+o and the charge p depends on the oxidation state and coordination number of the metal atom used, the charge of the complex and the denticity of the carbene, L and K ligands, and on the charge of the carbene and L ligands, with the condition that n is at least 1.

The present invention therefore further provides an organic light-emitting diode in which the emitter material used in the light-emitting layer is at least one carbene complex of the general formula (IV).

Suitable carbene complexes of the formula (IV) are known to those skilled in the art and are described, for example, in WO 2005/019373 A2, WO 2006/056418 A2, WO 2005/113704, WO 2007/115970, WO 2007/115981 and WO 2008/000727.

Further suitable carbene complexes are described in the not pre-published applications having the reference numbers EP 10 187 176.2 and U.S. 61/391,712.

Said carbene complexes are carbene complexes oft the general formula

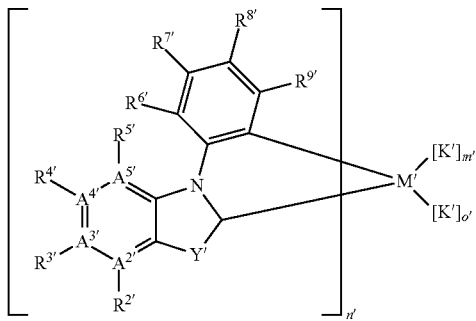

wherein M', n', Y', A$^{2'}$, A$^{3'}$, A$^{4'}$, A$^{5'}$, R$^{1'}$, R$^{2'}$, R$^{3'}$, R$^{4'}$, R$^{5'}$, R$^{6'}$, R$^{7'}$, R$^{8'}$, R$^{9'}$, R$^{10'}$, K', L', m' and o' are defined as follows:

M' is Ir or Pt, n' is an integer selected from 1, 2 or 3,

Y' is NR$^{1'}$, O, S or C(R$^{10'}$)$_2$,

A$^{2'}$, A$^{3'}$,

A$^{4'}$, A$^{5'}$ are independently of each other N or C, wherein 2 A' are=N-atoms and between two N-atoms in the ring at least one C-atom is present, R$^{1'}$ is a linear or branched alkyl residue having from 1 to 20 carbon atoms, which is optionally interrupted by at least one heteroatom and optionally bears at least one functional group, a cycloalkyl residue having from 3 to 20 carbon atoms, a substituted or unsubstituted aryl residue having from 6 to 30 carbon atoms, a substituted or unsubstituted heteroaryl residue having a total of from 5 to 18 carbon atoms and/or heteroatoms,

R$^{2'}$, R$^{3'}$,

R$^{4'}$, R$^{5'}$ are, if A$^{2'}$, A$^{3'}$, A$^{4'}$ and/or A$^{5'}$ are N, a free electron pair or, if A$^{2'}$, A$^{3'}$, A$^{4'}$ and/or A$^{5'}$ are C, independently of each other hydrogen, a linear or branched alkyl residue having from 1 to 20 carbon atoms, which is optionally interrupted by at least one heteroatom and optionally bears at least one functional group, a cycloalkyl residue having from 3 to 20 carbon atoms, a substituted or unsubstituted aryl residue having from 6 bis 30 carbon atoms, a substituted or unsubstituted heteroaryl residue having a total of from 5 to 18 carbon atoms and/or heteroatoms, a group having donor or acceptor action, or R$^{3'}$ and R$^{4'}$ form together with A$^{3'}$ and A$^{4'}$ an unsaturated ring having a total of from 5 to 18 carbon atoms and/or heteroatoms, which is optionally interrupted by at least one further heteroatom and optionally substituted,

R$^{6'}$, R$^{7'}$,

R$^{8'}$, R$^{9'}$ are independently of each other hydrogen, a linear or branched alkyl residue having from 1 to 20 carbon atoms, which is optionally interrupted by at least one heteroatom and optionally bears at least one functional group, a cycloalkyl residue having from 3 to 20 carbon atoms, a cycloheteroalkyl residue having from 3 to 20 carbon atoms, a substituted or unsubstituted aryl residue having from 6 bis 30 carbon atoms, a substituted or unsubstituted heteroaryl residue having a total of from 5 to 18 carbon atoms and/or heteroatoms, a group having donor or acceptor action, or R$^{6'}$ and R$^{7'}$, R$^{7'}$ and R$^{8'}$ or R$^{8'}$ and R$^{9'}$ form together with the C-atoms to which R$^{6'}$, R$^{7'}$, R$^{8'}$ and R$^{9'}$ are linked, an unsaturated ring having a total of from 5 to 18 carbon atoms and/or heteroatoms, which is optionally interrupted by at least one further heteroatom and is optionally substituted, and/or if A$^{5'}$ is C, R$^{5'}$ and R$^{6'}$ together form a bridge comprising a total of from 1 to 30 carbon atoms and/or heteroatoms which is optionally annulated with a substituted or unsubstituted five to eight membered carbon atoms and/or heteroatoms comprising ring, which bridge is saturated or unsaturated, linear or branched, optionally comprises heteroatoms, an aromatic unit, a heteroaromatic unit and/or functional groups, R$^{10'}$ is a linear or branched alkyl residue having from 1 to 20 carbon atoms, which is optionally interrupted by at least one heteroatom and optionally bears at least one functional group, a cycloalkyl residue having from 3 to 20 carbon atoms, a substituted or unsubstituted aryl residue having from 6 to 30 carbon atoms, a substituted or unsubstituted heteroaryl residue having a total of from 5 to 18 carbon atoms and/or heteroatoms, K' is an uncharged mono- or bidentate ligand, L' is a mono- or dianionic ligand, preferably a monoanionic ligand, which may be mono- or bidentate, m' is 0, 1 or 2, and the ligands K', when m is 2, may be the same or different, o' is 0, 1 or 2, and the ligands L', when o is 2, may be the same or different.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, likewise be a small molecule, for example 4,4'-N,N'-dicarbazolebiphenyl (CDP=CBP) or tertiary aromatic amines, for example TCTA. In a preferred embodiment of the present invention, at least one compound of the formula (I), (II) or (III) is used as matrix material.

In a preferred embodiment, the light-emitting layer is formed from 2 to 30% by weight, preferably 5 to 20% by weight, of at least one of the aforementioned emitter materials and 70 to 98% by weight, preferably 80 to 95% by weight, of at least one of the aforementioned matrix materials—in one embodiment at least one compound of the formula (I), (II) or (III)—where the sum total of the emitter material and of the matrix material adds up to 100% by weight.

In a further embodiment, the compounds of the formula (I), (II) or (III) are used as hole/exciton blocker material, preferably together with carbene complexes as triplet emitters. The compounds of the formula (I), (II) or (III) may additionally—as mentioned above—be used as matrix materials or both as matrix materials and as hole/exciton blocker materials together with carbene complexes as triplet emitters. In addition, it is possible that at least one compound of the formula (I), (II) or (III) is present in a blocking layer for holes/excitons, a blocking layer for electrons/excitons, a hole injection layer, a hole conductor layer, an electron injection layer and/or an electron conductor layer of the OLED, preferably together with carbene complexes as triplet emitters.

Suitable metal complexes for use together with the compounds of the formula (I), (II) or (III) as matrix material and/or hole/exciton blocker material and/or electron/exciton blocker material and/or hole injection material and/or electron injection material and/or hole conductor material and/or electron conductor material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727, as well as in the not pre-published applications having the reference numbers EP 10 187 176.2 and U.S. 61/391,712. Explicit reference is made here to the disclosure of the WO applications cited, and these disclosures shall be considered to be incorporated into the content of the present application.

If the blocking layer for holes/excitons (4) does not comprise any compounds of the formula (I), (II) or (III), the OLED has—if a blocking layer for holes is present—hole blocker materials typically used in OLEDs, such as 2,6-bis (N-carbazolyl)pyridine (mCPy), 2,9-dimethyl-4,7-diphenyl-1,10-phenanthroline (bathocuproin, (BCP)), bis(2-methyl-8-quinolinato)-4-(phenylphenylato)aluminum(III) (BAlq), phenothiazine S,S-dioxide derivatives and 1,3,5-tris(N-phenyl-2-benzylimidazolyl)benzene (TPBI), TPBI also being suitable as electron-conducting material. Further suitable hole blockers and/or electron conductor materials are 2,2',2"-(1,3,5-benzenetriyl)tris(1-phenyl-1H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazol-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazol-2-yl]-2,2'-bipyridyl, 2-phenyl-9,10-di (naphthalen-2-yl)anthracene, 2,7-bis[2-(2,2'-bipyridin-6-yl)-1,3,4-oxadiazol-5-yl]-9,9-dimethylfluorene, 1,3-bis[2-(4-tert-butylphenyl)-1,3,4-oxadiazol-5-yl]benzene, 2-(naphthalen-2-yl)-4,7-diphenyl-1,10-phenanthroline, tris (2,4,6-trimethyl-3-(pyridin-3-yl)phenyl)borane, 2,9-bis (naphthalen-2-yl)-4,7-diphenyl-1,10-phenanthroline, 1-methyl-2-(4-(naphthalen-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO 2009/003919 and WO 2009/000872, and disilyl compounds as disclosed in WO2008/034758, as a blocking layer for holes/excitons (4) or as matrix materials in the light-emitting layer (3).

The blocking layer for holes of the inventive OLED may comprise, for example, at least one compound of the general formula (V)

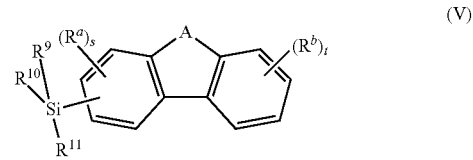

in which:
A is $NR^{12}$, S, O;
$R^{12}$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms;
$R^9$, $R^{10}$, $R^{11}$
are each independently substituted or unsubstituted $C_1$-$C_{20}$-alkyl or substituted or unsubstituted $C_6$-$C_{30}$-aryl or a structure of the general formula (a)

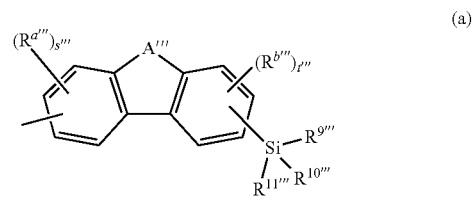

$R^a$, $R^b$
are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^{12}R^{13}R^{14}$, halogen radicals, halogenated $C_1$-$C_{20}$-alkyl radicals, carbonyl (—CO($R^{12}$)), carbonylthio (—C=O($SR^{12}$)), carbonyloxy (—C=O($OR^{12}$)), oxycarbonyl (—OC=O($R^{12}$)), thiocarbonyl (—SC=O($R^{12}$)), amino (—$NR^{12}R^{13}$), OH, pseudohalogen radicals, amido (—C=O($NR^{12}$)), —$NR^{12}$C=O($R^{13}$), phosphonate (—P(O)($OR^{12}$)$_2$), phosphate (—OP (O)($OR^{12}$)$_2$), phosphine (—$PR^{12}R^{13}$), phosphine oxide (—P(O)$R^{12}{}_2$), sulfate (—OS(O)$_2OR^{12}$), sulfoxide (—S(O)R$^{12}$), sulfonate (—S(O)$_2$OR$^{12}$), sulfonyl (—S(O)$_2$R$^{12}$), sulfonamide (—S(O)$_2$NR$^{12}$R$^{13}$), NO$_2$, boronic esters (—OB(OR$^{12}$)$_2$), imino (—C=NR$^{12}$R$^{13}$), borane radicals, stannane radicals, hydrazine radicals, hydrazone radicals, oxime radicals, nitroso groups, diazo groups, vinyl groups, sulfoximines, alanes, germanes, boroximes and borazines;

R$^{12}$, R$^{13}$, R$^{14}$
  are each independently substituted or unsubstituted C$_1$-C$_{20}$-alkyl, or substituted or unsubstituted C$_6$-C$_{30}$-aryl;

s, t are each independently 0, 1, 2 or 3; where, in the case when q or r is 0, all substitutable positions of the aryl radical are substituted by hydrogen, where the radicals and indices in the group of the formula (a) A''', R$^{9'''}$, R$^{10'''}$, R$^{11'''}$, R$^{a'''}$, R$^{b'''}$, s''' and t''' are each independently as defined for the radicals and indices of the compounds of the general formula (V) A, R$^9$, R$^{10}$, R$^{11}$, R$^a$, s and t.

Processes for preparing the compounds of the formula (V) are known to those skilled in the art and are disclosed, for example, in PCT application PCT/EP2009/067120 and the following PCT applications: WO 2009/003919 and WO 2009/003898.

The present application thus further provides an organic light-emitting diode which comprises, as at least one further layer, a blocking layer for holes, said blocking layer for holes comprising at least one compound of the general formula (V).

In a preferred embodiment, the present invention relates to an inventive OLED comprising the layers (1) anode, (2) hole conductor layer, (3) light-emitting layer, (4) blocking layer for holes/excitons, (5) electron conductor layer and (6) cathode, and optionally further layers, wherein the blocking layer for holes/excitons or the light-emitting layer comprises at least one compound of the formula (I), (II) or (III). In addition, the OLED, in a further preferred embodiment, comprises a hole injection layer (1a), which is generally arranged between the anode (1) and the hole conductor layer (2). Suitable materials for the hole injection layer are known to those skilled in the art.

Suitable electron conductor materials for layer (5) of the inventive OLEDs comprise metals chelated to oxinoid compounds, such as 2,2',2''-(1,3,5-phenylene)tris[1-phenyl-1H-benzimidazole] (TPBI), tris(8-quinolinolato)aluminum (Alq$_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)-aluminum (BAlq), 1,3-bis[2-(2,2'-bipyridin-6-yl)-1,3,4-oxadiazol-5-yl]benzene (Bpy-OXD), 6,6'-bis[5-(biphenyl-4-yl)-1,3,4-oxadiazol-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazol-5-yl]-9,9-dimethylfluorene (Bby-FOXD), 1,3-bis[2-(4-tert-butylphenyl)-1,3,4-oxadiazol-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HNBphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, BCP is used as the electron conductor material. In principle, it is possible that the electron conductor layer comprises at least one compound of the formula (I), (II) or (III) as an electron conductor material.

It is likewise possible to use mixtures of at least two materials in the electron-transporting (electron-conducting) layer, in which case at least one material is electron-conducting. Preferably, in such mixed electron-transporting layers, at least one phenanthroline compound is used. More preferably, in mixed electron-transporting layers, alkali metal hydroxyquinolate complexes, for example Liq, are used in addition to at least one phenanthroline compound. Furthermore, it is possible to use mixtures which lead to electrical n-doping of the electron-transporting layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, Cs$_2$CO$_3$, with alkali metal complexes, for example 8-hydroxyquinolatolithium (Liq), and with Y, Ce, Sm, Gd, Tb, Er, Tm, Yb, Li$_3$N, Rb$_2$CO$_3$, dipotassium phthalate, W(hpp)$_4$ from EP 1786050 or with compounds as described in EP1837926 B1.

The present invention therefore also relates to an inventive OLED which comprises an electron-transporting layer comprising at least two different materials, at least one material of which should be electron-conducting.

In a preferred embodiment, the present invention relates to an inventive OLED wherein the electron-transporting layer comprises at least one phenanthroline derivative.

In a further preferred embodiment, the invention relates to an inventive OLED wherein the electron-transporting layer comprises at least one phenanthroline derivative and at least one alkali metal hydroxyquinolate complex.

In a further preferred embodiment, the invention relates to an inventive OLED wherein the electron-transporting layer comprises at least one phenanthroline derivative and 8-hydroxyquinolatolithium.

Among the materials mentioned above as hole conductor materials and electron conductor materials, some may fulfil several functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. p-Doping is achieved by the addition of oxidizing materials. These mixtures may, for example, be mixtures of the abovementioned hole transport materials with MoO$_2$, MoO$_3$, WO$_x$, ReO$_3$, V$_2$O$_5$, 7,7,8,8-tetracyanoquinodimethane (TCNQ), 2,3,5,6-tetrafluoro-7,7,8,8-tetracyanoquinodimethane (F$_4$-TCNQ), 2,5-bis(2-hydroxyethoxy)-7,7,8,8-tetracyanoquinodimethane, bis(tetra-n-butylammonium) tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquinodimethane, 2,5-difluoro-7,7,8,8-tetracyanoquinodimethane, dicyanomethylene-(1,3,4,5,7,8-hexafluoro-6H-naphthalen-2-ylidene)malononitrile (F$_6$-TNAP), Mo(tfd)$_3$ (from Kahn et al., J. Am. Chem. Soc. 2009, 131 (35), 12530-12531), and with quinone compounds as mentioned in EP 09153776.1.

The electron conductor materials can be doped, for example, with alkali metals, for example Alq$_3$ with lithium. In addition, electron conductors can be doped with salts such as Cs$_2$CO$_3$. Electronic doping is known to those skilled in the art and is disclosed, for example, in W. Gao, A. Kahn, J. Appl. Phys., vol. 94, No. 1, Jul. 1, 2003 (p-doped organic layers); A. G. Werner, F. Li, K. Harada, M. Pfeiffer, T. Fritz, K. Leo. Appl. Phys. Lett., vol. 82, No. 25, Jun. 23, 2003 and Pfeiffer et al., Organic Electronics 2003, 4, 89-103. For example, the hole conductor layer can be doped a, in addition to a carbene complex, e.g. Ir(dpbic)$_3$, with MoO$_3$ or WO$_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the Periodic Table of the Elements (old IUPAC version), comprising the lanthanides and actinides, for example samarium. In addition, it is also possible to use metals such as aluminum or indium, and combinations of all metals mentioned. In addition, lithium-comprising organometallic compounds or LiF can be applied between the organic layer and the cathode in order to reduce the operating voltage.

The OLED according to the present invention may additionally comprise further layers which are known to those skilled in the art. For example, between the layer (2) and the light-emitting layer (3) may be applied a layer which facilitates the transport of the positive charge and/or matches the band gap of the layers to one another. Alternatively, this further layer may serve as a protective layer. In an analogous manner, additional layers may be present between the light-emitting layer (3) and the layer (4) in order to facilitate the transport of the negative charge and/or to match the band gap between the layers to one another. Alternatively, this layer may serve as a protective layer.

In a preferred embodiment, the inventive OLED, in addition to layers (1) to (6), comprises at least one of the further layers mentioned below:
a hole injection layer between the anode (1) and the hole-transporting layer (2);
a blocking layer for electrons between the hole-transporting layer (2) and the light-emitting layer (3);
an electron injection layer between the electron-transporting layer (5) and the cathode (6).

Materials for a hole injection layer may be selected from copper phthalocyanine, 4,4',4''-tris(N-3-methylphenyl-N-phenylamino)triphenylamine (m-MTDATA), 4,4',4''-tris-(N-(2-naphthyl)-N-phenylamino)triphenylamine (2T-NATA), 4,4',4''-tris(N-(1-naphthyl)-N-phenylamino)triphenylamine (1T-NATA), 4,4',4''-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), PEDOT-PSS polymer. In principle, it is possible that the hole injection layer comprises at least one compound of the formula (I), (II) or (III) as a hole injection material.

The material selected for the electron injection layer may, for example, be LiF, CsF or Cs$_2$CO$_3$. In principle, it is possible that the electron injection layer comprises at least one compound of the formula (I), (II) or (III) as an electron injection material.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

Use of the compounds of the formula (I), (II) or (III) in at least one layer of the OLED, preferably in the light-emitting layer (preferably as matrix material) and/or in the blocking layer for holes/excitons makes it possible to obtain OLEDs with high efficiency and with low use and operating voltage. Frequently, the OLEDs obtained by the use of the compounds of the formula (I), (II) or (III) additionally have high lifetimes. The inventive carbazole derivatives and those used in accordance with the invention conduct holes and electrons, i.e. they are bipolar. This can establish a good charge carrier balance, which can achieve better efficiencies and lifetimes. The efficiency of the OLEDs can additionally be improved by optimizing the other layers of the OLEDs. For example, it is possible to use high-efficiency cathodes such as Ca or Ba, optionally in combination with an intermediate layer of LiF, CsF or $Cs_2CO_3$. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; garments; furniture; wallpaper.

In addition, the compounds of the formula (I), (II) or (III) can be used in OLEDs with inverse structure. The compounds of the formula (I), (II) or (III) used in accordance with the invention are preferably used in these inverse OLEDs again as hole/exciton blocker materials. The structure of inverse OLEDs and the materials typically used therein are known to those skilled in the art.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; garments; furniture; wallpaper comprising at least one inventive organic light-emitting diode or at least one inventive light-emitting layer.

In a preferred embodiment, the inventive carbazole derivatives of the formulae (I), (II) and (III) and those used in accordance with the invention can be used in white OLEDs, preferably as matrix material in a light-emitting layer or as blocker material. In the Examples section which follows, corresponding embodiments and examples are adduced in section C.

The examples which follow provide additional illustration of the invention.

EXAMPLES

A Indolocarbazoles

Synthesis Examples

Synthesis Example A1

Synthesis of 3,8-dibromo-11H,12H-indolo[2,3-a]carbazole (compound 1 (Fischer indole synthesis))

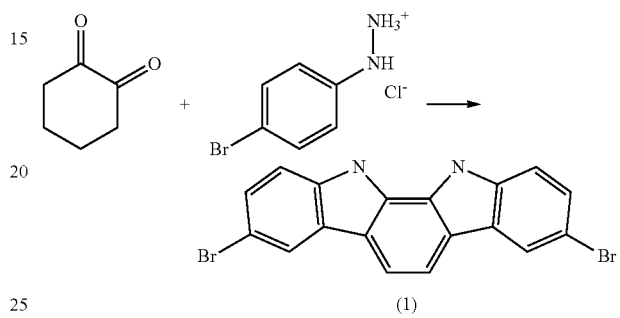

4-Bromophenylhydrazine hydrochloride (99%; 10.44 g, 1 eq) is introduced into a solution of 1,2-cyclohexadione (98%; 5.4 g, 1 eq) in absolute ethanol (50 ml). After adding 20 drops of glacial acetic acid, the mixture is stirred at room temperature for 1 h and then at 80° C. for 4 h. Then a further 5.3 g of 99% 4-bromophenylhydrazine hydrochloride are added to the reaction and, after a further 6 h at 80° C., another 5.3 g of 99% 4-bromophenylhydrazine hydrochloride are added. The reaction is stirred overnight. After 22 h, the mixture becomes viscous, so 150 ml of absolute ethanol and a further 3 g of 99% 4-bromophenylhydrazine hydrochloride are added. After a further 2 h at 80° C., the mixture is worked up. For this purpose, the solvent is distilled off. The residue is introduced gradually into polyphosphoric acid (50 g), heated to 120° C. and stirred for 1 h. The reaction output is added cautiously to ice-water and neutralized with 2M NaOH. The precipitate is filtered off and washed with distilled water. The residue is dried under reduced pressure. After recrystallization in glacial acetic acid, 5.8 g are obtained. Yield: 29.7%

$^1$H NMR (CO($CD_3$)$_2$, 400 MHz):

δ=10.58 (br s, 2H), 8.30 (s, 2H), 7.98 (s, 2H), 7.54 (br, 2H), 7.45 (br, 2H).

Synthesis Example A2

Synthesis of 3,8-dibromo-11,12-diphenyl-11H,12H-indolo[2,3-a]carbazole (compound 2)

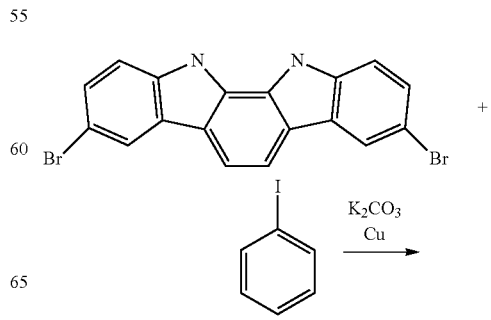

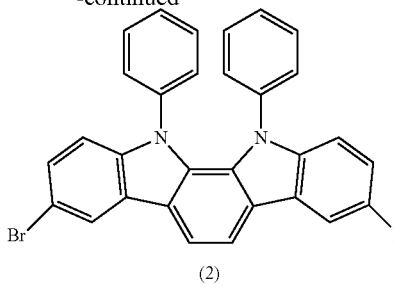

Compound 1 (2.0 g, 1 eq.) is combined with iodobenzene (98%; 30 g, 8 eq.), potassium carbonate (6.43 g, 2.5 eq.) and copper powder (2.36 g, 2 eq.) and heated to 145° C. The reaction is stirred at 145° C. for 48 h. The mixture is cooled to room temperature and diluted with methylene chloride, filtered and washed. The filtrate is diluted with n-hexane. The methylene chloride is distilled off on a rotary evaporator. The precipitated solid is filtered and washed with n-hexane. The residue is precipitated repeatedly in hexane, then dried under reduced pressure overnight. Final weight 5.12 g (48.6% yield)

$^1$H NMR (CD$_2$Cl$_2$, 400 MHz): δ=8.29 (s, 2H), 8.07 (s, 2H), 7.38 (d, 2H), 7.08-7.15 (m, 8H), 6.72 (d, 4H).

Synthesis Example A3

Synthesis of 11,12-diphenyl-3,8-bis(triphenylsilyl)-11H,12H-indolo[2,3-a]carbazole (compound 3)

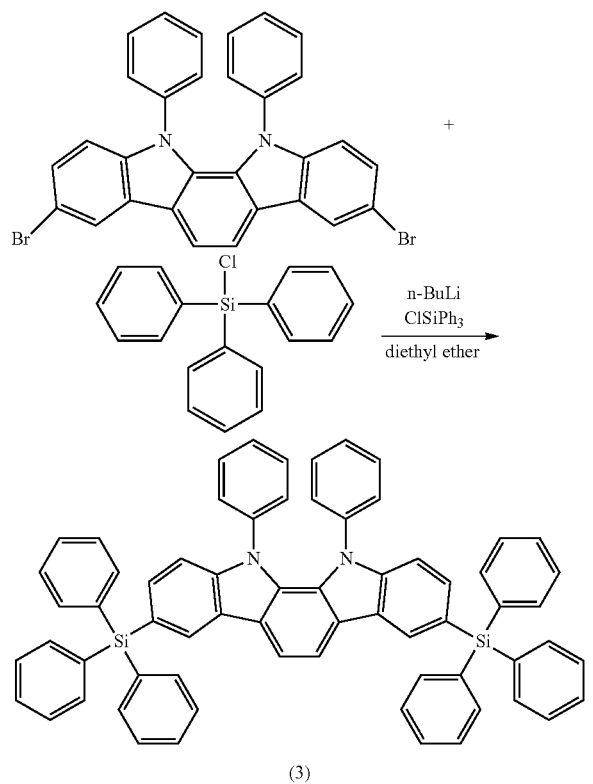

n-Butyllithium (1.6 M in hexane, 4.6 ml, 2.1 eq.) is slowly added dropwise at room temperature under nitrogen to a suspension of compound 2 (2.0 g, 1 eq.) in ultradry diethyl ether (55 ml) and the mixture is stirred at room temperature for a further 2 h. A solution of chlorotriphenylsilane (97%; 3.22 g, 3 eq.) in ultradry diethyl ether (20 ml) is slowly added dropwise to the reaction. The reaction is stirred at reflux overnight. After 22 h, the experiment is cooled to room temperature and 20 ml of methanol is added. The reaction is transferred to a separating funnel with methylene chloride and washed with distilled water (3×50 ml). Organic phase dried with sodium sulfate, concentrated and dried at 65° C. under reduced pressure. LC (SiO$_2$, 3:7 CH$_2$Cl$_2$/cyclohexane) gives 1.12 g of compound 3 (36.7% yield).

$^1$H NMR (CD$_2$Cl$_2$, 400 MHz): δ=8.37 (s, 2H), 7.97 (s, 2H), 7.63 (d, 12H), 7.36-7.50 (m, 20H), 7.29 (d, 2H), 7.08-7.14 (m, 6H) 6.78 (d, 4H).

Synthesis Example A4

Synthesis of 11,12-diphenyl-11H,12H-indolo[2,3-a]carbazole (compound 4 (Fischer indole synthesis))

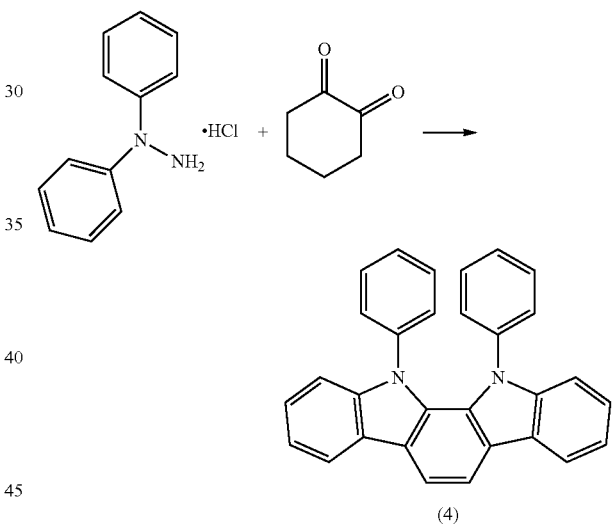

1,2-Cyclohexadione (98%; 5.0 g, 1 eq.) is dissolved in acetic acid (100%; 30 ml). 1,1-Diphenylhydrazine hydrochloride (98%; 19.68 g, 2 eq.) is slowly added thereto. The suspension is stirred at room temperature overnight. Subsequently, the reaction is stirred at reflux for 54 h. After cooling to room temperature, the suspension is filtered with suction and washed with a little acetic acid. The residue is suspended in hot distilled water, filtered off with suction and washed to neutrality. The solid is dried under reduced pressure overnight. Subsequently, the solid is dissolved in toluene (300 ml) and Pd/C (10%; 2 g) is added; the mixture is stirred at reflux overnight. The solution was filtered through Celite (super standard) and washed with toluene and methylene chloride. The clear solution is concentrated and the residue is dried at 100° C. under reduced pressure. This gives 5.11 g of compound 4, 57.2% yield.

$^1$H NMR (CD$_2$Cl$_2$, 400 MHz): δ=8.17 (d, 2H), 8.12 (s, 2H), 7.24-7.30 (m, 6H), 7.07-7.14 (m, 6H), 6.76 (d, 4H).

Synthesis Example A5

Synthesis of 11,12-diphenyl-3-(9-phenyl-9H-fluoren-9-yl)-11H,12H-indolo[2,3-a]carbazole (compound 5) and 11,12-diphenyl-3,8-bis(9-phenyl-9H-fluoren-9-yl)-11H,12H-indolo[2,3-a]carbazole (compound 6; *Organic Letters* 2006, vol. 8, No. 13, 2799-2802)

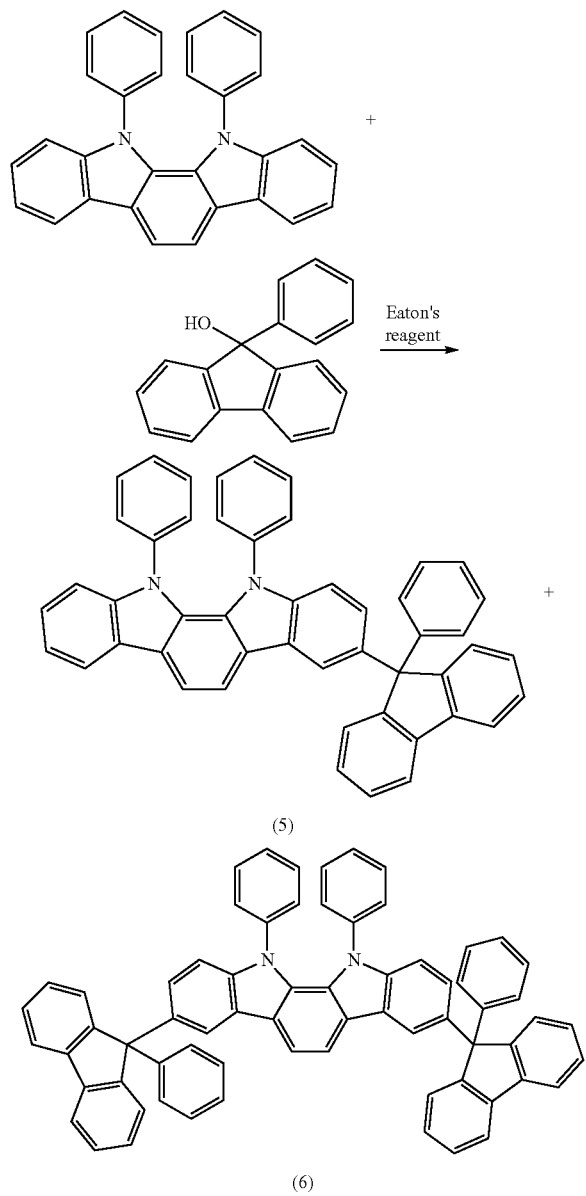

(5)

(6)

Under nitrogen, compound 4 (2.76 g, 1 eq.) and 9-phenyl-9-fluorenol (99%; 1.76 g, 1 eq.) are initially charged in dry methylene chloride (90 ml). Eaton's reagent (0.43 ml) is slowly added dropwise to this mixture which is stirred at room temperature for 8 h. Then the solvent is distilled off. Double LC (SiO$_2$; 91:9 cyclohexane/methylene chloride) gives 1.73 g of compound 5 (39.7% yield) and 1.49 g of compound 6 (25% yield).

$^1$H NMR compound 5 (CD$_2$Cl$_2$, 400 MHz): δ=8.15 (s, 1H), 8.03 (d, 1H), 7.92 (2×d, 2H), 7.80 (d, 2H), 7.48 (d, 2H), 7.36 (dd, 2H), 7.19-7.32 (m, 11H), 7.15 (d, 1H), 7.02-7.10 (m, 6H), 6.72 (dd, 4H)

$^1$H NMR compound 6 (CD$_2$Cl$_2$, 400 MHz): δ=7.88 (s, 2H), 7.80 (s+d, 6H), 7.44 (d, 4H), 7.37 (dd, 4H), 7.20-7.28 (m, 14H), 7.01-7.17 (m, 10H), 6.67 (d, 4H)

Synthesis Example A6

Synthesis of 7,12-diphenyl-7H,12H-indolo[3,2-a]carbazole (compound 7 (Fischer indole synthesis))

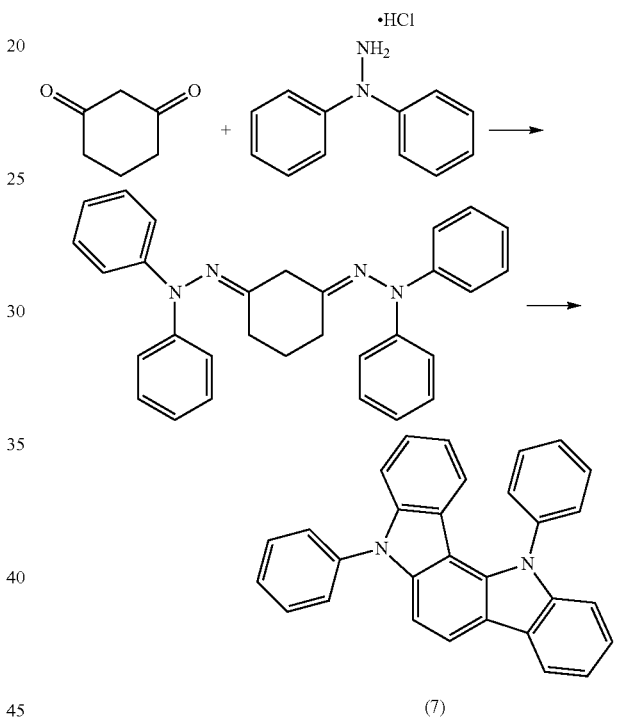

(7)

1,1-Diphenylhydrazine hydrochloride (98%; 19.7 g, 2 eq.) is introduced into a solution of 1,3-cyclohexadione (98%; 5.0 g, 1 eq.) and glacial acetic acid (50 ml). The suspension is heated gradually to reflux and stirred for 48 h. Further 1,1-diphenylhydrazine hydrochloride (98%; 15.0 g, 1.5 eq.) is added and the mixture is stirred at reflux for a further 24 h. The mixture is cooled, diluted with methylene chloride and transferred into a separating funnel. The organic phase is washed 3× with distilled water, then dried with sodium sulfate and concentrated. After drying under reduced pressure overnight, the residue is dissolved in toluene (250 ml) and Pd/C (2 g) is added. The suspension is stirred at reflux for 48 h. Then the mixture is cooled and filtered through Celite, washed with toluene and methylene chloride, concentrated and dried under reduced pressure. LC (SiO$_2$; 94:6 hexane/dichloromethane) gives 1.45 g of compound 7 (yield: 8.1%).

$^1$H NMR (CD$_2$Cl$_2$, 400 MHz): δ=8.15 (2×d, 2H), 7.5-7.7 (m, 10H), 7.25-7.35 (m, 5H), 7.20 (t, 1H), 6.75 (t, 1H), 5.95 (d, 1H)

Synthesis Example A7

Synthesis of 7,12-diphenyl-3-(9-phenyl-9H-fluoren-9-yl)-7H,12H-indolo[3,2-a]carbazole (compound 8), 7,12-diphenyl-10-(9-phenyl-9H-fluoren-9-yl)-7H, 12H-indolo[3,2-a]carbazole (compound 9) and 7,12-diphenyl-3,10-bis(9-phenyl-9H-fluoren-9-yl)-7H, 12H-indolo[3,2-a]carbazole (compound 10; *Organic Letters* 2006, Vol. 8, No. 13, 2799-2802)

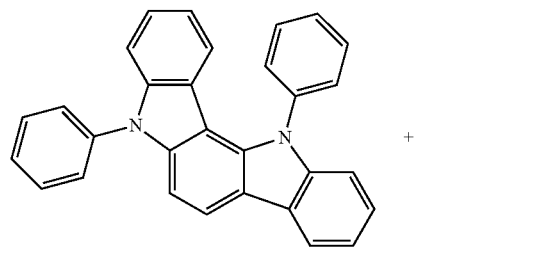

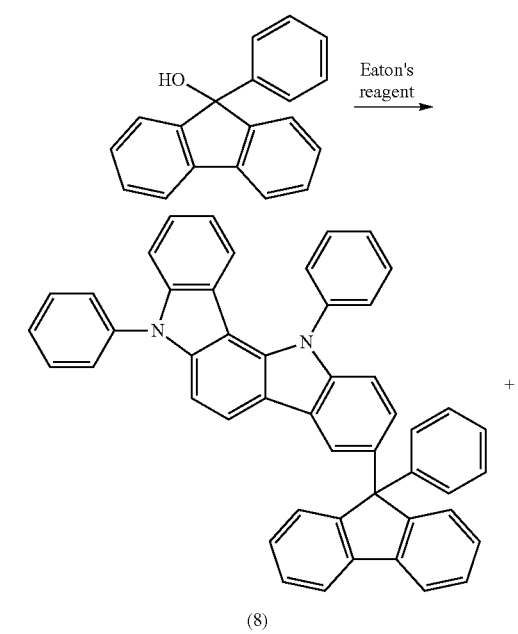

(8)

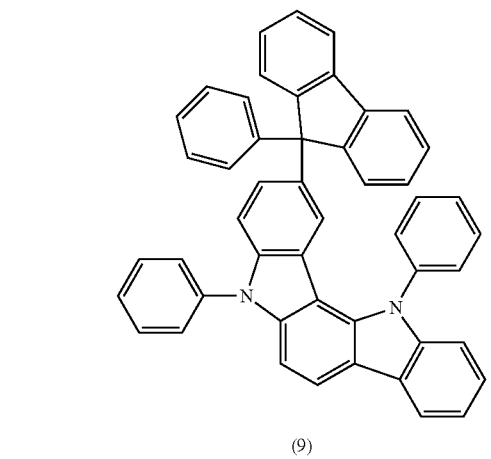

(9)

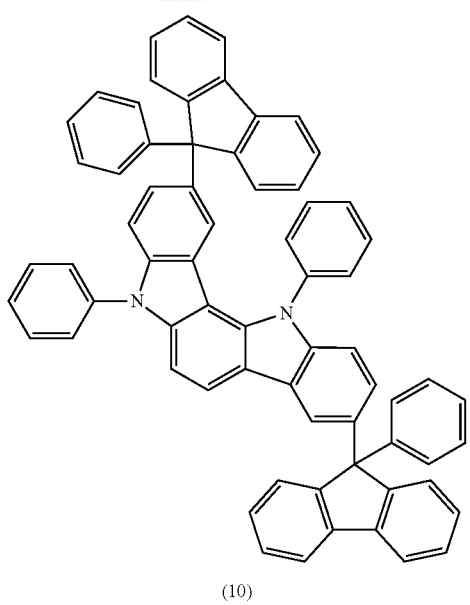 [SMILES: c1ccc(-n2c3ccc(C4(c5ccccc5)c5ccccc5-c5ccccc54)cc3c3c2ccc2c4cc(C5(c6ccccc6)c6ccccc6-c6ccccc65)ccc4n(-c4ccccc4)c23)cc1]

(10)

Under nitrogen, compound 7 (1.41 g, 1 eq.) and 9-phenyl-9-fluorenol (99%; 0.90 g, 1 eq.) are initially charged in dry methylene chloride (90 ml). Eaton's reagent (0.22 ml) is slowly added dropwise to this mixture which is stirred at room temperature overnight. Then the solvent is distilled off. Double LC ($SiO_2$; 66:34 n-hexane/methylene chloride) gives 1.0 g of compound 8+9 (in a mixture; yield 49.5%) and 0.7 g of compound 10 (yield 22.8%).

Compound 8+9: MALDI-MS: m/z=648.23.

$^1$H NMR compound 10 ($CD_2Cl_2$, 400 MHz): δ=7.93 (d, 1H), 7.87 (s, 1H), 7.82 (d, 2H), 7.77 (d, 2H), 7.59 (d, 2H), 7.47-7.54 (m, 5H), 7.03-7.40 (m, 30H), 6.73 (d, 1H)

Synthesis Example A8

Synthesis of 3,8-di-tert-butyl-11,12-diphenyl-11H, 12H-indolo[2,3-a]carbazole (compound 11; Friedel-Crafts reaction)

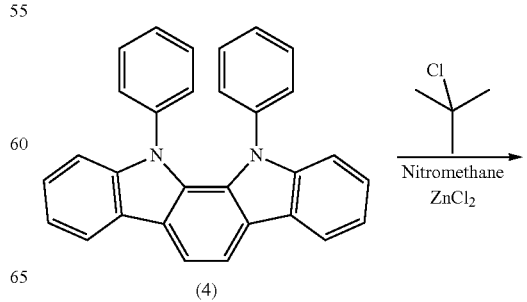

(4)

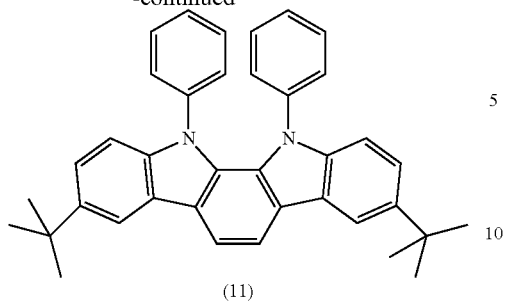

(11)

Under nitrogen, compound 4 (1.0 g, 1 eq.) and zinc chloride (1.0 g, 3 eq.) are initially charged in nitromethane (50 ml). 2-Chloro-2-methylpropane (99%; 3 eq.) is added dropwise thereto. The reaction is stirred at room temperature overnight. The next day, methylene chloride is added to the suspension, which is transferred to a separating funnel. The organic phase is washed with distilled water 3×25 ml. After drying with sodium sulfate, the solution is concentrated. Double LC ($SiO_2$; 9:1 cyclohexane/methylene chloride) gives 0.85 g of product (66.6% yield).

$^1$H NMR ($CD_2Cl_2$, 400 MHz): δ=8.18 (s, 2H), 8.13 (s, 2H), 7.38 (d, 2H), 7.20 (d, 2H), 7.06-7.12 (m, 6H), 6.74 (d, 4H), 1.43 (s, 18H)

Comparison of Glass Transition Temperatures ($T_g$):

| Compound | Tg (° C.) |
|---|---|
| 4 | 84 |
| 7 | 72 |
| 3 | 154 |
| 5 | 171 |
| 6 | 225 |
| 8 + 9 | 143 |
| 10 | 226 |
| 11 | 147 |

Diode Examples

Example A1

Production of an OLED comprising 3,8-di-tert-butyl-11,12-diphenyl-11H,12H-indolo[2,3-a]carbazole (compound 11)

The ITO substrate used as the anode is first cleaned with commercial detergents for LCD production (Deconex® 20NS, and 25ORGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Next, the AJ20-1000 hole injection layer from Plexcore is spun on from solution (~40 nm).

Thereafter, the organic materials specified below are applied by vapor deposition to the cleaned substrate at a rate of approx. 0.5-5 nm/min at about $10^{-8}$ mbar. As a hole conductor and exciton blocker, Ir(dpbic)$_3$ (V1) is applied to the substrate with a thickness of 45 m, the first 35 nm of which have been doped with $MoO_x$ (~50%) to improve the conductivity.

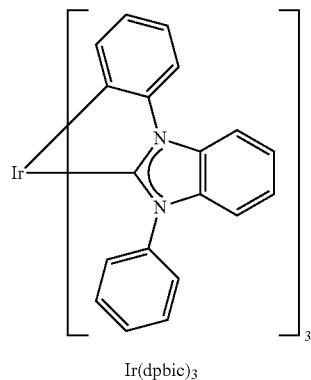

Ir(dpbic)₃

(for preparation, see Ir complex (7) in the application WO 2005/019373).

Subsequently, a mixture of 20% by weight of the compound (Em1-i)

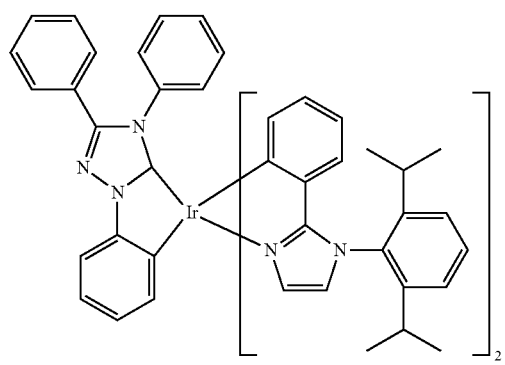

(The compound Em1-i and the preparation process therefor are disclosed in U.S. Provisional Application 61/255,499.)

and 80% by weight of the compound 11 are applied by vapor deposition in a thickness of 40 nm, the former compound functioning as an emitter material, the latter as a matrix material.

Subsequently, the material 12 (described in PCT application PCT/EP2009/067120) is applied by vapor deposition with a thickness of 5 nm as an exciton and hole blocker.

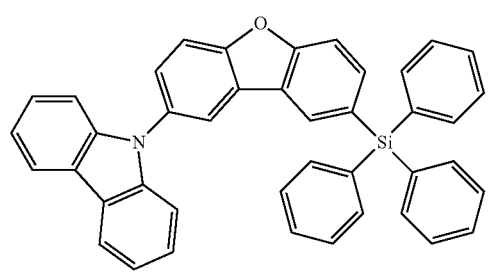

Next, as an electron transporter, a mixture of 12 (20%) and BCP (2,9-dimethyl-4,7-diphenyl-1,10-phenanthroline, 80%) is applied by vapor deposition in a thickness of 40 nm, followed by a 1.0 nm-thick LiF layer and finally a 100 nm-thick Al electrode. All components are bonded in an inert nitrogen atmosphere with a glass cover.

To characterize the OLED, electroluminescence spectra are recorded at various currents and voltages. In addition, the current-voltage characteristic is measured in combination with the light output emitted. The light output can be converted to photometric parameters by calibration with a photometer.

Example A2

As in example A1, except that the matrix material used is compound 3 instead of compound 11. The hole/exciton blocker used, instead of 12, is 10 nm of the following compound.

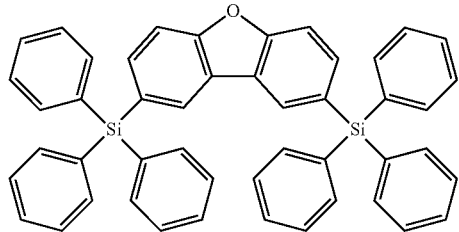 [SMILES: c1ccc([Si](c2ccccc2)(c2ccccc2)c2ccc3oc4ccc([Si](c5ccccc5)(c5ccccc5)c5ccccc5)cc4c3c2)cc1]

The electron transporter used is 20 nm of BCP.

Example A3

As in example A1, except that the matrix material used is compound 5 instead of compound 11. The emitter used is isomer Em1-s. The compound Em1-s and the preparation process therefor are disclosed in U.S. Provisional Application 61/255,499.

| Diode example | Inventive compound | Voltage at 300 cd/m² (V) | Current efficiency at 300 cd/m² (cd/A) | EQE at 300 cd/m² (%) |
|---|---|---|---|---|
| A1 | 11 | 5.0 | 25 | 11 |
| A2 | 3 | 6.2 | 19 | 8.0 |
| A3 | 5 | 4.9 | 13 | 5.6 |

Example A4

As in example A3, except that the hole conductor and exciton blocker used is compound 5 instead of Ir(dpbic)$_3$ (V1).

Example A5

As in example A3, except that as emission layer a mixture of compound 5 (30%) is used.

Example A6

The ITO substrate used as the anode is first cleaned with commercial detergents for LCD production (Deconex® 20NS, and 25ORGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Next, the AJ20-1000 hole injection layer from Plexcore is spun on from solution.

After the hole injection layer, the organic materials specified below are applied by vapor deposition to the cleaned substrate at a rate of approx. 0.5-5 nm/min at about $10^{-7}$ to $10^{-9}$ mbar. As a hole conductor and exciton blocker, Ir(dpbic)$_3$ (V1) is applied to the substrate with a thickness of 45 nm, the first 35 nm of which have been doped with 10% by weight MoO$_x$ to improve the conductivity.

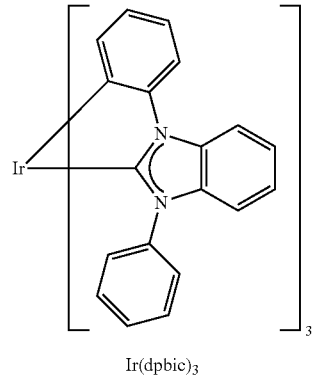

Ir(dpbic)$_3$ (for preparation, see Ir complex (7) in the application WO 2005/019373).

Subsequently, a mixture of 20% by weight of the following emitter material

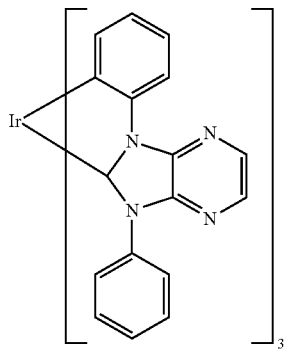

and 80% by weight of the compound 11 are applied by vapor deposition in a thickness of 20 nm (embodiment A6.1) respectively 40 nm (embodiment A6.2), the latter compound functioning as a matrix material.

Subsequently, the material 22 (described in PCT application PCT/EP2009/067120) is applied by vapor deposition with a thickness of 10 nm as an exciton and hole blocker.

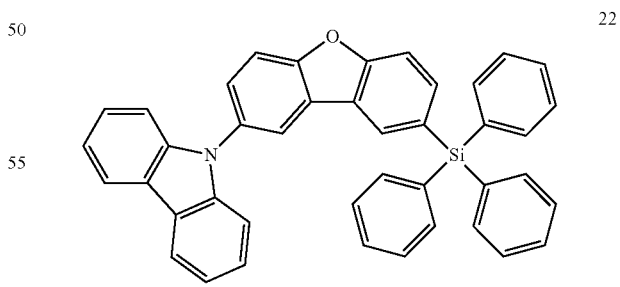

Next, as an electron transporter, a mixture of material 22 (20% by weight) and BCP (2,9-dimethyl-4,7-diphenyl-1,10-phenanthroline, 80% by weight) is applied by vapor deposition in a thickness of 20 nm, followed by a 0.7 nm-thick Liq layer and finally a 100 nm-thick Al electrode. All components are bonded in an inert nitrogen atmosphere with a glass cover.

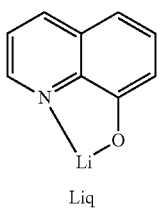

Liq

To characterize the OLED, electroluminescence spectra are recorded.

The following data are obtained for both embodiments C8.1 and C8.2 of a white OLED:

| Example | CIE |
|---|---|
| A6.1 (20 nm EML) | 0.16/0.26 |
| A6.2 (40 nm EML) | 0.16/0.24 |

B Benzofuranyl- and benzothiophenylcarbazoles

Synthesis Examples

1st Comparative Example

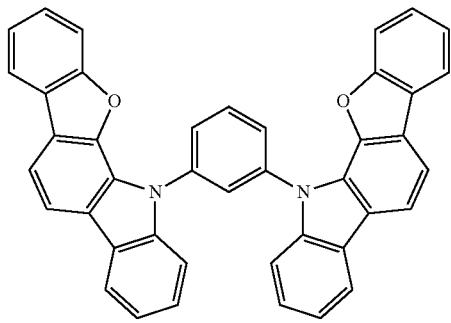

(3)

Synthesis Example B1

Synthesis of 2-benzofuran-2-yl-1H-indole (compound 1)

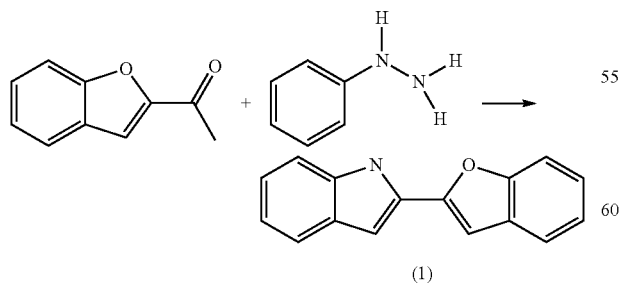

(1)

Phenylhydrazine (97%; 6.3 ml, 1 eq) is introduced into a solution of 2-acetylbenzofuran (10 g, 1 eq) in ethanol (25 ml). After adding 20 drops of glacial acetic acid, the mixture is stirred at 80° C. for 1 h. Subsequently, the solvent is distilled off. The residue is introduced gradually into polyphosphoric acid (100 g), heated to 120° C. and stirred for 1 h. The reaction output is added cautiously to ice-water and neutralized with 2M NaOH. The precipitate is filtered off and washed with distilled water. The residue is dried under reduced pressure. After recrystallization in ethyl acetate/n-hexane, 7.0 g are obtained. Yield: 48%

$^1$H NMR (CDCl$_3$, 400 MHz):

δ=8.62 (br s, 1H), 7.62 (d, 1H), 7.57 (d, 1H), 7.49 (d, 1H), 7.40 (d, 1H), 7.27-7.19 (m, 3H), 7.12 (t, 1H), 6.96 (s, 2H)

Synthesis Example B2

Synthesis of 12H-benzofuranyl[2,3-a]carbazole (compound 2)

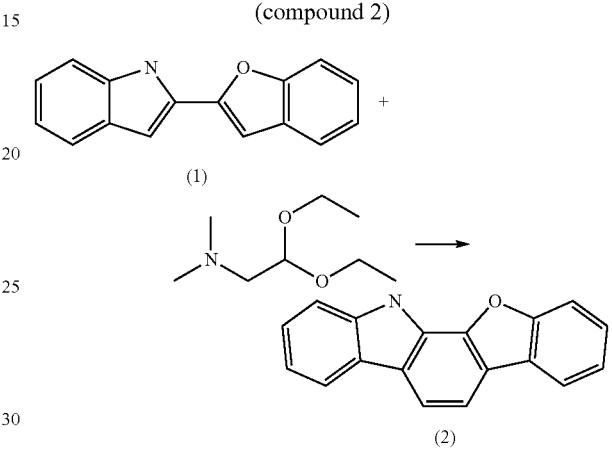

Compound 1 (2.0 g, 1 eq.) is added to acetic acid (90 ml) and heated to reflux. (Dimethylamino)acetaldehyde diethyl acetal (95%; 14.6 g, 10 eq.) is added dropwise in portions to the solution. The reaction is stirred at reflux until no reactant is present any longer. Subsequently, the flask contents are diluted with CH$_2$Cl$_2$ at room temperature and washed in a separating funnel with distilled water and NaCl (saturated). Organic phase is dried with Na$_2$SO$_4$ and concentrated. LC (SiO$_2$, 15:85 CH$_2$Cl$_2$/n-hex) gives the product 2 (0.85 g, 39% yield).

$^1$H NMR (CD$_2$Cl$_2$, 400 MHz): δ=8.68 (br s, 1H), 8.15 (d, 1H), 8.06 (dd, 2H), 7.83 (d, 1H), 7.67 (d, 1H), 7.59 (d, 1H), 7.47 (dd, 2H), 7.41 (dd, 1H), 7.30 (dd, 1H).

Synthesis Example B3

Synthesis of 1,3-bis(12-(12H-benzofuranyl[2,3-a] carbazolyl)benzene (compound 3)

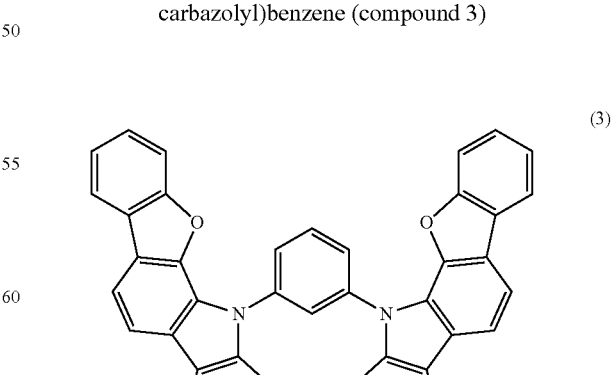

(3)

The suspension of compound 2 (1.95 g, 7.6 mmol), 1,3-diiodobenzene (98%; 1.28 g, 3.8 mmol), potassium carbonate (2.63 g, 19 mmol) and copper powder (0.19 g, 3 mmol) in n-tridecane (5 ml) is heated to 185° C. and stirred for 72 h. The mixture is cooled to room temperature and diluted with n-heptane, filtered and washed with n-heptane. The residue is then washed with warm distilled water to free it of salts and dried at 65° C. under reduced pressure. After double recrystallization in $CH_2Cl_2$/n-hexane (15% $CH_2Cl_2$), 1.3 g of product were obtained. Yield: 68%.

$^1$H NMR ($CD_2Cl_2$, 400 MHz): δ=8.20 (d, 2H), 8.14 (d, 2H), 8.04-8.06 (m, 3H), 7.92-7.93 (m, 3H), 7.89 (d, 2H), 7.80 (d, 2H) 7.46-7.32 (m, 10H).

2nd Comparative Example

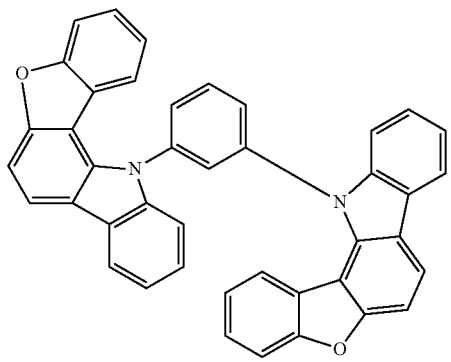

(7)

Synthesis example B4

Synthesis of 1-benzofuran-3-ylethanone (compound 4)

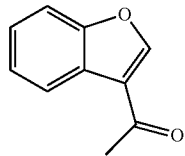

(4)

(Literature: Synthesis, 1980, 286)

Technical-grade 2-methoxyphenylacetone (13.14 g, 1 eq.) and N,N-dimethylformamide diethyl acetal (28.09 g, 2.4 eq.) are added to DMF (8 ml) and the mixture is heated to 80° C. The reaction is stirred at 80° C. for 24 h. Then the DMF is distilled off and the oil obtained is dried under reduced pressure at 65° C. Yield: 18.5 g The dry residue is dissolved in anhydrous methylene chloride and cooled to 0° C. A solution of boron tribromide (200 ml) in methylene chloride (100 ml) is cautiously added dropwise and the mixture is stirred for 1 h. Nitrogen is used to blow out the flask; the reaction output is slowly added dropwise to an ice/$NaHCO_3$ solution. The suspension is stirred overnight. The solution obtained is extracted with methylene chloride in a separating funnel. The organic phase obtained is washed with distilled water, dried with sodium sulfate. After concentrating the solution, the residue is dried under reduced pressure. The product is obtained with a final weight of 10.37 g and a crude yield of 81%.

$^1$H NMR ($CD_2Cl_2$, 400 MHz): δ=8.25 (s, 1H), 8.19 (d, 1H), 7.54 (d, 1H), 7.35-7.38 (m, 2H), 2.51 (s, 3H).

Synthesis Example B5

Synthesis of 2-benzofuran-3-yl-1H-indole (compound 5)

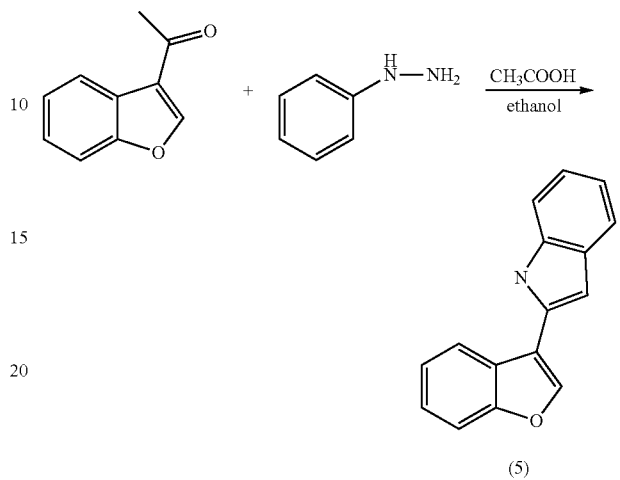

(5)

Phenylhydrazine (97%; 3.5 g, 1 eq) is introduced into a solution of compound 4 (5 g, 1 eq) in absolute ethanol (40 ml). After adding 20 drops of glacial acetic acid, the mixture is stirred at room temperature for 8 h. Subsequently, the mixture is added to distilled water and transferred to a separating funnel. The organic phase is extracted with methylene chloride and dried with sodium sulfate. After concentrating at 65° C. under reduced pressure, dried overnight. The 4.76 g of product obtained are slowly introduced into polyphosphoric acid (40 g), heated to 120° C. and stirred for 1 h. The reaction output is added cautiously to ice-water and neutralized with NaOH (w=50%). The precipitate is filtered off and washed with distilled water. The residue is dried under reduced pressure. LC ($SiO_2$; 4:1 cyclohexane/methylene chloride) gives 2.8 g (38.5% yield).

$^1$H NMR ($CDCl_3$, 400 MHz): δ=8.42 (br s, 1H), 7.97 (m, 2H), 7.65 (d, 1H), 7.58 (d, 1H), 7.37-7.46 (m, 3H), 7.21 (dd, 1H), 7.13 (dd, 1H), 6.90 (s, 1H).

Synthesis Example B6

Synthesis of 12H-benzofuranyl[3,2-a]carbazole (compound 6)

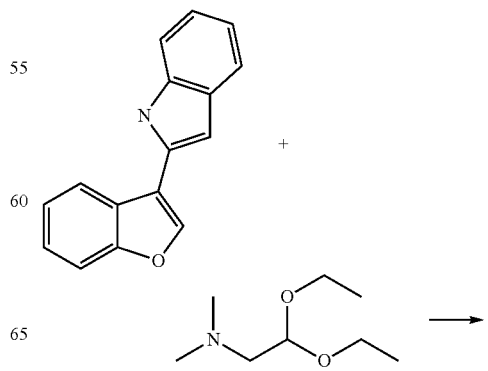

2H) 7.35 (d, 2H), 7.25-7.32 (m, 4H), 7.12 (dd, 2H), 6.23 (d, 2H).

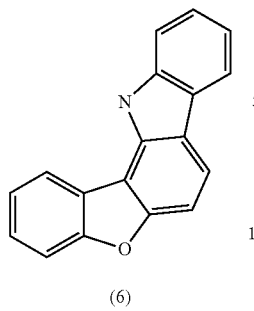

(6)

Compound 5 (2.8 g, 1 eq.) is added to acetic acid (30 ml) and heated to reflux. (Dimethylamino)acetaldehyde diethyl acetal (95%; 20.3 g, 10 eq.) is added dropwise in portions to the solution. The reaction is stirred at reflux overnight. Then further (dimethylamino)acetaldehyde diethyl acetal (95%; 2.0 g) is added and stirred further at reflux after 3 h. Subsequently, the flask contents are diluted with $CH_2Cl_2$ at room temperature and washed in a separating funnel with distilled water and NaCl (saturated). Organic phase is dried with $Na_2SO_4$ and concentrated. LC ($SiO_2$, 15:85 ethyl acetate/ cyclohexane) gives the product 6 (1.92 g, 62.2% yield).

$^1$H NMR ($CD_2Cl_2$, 400 MHz): δ=8.88 (br s, 1H), 8.16 (d, 1H), 8.12 (d, 2H), 7.66 (d, 1H), 7.62 (d, 1H), 7.42-7.53 (m, 4H), 7.31 (dd, 1H).

Synthesis Example B7

Synthesis of 1,3-bis(12-(12H-benzofuranyl[3,2-a]) carbazolyl)benzene (compound 7)

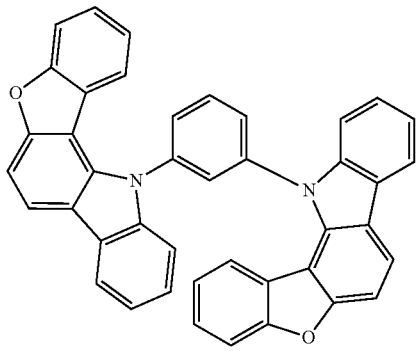

(7)

The suspension of compound 6 (1.70 g, 6.6 mmol), 1,3-diiodobenzene (98%; 1.11 g, 3.3 mmol), potassium carbonate (2.28 g, 17 mmol) and copper powder (0.17 g, 2.6 mmol) in n-tridecane (3 ml) is heated to 145° C. and stirred for 48 h. Then compound 6 (0.5 g) is added and the reaction temperature is increased to 185° C. and the mixture is stirred for a further 24 h. The mixture is cooled to room temperature and diluted with n-heptane, filtered and washed with n-heptane. The residue is then washed with warm distilled water to free it of salts and dried at 65° C. under reduced pressure. LC ($SiO_2$, 1:4 methylene chloride/cyclohexane) gives the product 7 (0.89 g, 48% yield).

$^1$H NMR ($CD_2Cl_2$, 400 MHz): δ=8.21 (d, 2H), 8.12 (d, 2H), 7.97-8.07 (m, 3H), 7.75 (s, 1H), 7.58 (dd, 4H), 7.40 (d,

1st Inventive Example

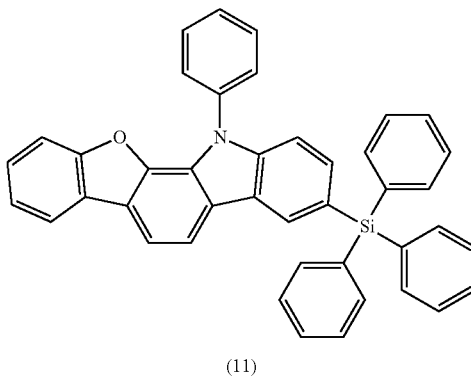

(11)

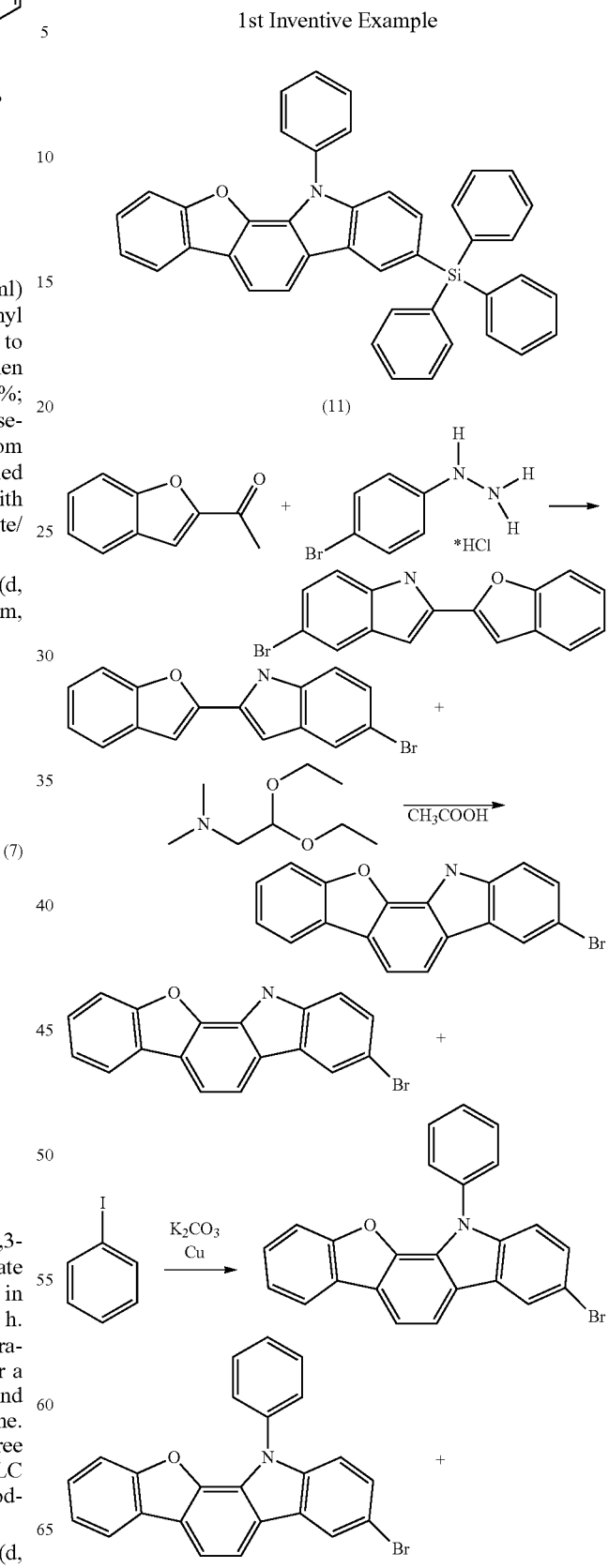

-continued

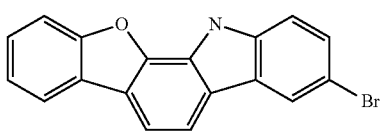

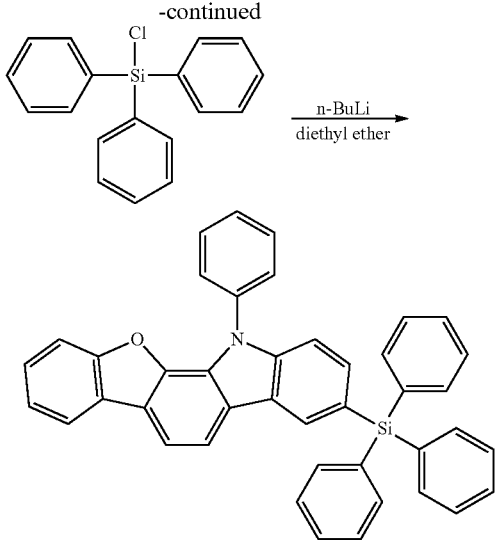

Synthesis Example B8

Synthesis of 2-benzofuran-2-yl-5-bromo-1H-indole (compound 8)

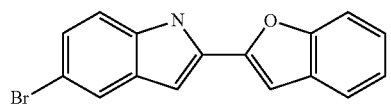

2-Acetylbenzofuran (10 g, 1 eq.) is initially charged in absolute ethanol (80 ml) and the mixture is stirred for 30 min. Then 4-bromophenylhydrazine hydrochloride (99%; 14.1 g, 1 eq.) is introduced and 30 drops of glacial acetic acid are added. The mixture is stirred at room temperature for 3 h and stirred at 80° C. overnight. Distilled water is added to the residue, which is neutralized. Then the mixture is extracted by shaking with methylene chloride in a separating funnel. The organic phase is dried and concentrated, dried under reduced pressure.

The black residue is introduced into polyphosphoric acid (80 g) in a 2 l flask and heated gradually to 120° C., stirred for a further 1 h. Then 300 ml of distilled water is added slowly and the mixture is stirred overnight. The suspension is neutralized with 50% NaOH and filtered, and the residue is washed with distilled water. After drying under reduced pressure, 13 g of product are obtained.

LC ($SiO_2$, 3:7 dichloromethane/n-hexane) gives the product 8 (1.7 g, 8.6% yield).

$^1$H NMR ($CD_2Cl_2$, 400 MHz): δ=8.85 (br s, 1H), 7.77 (s, 1H), 7.62 (d, 1H), 7.54 (d, 1H), 7.25-7.36 (m, 4H), 7.07 (s, 1H), 6.94 (s, 1H)

Synthesis Example B9

Synthesis of 3-bromo-12H-benzofuranyl[2,3-a]carbazole (compound 9)

(9)

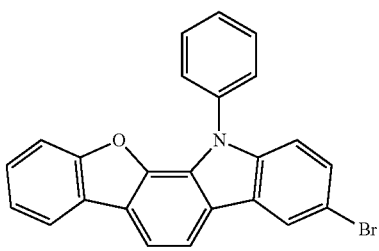

Under nitrogen, compound 8 (1.3 g, 1 eq.) is initially charged and dissolved with acetic acid (55 ml) while heating to reflux. Then (dimethylamino)acetaldehyde diethyl acetal (95%; 7.1 g, 10 eq.) is added dropwise to the reaction within 1.5 h and the mixture is stirred at reflux for a further 7 h. It is stirred at room temperature overnight. The next day, it is heated back to reflux and a further 2 g of (dimethylamino)acetaldehyde diethyl acetal are added dropwise. After 6 h at reflux, a further 4 g (dimethylamino)acetaldehyde diethyl acetal are added dropwise and it is stirred for a further 7.5 h. The mixture is cooled to room temperature and diluted with methylene chloride. Washed in a separating funnel with distilled water and then with saturated NaCl. The organic phase is dried with sodium sulfate and concentrated. LC (C18-$SiO_2$, acetonitrile) gives 0.33 g of product (24% yield).

$^1$H NMR ($CD_2Cl_2$, 400 MHz): δ=8.7 (br s, 1H), 8.15 (d, 2H), 8.06 (d, 1H), 7.78 (d, 1H), 7.60 (m, 3H), 7.48 (dd, 1H), 7.32 (dd, 1H).

Synthesis Example B10

Synthesis of 3-bromo-12-phenyl-12H-benzofuranyl[2,3-a]carbazole (compound 10)

(10)

In a nitrogen countercurrent, compound 9 (0.46 g, 1 eq.) is added to a flask together with iodobenzene (98%; 1.75 g, 6 eq.), potassium carbonate (0.48 g, 2.5 eq.) and copper powder (20 mg, 0.2 eq.). The suspension is heated to 185° C. while stirring, and stirred overnight. The next day, the mixture is cooled to room temperature and diluted with methylene chloride. The suspension is filtered with suction and the solids are washed with methylene chloride. n-Heptane is then added to the filtrate; the methylene chloride present is distilled off on a rotary evaporator. The suspension obtained is filtered with suction and the solids are washed with n-heptane. The filtrate is concentrated; the residue purified by means of column chromatography. This gives 0.57 g of product, 100% yield.

$^1$H NMR (CD$_2$Cl$_2$, 400 MHz): δ=8.33 (s, 1H), 8.09 (d, 1H), 8.03 (d, 1H), 7.90 (d, 1H), 7.67-7.68 (m, 4H), 7.60 (m, 1H), 7.52 (d, 1H), 7.33-7.45 (m, 4H).

Synthesis Example B11

Synthesis of 12-phenyl-3-triphenylsilyl-12H-benzofuranyl[2,3-a]carbazole (compound 11)

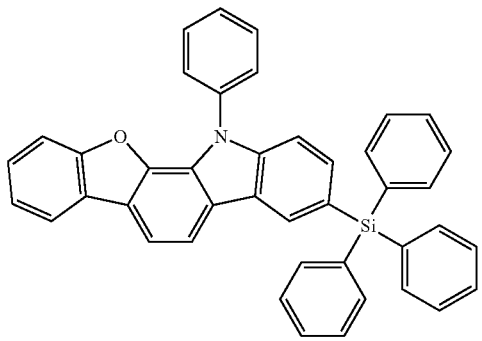

(11)

n-Butyllithium (1.6 M in hexane, 0.5 ml, 1.1 eq.) is slowly added dropwise at room temperature under nitrogen to a suspension of compound 10 (320 mg, 1 eq.) and chlorotriphenylsilane (97%; 237 mg, 1 eq.) in dry diethyl ether (25 ml) and the mixture is stirred at room temperature. Subsequently, saturated NH$_4$Cl solution (10 ml) is added to the suspension and the mixture is stirred for 30 min. Methylene chloride is added to the suspension and the resulting emulsion is separated in a separating funnel. The organic phase is washed with water (3×50 ml), dried with Na$_2$SO$_4$ and concentrated. LC (SiO$_2$, 1:3 CH$_2$Cl$_2$/cyclohexane) gives 0.20 g of product (43.4% yield).

$^1$H NMR (CD$_2$Cl$_2$, 400 MHz): δ=8.42 (s, 1H), 8.01 (dd, 2H), 7.83 (d, 1H), 7.54-7.72 (m, 12H), 7.32-7.51 (m, 13H).

2nd Inventive Example

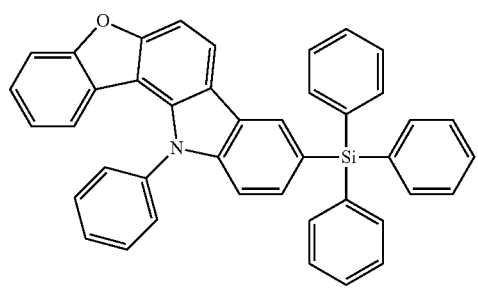

(15)

Synthesis Example B12

Synthesis of 2-benzofuran-3-yl-5-bromo-1H-indole (compound 12)

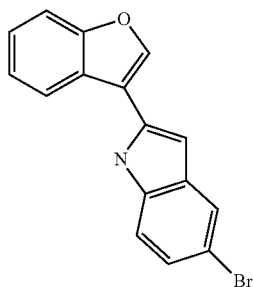

(12)

Under nitrogen, compound 4 (5.1 g, 1 eq.) is initially charged in absolute ethanol. 4-Bromophenylhydrazine hydrochloride (99%; 7.2 g, 1 eq.) is introduced. 20 drops of glacial acetic acid are added to this mixture and the reaction is stirred at room temperature for 72 h. Then 4-bromophenylhydrazine hydrochloride (99%; 1 g, 0.14 eq.) is added and the mixture is stirred at room temperature for a further 5 h. The experiment is added to distilled water and extracted with methylene chloride in a separating funnel. The organic phase is dried with sodium sulfate and concentrated, and the residue is dried under reduced pressure. This gives 9.7 g of viscous red-brown residue. This is introduced gradually into polyphosphoric acid (40 g), and the mixture is heated to 120° C. and stirred for 1 h. The reaction output is added gradually to ice-water and neutralized with 50% sodium hydroxide solution. Ethyl acetate is added to the suspension, which is washed vigorously with ethyl acetate in a separating funnel. The organic phase is dried with sodium sulfate and concentrated, dried under reduced pressure. The 6.44 g of product are adsorbed onto silica gel and separated by means of LC (SiO$_2$; 95:5 cyclohexane/ethyl acetate). This gives 3.22 g of product (32.4% yield).

$^1$H NMR (CD$_2$Cl$_2$, 400 MHz): δ=9.47 (br s, 1H), 8.06 (s, 1H), 7.95 (d, 1H), 7.77 (s, 1H), 7.58 (d, 1H), 7.38-7.42 (m, 2H), 7.25-7.34 (m, 2H), 6.84 (s, 1H).

Synthesis Example B13

Synthesis of 3-bromo-12H-benzofuranyl[3,2-a]carbazole (compound 13)

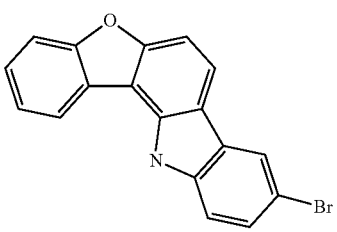

(13)

Under nitrogen, compound 12 (3.2 g, 1 eq) is initially charged and dissolved with acetic acid (30 ml) while heating to reflux. Then (dimethylamino)acetaldehyde diethyl acetal (95%; 21.9 g, 10 eq.) is added dropwise to the reaction within 1 h and the mixture is stirred at reflux for 48 h. The mixture is cooled to room temperature and diluted with methylene chloride. Washed in a separating funnel with distilled water and then with saturated NaCl solution. The organic phase is dried with sodium sulfate and concentrated. LC (SiO$_2$, 3:1 cyclohexane/methylene chloride) gives 0.98 g of product (28.6% yield).

$^1$H NMR (CD$_2$Cl$_2$, 400 MHz): δ=8.75 (s, 1H), 8.24 (s, 1H), 8.1 (dd, 2H), 7.67 (d, 1H), 7.48-7.55 (m, 6H).

Synthesis Example B14

Synthesis of 3-bromo-12-phenyl-12H-benzofuranyl[3,2-a]carbazole (compound 14)

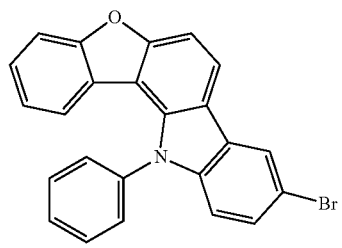

(14)

In a nitrogen countercurrent, compound 13 (0.97 g, 1 eq.) is added to a flask together with iodobenzene (98%; 3.62 g, 6 eq.), potassium carbonate (1.01 g, 2.5 eq.) and copper powder (37 mg, 0.2 eq.). The suspension is heated to 185° C. while stirring, and stirred overnight. The next day, the mixture is cooled to room temperature and diluted with methylene chloride. The suspension is filtered with suction and the solids are washed with methylene chloride. n-Heptane is then added to the filtrate; the methylene chloride present is distilled off on a rotary evaporator. The suspension obtained is filtered with suction and the solids are washed with n-heptane. The filtrate is concentrated; the residue purified by means of column chromatography. This gives 0.99 g of product, 82% yield.

$^1$H NMR (CD$_2$Cl$_2$, 400 MHz): δ=8.30 (s, 1H), 8.20 (d, 1H), 7.66-7.72 (m, 3H), 7.53-7.62 (m, 4H), 7.46 (d, 1H), 7.31 (dd, 1H), 7.14 (d, 1H), 6.88 (dd, 1H), 5.65 (d, 1H).

Synthesis Example B15

Synthesis of 12-phenyl-3-triphenylsilyl-12H-benzofuranyl[3,2-a]carbazole (compound 15)

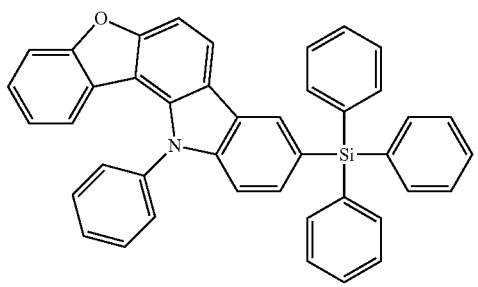

(15)

Compound 14 (920 mg, 1 eq.) and chlorotriphenylsilane (97%; 699 mg, 1 eq.) are stirred under nitrogen in dry diethyl ether (80 ml). n-Butyllithium (1.7 M in pentane, 1.58 ml, 1.1 eq.) is slowly added dropwise to the suspension and the mixture is stirred for a further 1.5 h. Then the suspension is stirred at reflux for 3 h. A saturated ammonium chloride solution (10 ml) is added to the suspension and the precipitated salt is filtered off. The residue is washed with methylene chloride. The filtrate is transferred to a separating funnel with methylene chloride, and the organic phase is washed with water (3×50 ml), dried with Na$_2$SO$_4$ and concentrated. The dried residue is separated by means of column chromatography: LC (SiO$_2$; cyclohexane/methylene chloride (7% methylene chloride)) gives 200 mg of product, 16.7% yield.

$^1$H NMR (CD$_2$Cl$_2$, 400 MHz): δ=8.39 (s, 1H), 8.16 (d, 1H), 7.61-7.70 (m, 12H), 7.55 (m, 3H), 7.38-7.48 (m, 9H), 7.30 (dd, 1H), 6.88 (t, 1H), 5.68 (d, 1H).

3rd Inventive Example

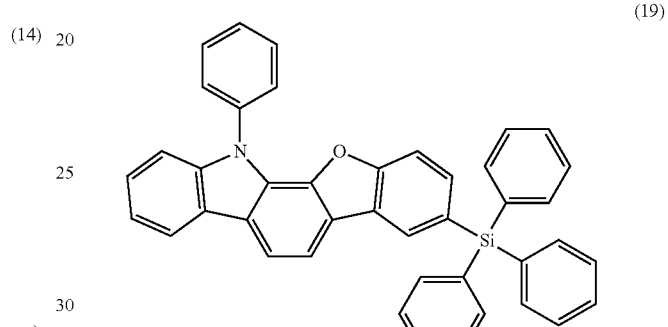

(19)

Synthesis Example B16

Synthesis of 2-(5-bromobenzofuran-2-yl)-1H-indole (compound 16)

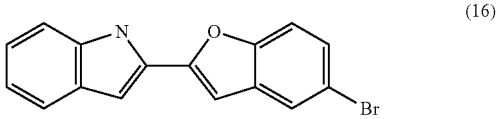 [SMILES: Brc1ccc2oc(-c3cc4ccccc4[nH]3)cc2c1]

(16)

Under nitrogen, 2-acetyl-5-bromobenzo[b]furan (commercially available, 5.0 g, 1 eq.) is initially charged in absolute ethanol. Phenylhydrazine (97%; 2.33 g, 1 eq.) is introduced. 20 drops of glacial acetic acid are added to this mixture and the reaction is stirred at room temperature for 24 h. Then phenylhydrazine (97%; 0.36 g, 0.15 eq.) is added and the mixture is stirred at room temperature for a further 5 h. The solids are filtered off and washed with distilled water. Dried under reduced pressure at 65° C. This gives 6.65 g of intermediate. This is introduced gradually into polyphosphoric acid (60 g), and the mixture is heated to 120° C. and stirred for a further 1 h. 0.5 l of distilled water is cautiously added dropwise to the reaction and the mixture is stirred for a further 2 h. The suspension obtained is neutralized with 50% sodium hydroxide solution. The suspension is filtered with suction and the solids are washed with distilled water. The solids obtained are dried under reduced pressure. This gives 6.07 g of slightly contaminated product (crude yield 93%). This is used in the next stage without purification.

$^1$H NMR (CD$_2$Cl$_2$; 400 MHz): δ=8.74 (br s, 1H), 7.74 (s, 1H), 7.64 (d, 1H), 7.38-7.46 (m, 3H), 7.24 (dd, 1H), 7.14 (dd, 1H), 7.01 (s, 1H), 6.96 (s, 1H).

Synthesis Example B17

Synthesis of 8-bromo-12H-benzofuranyl[2,3-a]carbazole (compound 17)

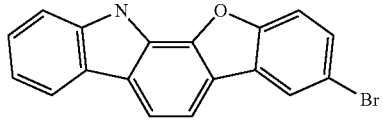

(17)

Under nitrogen, compound 16 (4.6 g, 1 eq) is initially charged and dissolved with acetic acid (185 ml) while heating to reflux. Then (dimethylamino)acetaldehyde diethyl acetal (95%; 25 g, 10 eq.) is added dropwise to the reaction within 1 h and the mixture is stirred at reflux for 7 h. The mixture is cooled to room temperature and diluted with methylene chloride. In a separating funnel, the organic phase is washed with distilled water and then with saturated NaCl solution. The organic phase is dried with sodium sulfate and concentrated. LC (reverse phase, acetonitrile) gives 1.35 g of product (27.3% yield).

$^1$H NMR (CD$_2$Cl$_2$; 400 MHz): δ=8.73 (s, 1H), 8.17 (s, 1H), 8.16 (d, 1H), 8.08 (d, 1H), 7.78 (d, 1H), 7.60 (d, 1H), 7.56 (m, 2H), 7.49 (dd, 1H), 7.31 (dd, 1H).

Synthesis Example B18

Synthesis of 8-bromo-12-phenyl-12H-benzofuranyl[2,3-a]carbazole (compound 18)

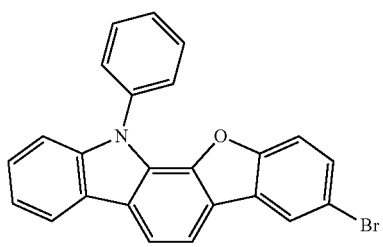

(18)

In a nitrogen countercurrent, compound 17 (1.44 g, 1 eq.) is added to a flask together with iodobenzene (98%; 5.16 g, 6 eq.), potassium carbonate (1.49 g, 2.5 eq.) and copper powder (60 mg, 0.2 eq.). The suspension is heated to 185° C. while stirring, and stirred overnight. The next day, the mixture is cooled to room temperature and diluted with methylene chloride. The suspension is filtered with suction and the solids are washed with methylene chloride. n-Heptane is then added to the filtrate; the methylene chloride present is distilled off on a rotary evaporator. The suspension obtained is filtered with suction and the solids are washed with n-heptane. The filtrate is concentrated, the residue purified by means of column chromatography (SiO$_2$; 9:1 cyclohexane/methylene chloride). This gives 1.32 g of product, 74.5% yield.

$^1$H NMR (CD$_2$Cl$_2$, 400 MHz): δ=8.21 (d, 1H), 8.16 (m, 2H), 7.83 (d, 1H), 7.64-7.70 (m, 4H), 7.58 (t, 1H), 7.44-7.51 (m, 3H), 7.32-7.37 (m, 2H).

Synthesis Example B19

Synthesis of 12-phenyl-8-triphenylsilylbenzofuranyl[2,3-a]carbazole (compound 19)

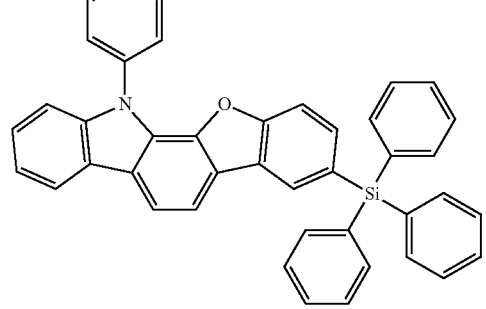

(19)

Compound 18 (1.24 g, 1 eq.) is initially charged in ultradry diethyl ether (150 ml). At room temperature, n-butyllithium (2.06 ml, 1.6 M, 1.1 eq.) is slowly added dropwise within 40 min and the mixture is stirred for a further 1 h. Then a solution of ultradry diethyl ether (40 ml) and chlorotriphenylsilane (97%; 0.91 g, 1 eq.) is added dropwise to the reaction. The experiment is stirred at room temperature for a further 1 h and then stirred at reflux for 5 h. The mixture is cooled to room temperature and quenched with 15 ml of a saturated ammonium chloride solution. The precipitated salt is filtered off and washed with methylene chloride. In a separating funnel, the aqueous phase of the filtrate is removed and the organic phase is washed with distilled water (3×50 ml). After drying with sodium sulfate, the organic phase is concentrated and the residue is dried under reduced pressure. LC (SiO$_2$, 50:50 cyclohexane/CH$_2$Cl$_2$) gives the product 19 (0.51 g, 28.7% yield).

$^1$H NMR (CD$_2$Cl$_2$, 400 MHz): δ=8.25 (s, 1H), 8.20 (d, 1H), 8.12 (d, 1H), 7.79 (d, 1H), 7.71 (d, 2H), 7.67 (dd, 2H), 7.62 (d, 6H), 7.57 (dd, 2H), 7.44-7.49 (m, 6H), 7.41 (dd, 6H), 7.34 (t, 1H)

Diode Examples

Comparative Example B1

Production of an OLED comprising 1,3-bis(12-(12H-benzofuranyl[2,3-a]carbazolyl)benzene (compound 3)

The ITO substrate used as the anode is first cleaned with commercial detergents for LCD production (Deconex® 20NS, and 25ORGAN-ACID® neutralizing agent) and then in an acetone/isopropanol mixture in an ultrasound bath. To eliminate any possible organic residues, the substrate is exposed to a continuous ozone flow in an ozone oven for a further 25 minutes. This treatment also improves the hole injection properties of the ITO. Next, the AJ20-1000 hole injection layer from Plexcore is spun on from solution (~40 nm).

Thereafter, the organic materials specified below are applied by vapor deposition to the cleaned substrate at a rate of approx. 0.5-5 nm/min at about 10$^{-8}$ mbar. As a hole conductor and exciton blocker, Ir(dpbic)$_3$ (V1) is applied to the substrate with a thickness of 40 nm, the first 35 nm of which have been doped with MoO$_x$ (~50%) to improve the conductivity.

(V1)

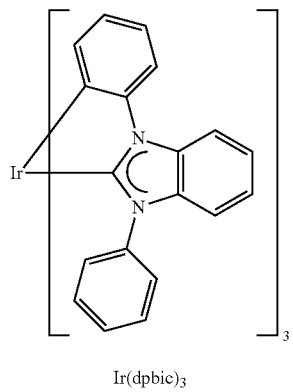

Ir(dpbic)$_3$ (for preparation, see Ir complex (7) in the application WO 2005/019373).

Subsequently, a mixture of 20% by weight of compound (V5)

V5

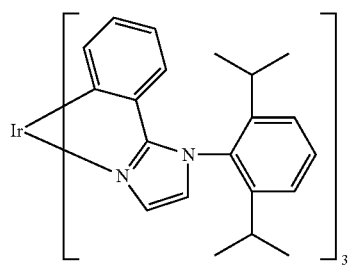

and 80% by weight of the compound 3 are applied by vapor deposition in a thickness of 40 nm, the former compound functioning as an emitter material, the latter as a matrix material.

Subsequently, the material 22 (described in PCT application PCT/EP2009/067120) is applied by vapor deposition with a thickness of 5 nm as an exciton and hole blocker.

22

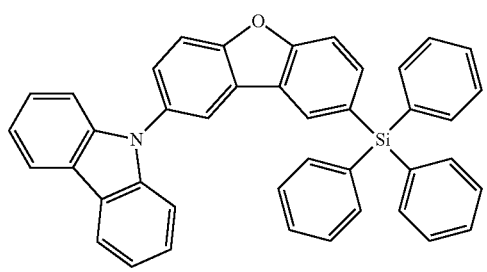

Next, as an electron transporter, a mixture of Liq (50%) and BCP (2,9-dimethyl-4,7-diphenyl-1,10-phenanthroline, 50%) is applied by vapor deposition in a thickness of 40 nm, followed by a 1.0 nm-thick Liq layer and finally a 100 nm-thick Al electrode. All components are bonded in an inert nitrogen atmosphere with a glass cover.

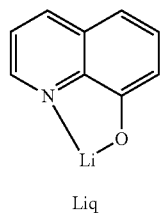

Liq

To characterize the OLED, electroluminescence spectra are recorded at various currents and voltages. In addition, the current-voltage characteristic is measured in combination with the light output emitted. The light output can be converted to photometric parameters by calibration with a photometer.

Comparative Example B2

As in comparative example 1, except that the matrix material used is compound 7 instead of compound 3.

Inventive Example B1

As in comparative example B1, except that the matrix material used is compound 11 instead of compound 3.

| Compound | Current efficiency at 300 cd/m$^2$ | EQE at 300 cd/m$^2$ | Lifetime at 4000 cd/m$^2$ | Color |
|---|---|---|---|---|
| 3 | 100 | 100 | 100 | X = 0.197 |
|   |     |     |     | Y = 0.361 |
| 7* | 5 | 8.5 | 51 (at 1000 cd/m$^2$) | X = 0.559 |
|    |   |     |                        | Y = 0.379 |
| 11 | 113 | 113 | 260 | X = 0.195 |
|    |     |     |     | Y = 0.354 |

*Very strong exciplex formation in the diode, as a result of which the color is red instead of light blue.

C White OLEDs

High-efficiency phosphorescent emitters are one of the prerequisites for the development of high-efficiency white-emitting organic light-emitting diodes (OLEDs) for display and illumination applications.

In this context, a high-efficiency emitter is normally introduced as a dopant in a concentration between 1% and 20% into a matrix material with appropriate energy and triplet levels. In addition, in order to achieve a maximum efficiency, it is necessary to position, adjoining the emitter layers, appropriate charge carrier blocker materials (in order to prevent further transport of the charge carriers into layers which do not radiate with high efficiency or even quenching at the contacts), and also exciton blocker material (in order to prevent loss of the charge carriers into adjoining layers). Therefore, both the matrix materials and the blocker materials and the combination of the corresponding layers are crucial for enabling high-efficiency OLEDs. The properties of the matrix materials used to date (e.g. TPBI, BCP, BPhen) for blue phosphorescent emitters are inadequate with regard to lifetime and efficiency.

2,2',2"-(1,3,5-benzenetriyl)tris(1-phenyl-1H-benzimidazole)=TPBI
2,9-dimethyl-4,7-diphenyl-1,10-phenanthroline=BCP
4,7-diphenyl-1,10-phenanthroline=BPhen It has been found that the material 5 (see synthesis example A5) has particularly good suitability as a matrix material, especially for blue emitters, more preferably for light blue emitters.

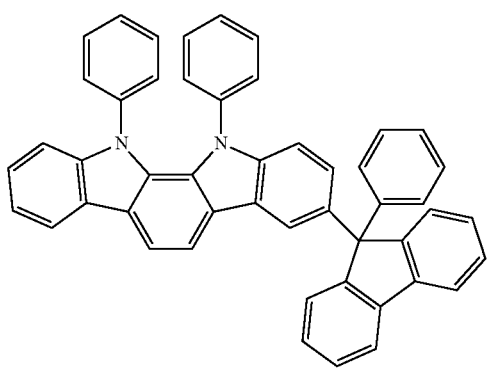

(5)

A stable matrix for light blue emitters is essential for the production of white OLEDs. By way of example, configurations for fully phosphorescent white components with very high efficiency values (quantum efficiencies up to 20%, see working example C2) were developed. By way of example, the following layer sequence was used: hole-injecting contact/ . . . /red phosphorescent emission layer/green phosphorescent emission layer/blue phosphorescent emission layer/ . . . /electron-injecting contact, in which the material 5 can be used advantageously at least as matrix material for blue or else for green or red.

The high energy difference between HOMO (highest occupied molecular orbital) and LUMO (lowest unoccupied molecular orbital) which is needed for phosphorescent blue emitters constitutes a challenge for synthetic chemistry. Usually, the formation of a high band gap often has a counterproductive effect on the charge carrier transport capacity. It has been found that the charge transport properties of the carbazole derivatives of the formulae (I), (II) and (III) are good both for holes and for electrons, in order to be able to build white light-emitting diodes with low voltage and high quantum efficiency, which is shown by the example of compound 5. For instance, a brightness of 1000 cd/m² with white color coordinates (0.419/0.415) is achieved at only 3.72V (see working example C1). This ambipolar character of the carbazole derivatives of the formulae (I), (II) and (III) is particularly advantageous.

In the component, the use of the pure of the carbazole derivatives of the formulae (I), (II) and (III) as matrix, and also a combination of two matrix materials, has been found to be advantageous. The carbazole derivatives of the formulae (I), (II) and (III) used as the matrix interact optimally, with their dipole, with the organometallic emitter, which is shown by the example of compound 5. This means that these materials have excellent suitability as a matrix for high-efficiency phosphorescent emitters. As a result of the good solubility of the emitter in this matrix, it does not tend to aggregate, and annihilation effects are avoided.

Working Examples

Working Example C1

A layer structure and typical corresponding characteristics are shown hereinafter by way of example for a fully phosphorescent white OLED with material 5 as matrix material for a blue dye.

Layer Structure
20 nm 10% Mo 3+90% NPB
10 nm NPB
10 nm NPB:TPBi:ADS076 (70:20:10)
3 nm mCPy:Ir(ppy)3 (90:10)
5, 10 nm compound 5:V5 (emitter) (85:15)
3 nm HBL
30 nm TPBi
20 nm 50% BCP+50% $Cs_2CO_3$
200 nm Al

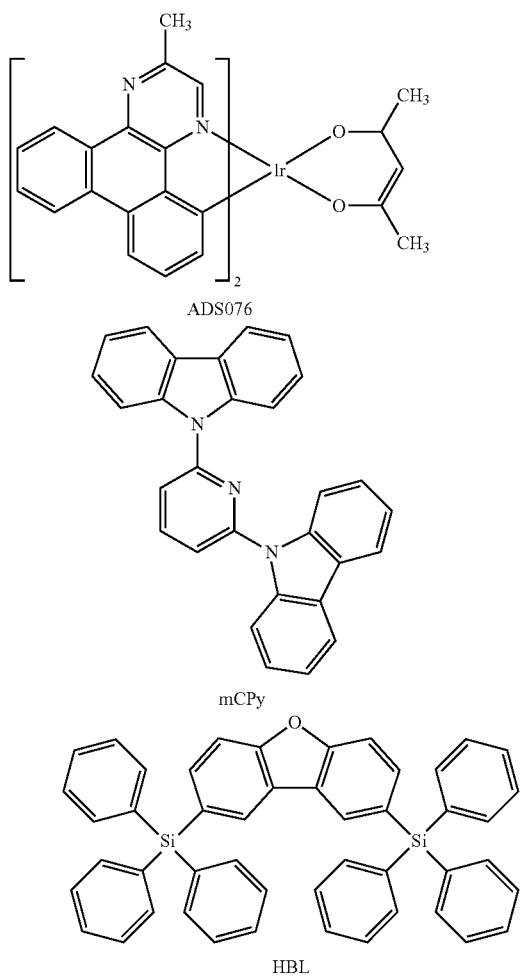

Typical Characteristics:
All values were measured at 1000 cd/m².

|  | 5 nm EML[1] | 10 nm EML[1] |
|---|---|---|
| U[2] | 3.72 V | 3.82 V |
| CIE[3] | 0.419/0.415 | 0.364/0.417 |
| Peff[4] | 32.67 lm/W | 34.47 lm/W |
| EQE[5] | 17.84% | 18.73% |

[1]Thickness of the emission layer
[2]Voltage
[3]Comission internationale l'eclairage (CIE standard valency system)
[4]Efficiency
[5]External quantum efficiency In combination with the appropriate transport and blocker materials, such as

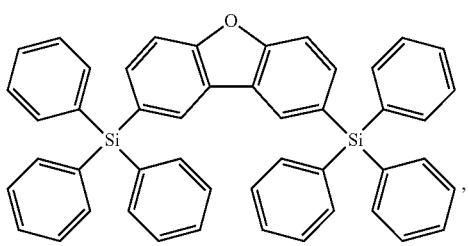 [SMILES: c1ccc([Si](c2ccccc2)(c2ccccc2)c2ccc3oc4ccc([Si](c5ccccc5)(c5ccccc5)c5ccccc5)cc4c3c2)cc1]

it is possible with appropriate phosphorescent emitters to achieve very high quantum efficiency and power efficiency values, low voltages (which indicates sufficiently good transport properties of the material) and good lifetime values.

The high quantum efficiency of the white diode and of the spectrum shows that some of the recombination takes place efficiently on the blue phosphorescent dopant. This means that, as a result of the solvent properties of the matrix, good energy transfer takes place from the matrix material to the triplet emitter and, accordingly, the triplet level for light blue emitters is sufficient, from which it follows that the triplet level for corresponding relatively long-wave dopants is typically sufficient. Advantageously, it is therefore possible only for few of the excitons formed on the matrix 5 to decompose nonradiatively.

Since 5 in this case functions as the sole matrix for the blue phosphorescent dye, the material must transport both electrons and holes efficiently, since both red and blue emission is evident.

Working Example C2

A layer structure and typical corresponding characteristics are shown hereinafter by way of example for a phosphorescent white OLED with material 5 as a component of the matrix in a blue emission layer.

Layer Structure:
20 nm 10% $MoO_x$+90% NPB
10 nm NPB
10 nm NPB:TPBi:ADS076 (70:20:10)
3 nm mCPy:Ir(ppy)3 (90:10)
5, 10 nm mCPy:compound 5:V5 (emitter) (45:45:10)
3 nm HBL
30 nm TPBi
20 nm 50% BCP+50% $Cs_2CO_3$
200 nm Al
Typical Characteristics:
All values were measured at 1000 cd/m².

|  | 5 nm EML[1] | 10 nm EML[1] |
| --- | --- | --- |
| U[2] | 3.87 V | 4.16 V |
| CIE[3] | 0.425/0.409 | 0.401/0.408 |
| Peff[4] | 32.72 lm/W | 31.95 lm/W |
| EQE[5] | 18.89% | 19.74% |

[1]Thickness of the emission layer
[2]Voltage
[3]Comission internationale l'eclairage (CIE standard valency system)
[4]Efficiency
[5]External quantum efficiency The high efficiency values, low voltage and good white color coordinates show that the material is suitable as a matrix constituent, especially for blue dye molecules, but also for relatively long-wave dye molecules, in fully phosphorescent white OLEDs.

The examples given in working examples C3 to C7 which follow are variants of working examples C1 and C2.

Working Example C3

As working examples 1 and 2, except using the following materials instead of

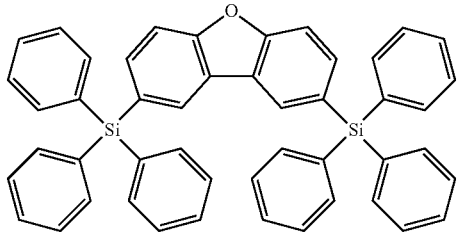 [SMILES: c1ccc([Si](c2ccccc2)(c2ccccc2)c2ccc3oc4ccc([Si](c5ccccc5)(c5ccccc5)c5ccccc5)cc4c3c2)cc1]

as blocker/electron transporters:
2,2',2''-(1,3,5-benzenetriyl)tris(1-phenyl-1H-benzimidazole)
2-(4-biphenylyl)-5-(4-tert-butylphenyl)-1,3,4-oxadiazole
2,9-dimethyl-4,7-diphenyl-1,10-phenanthroline
8-hydroxyquinolinolatolithium
4-(naphthalen-1-yl)-3,5-diphenyl-4H-1,2,4-triazole
1,3-bis[2-(2,2'-bipyridin-6-yl)-1,3,4-oxadiazol-5-yl]benzene
4,7-diphenyl-1,10-phenanthroline
3-(4-biphenylyl)-4-phenyl-5-tert-butylphenyl-1,2,4-triazole
bis(2-methyl-8-quinolinolato)-4-(phenylphenolato)aluminum
6,6'-bis[5-(biphenyl-4-yl)-1,3,4-oxadiazol-2-yl]-2,2'-bipyridyl
2-phenyl-9,10-di(naphthalen-2-yl)anthracene
2,7-bis[2-(2,2'-bipyridin-6-yl)-1,3,4-oxadiazol-5-yl]-9,9-dimethylfluorene
1,3-bis[2-(4-tert-butylphenyl)-1,3,4-oxadiazol-5-yl]benzene
2-(naphthalen-2-yl)-4,7-diphenyl-1,10-phenanthroline
2,9-bis(naphthalen-2-yl)-4,7-diphenyl-1,10-phenanthroline
tris(2,4,6-trimethyl-3-(pyridin-3-yl)phenyl)borane
1-methyl-2-(4-(naphthalen-2-yl)phenyl)-1H-imidazo[4,5-][1,10]phenanthroline Working Example C4

Device configurations like working examples 1 and 2, achieving a white-emitting component by stacking the monochromic OLEDs one on top of another, and a suitable bond by means of what is called a charge generation layer.

Working Example C5

Device configurations like working examples 1 and 2, achieving a white-emitting component with color tunable by appropriate actuation, by structuring the monochromic OLEDs alongside one another.

Working Example C6

Device configurations like working examples 1 and 2, with a red and a green or a green and a blue or a blue and a red or a red, a green and a blue dopant present in a matrix composed of 5 or matrix comprising 5 as one component.

Working Example C7

Like working examples 1 to 6, except using, as contacts, Cu, Au, Pt, Pd, Ph, Os, Al, Mg, Ca, Ba, Ag, Yb, Fe, Co, Ni, Au, ITO (indium tin oxide), AZO (aluminum-doped zinc oxide). Essentially all metals of the main groups, transition metals including the lanthanoids (Yb, Sm, Eu etc.), are suitable. In addition, the alloys of these metals are also suitable.

The invention claimed is:
1. An organic light-emitting diode, organic solar cell or switching element comprising at least one substituted carbazole derivative of the general formula (I), (II) or (III)

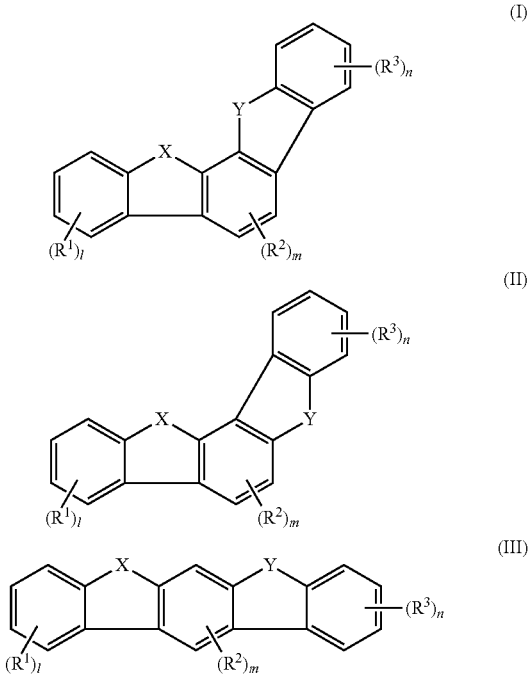

in which
X is $NR^4$, O, S or $PR^4$;
Y is $NR^5$, O, S or $PR^5$;
where at least one of the symbols X and Y is $NR^4$ or $NR^5$;
$R^1$ and $R^3$
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O($OR^6$)), oxycarbonyl (—OC=O($R^6$)), thiocarbonyl (—SC=O($R^6$)), amino (—$NR^6R^7$), OH, pseudohalogen radicals, amido (—C=O($NR^6$)), —$NR^6$C=O($R^7$), phosphonate (—P(O)($OR^6$)$_2$), phosphate (—OP(O)($OR^6$)$_2$), phosphine (—$PR^6R^7$), phosphine oxide (—P(O)$R^6_2$), sulfate (—OS(O)$_2$$OR^6$), sulfoxide (—S(O)$R^6$), sulfonate (—S(O)$_2$$OR^6$), sulfonyl (—S(O)$_2$$R^6$), sulfonamide (—S(O)$_2$$NR^6R^7$), $NO_2$, boronic esters (—OB($OR^6$)$_2$), imino (—C=$NR^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^1$ radicals or two adjacent $R^3$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the $R^1$ or $R^3$ radicals, in the case when it is arranged in the para position to X or Y, is bonded via a heteroatom selected from Si, Ge, O, S or P or via an $sp^3$-hybridized carbon atom;

$R^2$ is substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O($OR^6$)), oxycarbonyl (—OC=O($R^6$)), thiocarbonyl (—SC=O($R^6$)), amino (—$NR^6R^7$), OH, pseudohalogen radicals, amido (—C=O($NR^6$)), —$NR^6$C=O($R^7$), phosphonate (—P(O)($OR^6$)$_2$), phosphate (—OP(O)($OR^6$)$_2$), phosphine (—$PR^6R^7$), phosphine oxide (—P(O)$R^6_2$), sulfate (—OS(O)$_2$$OR^6$), sulfoxide (—S(O)$R^6$), sulfonate (—S(O)$_2$$OR^6$), sulfonyl (—S(O)$_2$$R^6$), sulfonamide (—S(O)$_2$$NR^6R^7$), $NO_2$, boronic esters (—OB($OR^6$)$_2$), imino (—C=$NR^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^2$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

l, n are each independently 0, 1, 2, 3 or 4, where at least l or n is 1, 2, 3 or 4;

m is 0, 1 or 2;

$R^4$, $R^5$
are each independently substituted or unsubstituted $C_6$-$C_{30}$-aryl or substituted or unsubstituted $C_1$-$C_{20}$-alkyl;

$R^6$, $R^7$, $R^8$
are each independently substituted or unsubstituted $C_1$-$C_{20}$-alkyl or substituted or unsubstituted $C_6$-$C_{30}$-aryl, substituted or unsubstituted heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy, $C_6$-$C_{30}$-aryloxy or halogenated $C_1$-$C_{20}$-alkyl radicals;

or two adjacent $R^6$ and $R^7$, $R^6$ and $R^8$ or $R^7$ and $R^8$ radicals, together with the atom to which they are bonded, form a ring having a total of 3 to 12 atoms, where the ring may be saturated or mono- or polyunsaturated and, as well as the atom to which the $R^6$, $R^7$ or $R^8$ radicals are bonded, may have exclusively carbon atoms or one or more further heteroatoms selected from N, O and P, where the ring may be unsubstituted or mono- or poly-substituted and/or may be fused to further 3- to 12-membered rings.

2. The organic light-emitting diode, organic solar cell or switching element according to claim 1, wherein the $R^1$ and $R^3$ radicals in the at least one substituted carbazole derivative of the general formula (I), (II) or (III) are each defined as follows:

$R^1$ and $R^3$
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms, $SiR^6R^7R^8$, amino (—$NR^6R^7$);

$R^6$, $R^7$, $R^8$
are each independently substituted or unsubstituted $C_1$-$C_{20}$-alkyl or substituted or unsubstituted $C_6$-$C_{30}$-aryl, substituted or unsubstituted heteroaryl having 5 to 30 ring atoms, —O—Si($C_1$-$C_{20}$-alkyl)$_3$, —O—Si($C_6$-$C_{30}$-aryl)$_3$;

or two adjacent $R^6$ and $R^7$, $R^6$ and $R^8$ or $R^7$ and $R^8$ radicals, together with the atom to which they are bonded, form a ring having a total of 4 to 8 atoms, where the ring may be saturated or mono- or polyunsaturated and, as well as the atom to which the $R^6$, $R^7$ or $R^8$ radicals are bonded, has exclusively carbon atoms, where the ring may be unsubstituted or mono- or polysubstituted and/or may be fused to further 5- to 8-membered rings.

3. The organic light-emitting diode, organic solar cell or switching element according to claim 2, wherein the $R^1$ and $R^3$ radicals in the at least one substituted carbazole derivative of the general formula (I), (II) or (III) are each defined as follows:

$R^1$ and $R^3$
are each independently substituted or unsubstituted $C_1$-$C_6$-alkyl; substituted or unsubstituted $C_6$-$C_{14}$-aryl; one of the (Ia), (IIa), (IIIa), (Ib), (IIb) or (IIIb) groups below; $SiR^6R^7R^8$ or amino (—$NR^6R^7$);

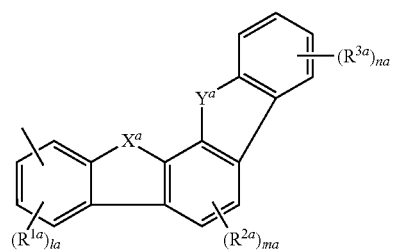
(Ia)

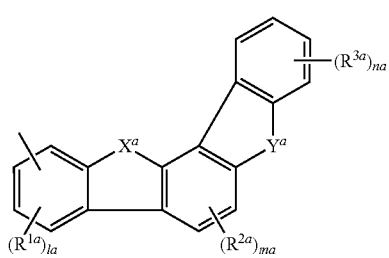
(IIa)

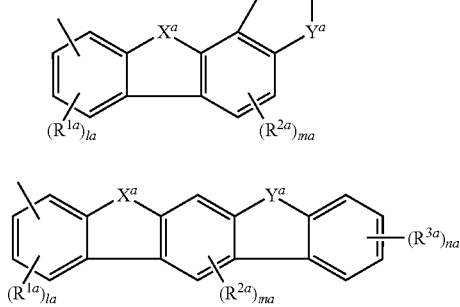
(IIIa)

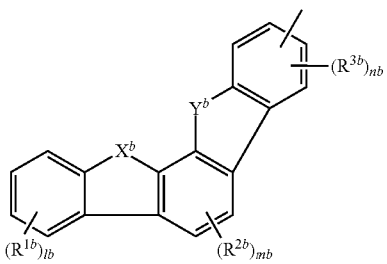
(Ib)

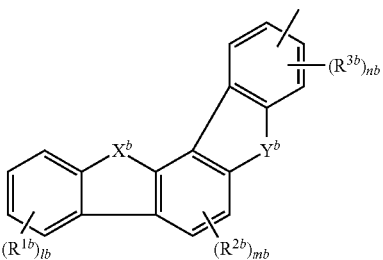
(IIb)

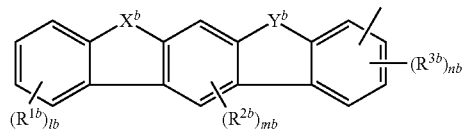
(IIIb)

$R^6$, $R^7$, $R^8$
are each independently substituted or unsubstituted $C_1$-$C_6$-alkyl; substituted or unsubstituted $C_6$-$C_{14}$-aryl; one of the aforementioned (Ia), (IIa), (IIIa), (Ib), (IIb) or (IIIb) groups; —O—Si($C_1$-$C_6$-alkyl)$_3$, —O—Si($C_6$-$C_{30}$-aryl)$_3$; —O—Si($C_1$-$C_6$-alkyl)$_2$-one of the aforementioned (Ia), (IIa), (IIIa), (Ib), (IIb) or (IIIb) groups;

or two adjacent $R^6$ and $R^7$, $R^6$ and $R^8$ or $R^7$ and $R^8$ radicals, together with the atom to which they are bonded, form a ring having a total of 4 to 6 atoms, where the ring may be saturated or mono- or polyunsaturated and, as well as the atom to which the $R^6$, $R^7$ or $R^8$ radicals are bonded, has exclusively carbon atoms, where the ring may be fused to further 5- to 8-membered rings;

where the radicals and indices in the (Ia), (IIa), (IIIa), (Ib), (IIb) or (IIIb) groups are each defined as follows:

$X^a$, $X^b$ are each $NR^{4a}$, $NR^{4b}$, O, S, $PR^{4a}$ or $PR^{4b}$;
$Y^a$, $Y^b$ are each $NR^{5a}$, $NR^{5b}$, O, S, $PR^{5a}$ or $PR^{5b}$;
where at least one of the symbols $X^a$, $X^b$ or $Y^a$, $Y^b$ is $NR^{4a}$, $NR^{4b}$ or $NR^{5a}$, $NR^{5b}$;

$R^{1a}$, $R^{1b}$ and $R^{3a}$, $R^{3b}$
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O(O$R^6$)), oxycarbonyl (—OC=O($R^6$)), thiocarbonyl (—SC=O($R^6$)), amino (—$NR^6R^7$), OH, pseudohalogen radicals, amido (—C=O($NR^6$)), —$NR^6$C=O($R^7$), phosphonate (—P(O)(O$R^6$)$_2$), phosphate (—OP(O)(O$R^6$)$_2$), phosphine (—P$R^6R^7$), phosphine oxide (—P(O)R$^6_2$), sulfate (—OS(O)$_2$OR$^6$), sulfoxide (—S(O)R$^6$), sulfonate (—S(O)$_2$OR$^6$), sulfonyl (—S(O)$_2$R$^6$), sulfonamide (—S(O)$_2$NR$^6$R$^7$), NO$_2$, boronic esters (—OB(OR$^6$)$_2$), imino (—C=NR$^6$R$^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R$^1$ radicals or two adjacent R$^3$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the R$^1$ or R$^3$ radicals, in the case when it is arranged in the para position to X or Y, is bonded via a heteroatom selected from Si, Ge, O, S or P or via an sp$^3$-hybridized carbon atom;

R$^{2a}$, R$^{2b}$ are each substituted or unsubstituted C$_1$-C$_{20}$-alkyl, substituted or unsubstituted C$_6$-C$_{30}$-aryl, substituted or unsubstituted heteroaryl having 5 to 30 ring atoms or a substituent with donor or acceptor action selected from the group consisting of C$_1$-C$_{20}$-alkoxy, C$_6$-C$_{30}$-aryloxy, C$_1$-C$_{20}$-alkylthio, C$_6$-C$_{30}$-arylthio, SiR$^6$R$^7$R$^8$, halogen radicals, halogenated C$_1$-C$_{20}$-alkyl radicals, carbonyl (—CO(R$^6$)), carbonylthio (—C=O(SR$^6$)), carbonyloxy (—C=O(OR$^6$)), oxycarbonyl (—OC=O(R$^6$)), thiocarbonyl (—SC=O(R$^6$)), amino (—NR$^6$R$^7$), OH, pseudohalogen radicals, amido (—C=O(NR$^6$)), —NR$^6$C=O(R$^7$), phosphonate (—P(O)(OR$^6$)$_2$), phosphate (—OP(O)(OR$^6$)$_2$), phosphine (—PR$^6$R$^7$), phosphine oxide (—P(O)R$^6_2$), sulfate (—OS(O)$_2$OR$^6$), sulfoxide (—S(O)R$^6$), sulfonate (—S(O)$_2$OR$^6$), sulfonyl (—S(O)$_2$R$^6$), sulfonamide (—S(O)$_2$NR$^6$R$^7$), NO$_2$, boronic esters (—OB(OR$^6$)$_2$), imino (—C=NR$^6$R$^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent R$^2$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

l$^a$, l$^b$, n$^a$, n$^b$ are each independently 0, 1, 2, 3 or 4, where at least l or n is 1, 2, 3 or 4;

m$^a$, m$^b$ are each 0, 1 or 2;

R$^{4a}$, R$^{4b}$, R$^{5a}$, R$^{5b}$ are each independently substituted or unsubstituted C$_6$-C$_{30}$-aryl or substituted or unsubstituted C$_1$-C$_{20}$-alkyl;

R$^{6a}$, R$^{6b}$, R$^{7a}$, R$^{7b}$, R$^{8a}$, R$^{8b}$ are each independently substituted or unsubstituted C$_1$-C$_{20}$-alkyl or substituted or unsubstituted C$_6$-C$_{30}$-aryl, substituted or unsubstituted heteroaryl having 5 to 30 ring atoms, —O—Si(C$_1$-C$_{20}$-alkyl)$_3$, —O—Si(C$_6$-C$_{30}$-aryl)$_3$, C$_1$-C$_{20}$-alkoxy, C$_6$-C$_{30}$-aryloxy or halogenated C$_1$-C$_{20}$-alkyl radicals;

or two adjacent R$^6$ and R$^7$, R$^6$ and R$^8$ or R$^7$ and R$^8$ radicals, together with the atom to which they are bonded, form a ring having a total of 3 to 12 atoms, where the ring may be saturated or mono- or polyunsaturated and, as well as the atom to which the R$^6$, R$^7$ or R$^8$ radicals are bonded, may have exclusively carbon atoms or one or more further heteroatoms selected from N, O and P, where the ring may be unsubstituted or mono- or poly-substituted and/or may be fused to further 3- to 12-membered rings.

4. The organic light-emitting diode, organic solar cell or switching element according to claim 1, wherein l, n and m in the at least one substituted carbazole derivative of the general formula (I), (II) or (III) are each defined as follows:

l and n are each independently 0, 1 or 2, where at least l or n is 1 or 2;

m is 0.

5. The organic light-emitting diode, organic solar cell or switching element according to claim 1, wherein at least one R$^1$ or R$^3$ substituent in the at least one substituted carbazole derivative of the general formula (I), (II) or (III) is arranged in the para position to X or Y.

6. The organic light-emitting diode, organic solar cell or switching element according to claim 1, wherein the R$^4$ or R$^5$ substituents in the at least one substituted carbazole derivative of the general formula (I), (II) or (III) are each defined as follows:

R$^4$ and R$^5$ are each independently unsubstituted phenyl, SiR$^6$R$^7$R$^8$-substituted phenyl;

R$^6$, R$^7$, R$^8$ are each independently substituted or unsubstituted C$_1$-C$_6$-alkyl; substituted or unsubstituted C$_6$-C$_{14}$-aryl; one of the (Ia), (IIa), (IIIa), (Ib), (IIb) or (IIIb) groups below; —O—Si(C$_1$-C$_6$-alkyl)$_3$, —O—Si(C$_6$-C$_{30}$-aryl)$_3$; —O—Si(C$_1$-C$_6$-alkyl)$_2$-one of the (Ia), (IIa), (IIIa), (Ib), (IIb) or (IIIb) groups below;

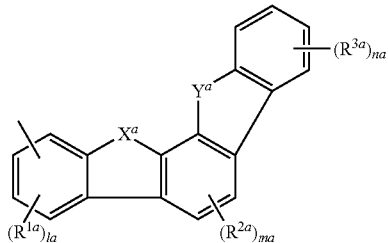

(Ia)

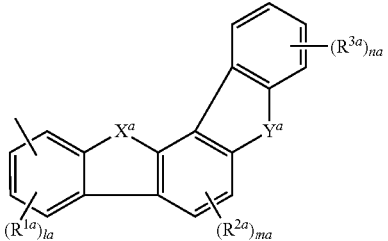

(IIa)

-continued

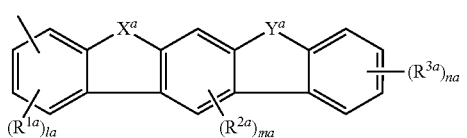 (IIIa)

 (Ib)

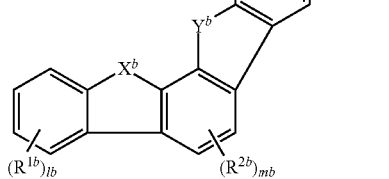 (IIb)

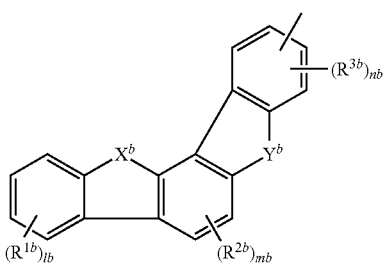 (IIIb)

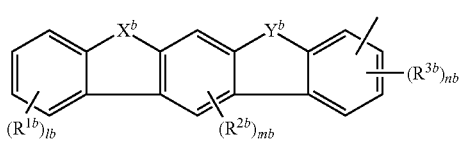

or two adjacent $R^6$ and $R^7$, $R^6$ and $R^8$ or $R^7$ and $R^6$ radicals, together with the atom to which they are bonded, form a ring having a total of 4 to 6 atoms, where the ring may be saturated or mono- or polyunsaturated and, as well as the atom to which the $R^6$, $R^7$ or $R^8$ radicals are bonded, has exclusively carbon atoms, where the ring may be fused to further 5- to 8-membered rings;

where the radicals and indices in the (Ia), (IIa), (IIIa), (Ib), (IIb) or (IIIb) groups are each defined as follows:

$X^a$, $X^b$ are each $NR^{4a}$, $NR^{4b}$, O, S, $PR^{4a}$ or $PR^{4b}$;

$Y^a$, $Y^b$ are each $NR^{5a}$, $NR^{5b}$, O, S, $PR^{5a}$ or $PR^{5b}$;

where at least one of the symbols $X^a$, $X^b$ or $Y^a$, $Y^b$ is $NR^{4a}$, $NR^{4b}$ or $NR^{5a}$, $NR^{5b}$;

$R^{1a}$, $R^{1b}$ and $R^{3a}$, $R^{3b}$ are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O(S$R^6$)), carbonyloxy (—C=O(O$R^6$)), oxycarbonyl (—OC=O($R^6$)), thiocarbonyl (—SC=O($R^6$)), amino (—N$R^6R^7$), OH, pseudohalogen radicals, amido (—C=O(N$R^6$)), —N$R^6$C=O($R^7$), phosphonate (—P(O)(O$R^6$)$_2$), phosphate (—OP(O)(O$R^6$)$_2$), phosphine (—P$R^6R^7$), phosphine oxide (—P(O)$R^6_2$), sulfate (—OS(O)$_2$O$R^6$), sulfoxide (—S(O)$R^6$), sulfonate (—S(O)$_2$O$R^6$), sulfonyl (—S(O)$_2R^6$), sulfonamide (—S(O)$_2$N$R^6R^7$), NO$_2$, boronic esters (—OB(O$R^6$)$_2$), imino (—C=N$R^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^1$ radicals or two adjacent $R^3$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the $R^1$ or $R^3$ radicals, in the case when it is arranged in the para position to X or Y, is bonded via a heteroatom selected from Si, Ge, O, S or P or via an sp$^3$-hybridized carbon atom;

$R^{2a}$, $R^{2b}$ are each substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O(S$R^6$)), carbonyloxy (—C=O(O$R^6$)), oxycarbonyl (—OC=O($R^6$)), thiocarbonyl (—SC=O($R^6$)), amino (—N$R^6R^7$), OH, pseudohalogen radicals, amido (—C=O(N$R^6$)), —N$R^6$C=O($R^7$), phosphonate (—P(O)(O$R^6$)$_2$), phosphate (—OP(O)(O$R^6$)$_2$), phosphine (—P$R^6R^7$), phosphine oxide (—P(O)$R^6_2$), sulfate (—OS(O)$_2$O$R^6$), sulfoxide (—S(O)$R^6$), sulfonate (—S(O)$_2$O$R^6$), sulfonyl (—S(O)$_2R^6$), sulfonamide (—S(O)$_2$N$R^6R^7$), NO$_2$, boronic esters (—OB(O$R^6$)$_2$), imino (—C=N$R^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^2$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

$l^a$, $l^b$, $n^a$, $n^b$ are each independently 0, 1, 2, 3 or 4, where at least l or n is 1, 2, 3 or 4;

$m^a$, $m^b$ are each 0, 1 or 2;

$R^{4a}$, $R^{4b}$, $R^{5a}$, $R^{5b}$ are each independently substituted or unsubstituted $C_6$-$C_{30}$-aryl or substituted or unsubstituted $C_1$-$C_{20}$-alkyl;

$R^{6a}$, $R^{6b}$, $R^{7a}$, $R^{7b}$, $R^{8a}$, $R^{8b}$ are each independently substituted or unsubstituted $C_1$-$C_{20}$-alkyl or substituted or unsubstituted $C_6$-$C_{30}$-aryl, substituted or unsubstituted heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy, $C_6$-$C_{30}$-aryloxy or halogenated $C_1$-$C_{20}$-alkyl radicals;

or two adjacent $R^6$ and $R^7$, $R^6$ and $R^8$ or $R^7$ and $R^8$ radicals, together with the atom to which they are bonded, form a ring having a total of 3 to 12 atoms, where the ring may be saturated or mono- or polyunsaturated and, as well as the atom to which the $R^6$, $R^7$ or $R^8$ radicals are bonded, may have exclusively carbon atoms or one or more further heteroatoms selected from N, O and P, where the ring may be unsubstituted or mono- or poly-substituted and/or may be fused to further 3- to 12-membered rings.

7. The organic light-emitting diode, organic solar cell or switching element according to claim 1, wherein at least one of the $R^1$, $R^2$, $R^3$, $R^4$ or $R^5$ radicals of the substituted carbazole derivative of the general formula (I), (II) or (III) is an Si-comprising radical.

8. The organic light-emitting diode according to claim 1, comprising an anode An and a cathode Ka and a light-emitting layer E arranged between the anode and the cathode, and optionally at least one further layer selected from the group consisting of at least one blocking layer for electrons/excitons, at least one blocking layer for holes/excitons, at least one hole injection layer, at least one hole conductor layer, at least one electron injection layer and at least one electron conductor layer, wherein the at least one substituted carbazole derivative of the general formula (I), (II) or (III) is present in the light-emitting layer E and/or in the at least one further layer.

9. The organic light-emitting diode according to claim 8, wherein the at least one substituted carbazole derivative of the general formula (I), (II), (III) is present in the light-emitting layer E as a matrix material together with at least one emitter material.

10. The organic light-emitting diode according to claim 9, wherein the emitter material used in the light-emitting layer is at least one carbene complex of the general formula (IV)

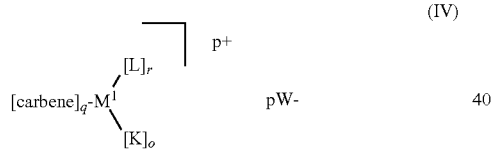

in which the symbols are each defined as follows:
$M^1$ is a metal atom selected from the group consisting of metals of group IB, IIB, IIIB, IVB, VB, VIB, VIIB, the lanthanides and IIIA of the Periodic Table of the Elements (CAS version) in any oxidation state possible for the particular metal atom;
carbene is a carbene ligand which may be uncharged or monoanionic and mono-, bi- or tridentate; the carbene ligand may also be a bis- or triscarbene ligand;
L is a mono- or dianionic ligand;
K is an uncharged mono- or bidentate ligand;
q is the number of carbene ligands, where n is at least 1 and the carbene ligands in the complex of the formula I when q>1 may be the same or different;
r is the number of ligands L, where m may be 0 or ≥1, and the ligands L when r>1 may be the same or different;
o is the number of ligands K, where o may be 0 or ≥1, and the ligands K, when o>1, may be the same or different;
p is the charge of the complex: 0, 1, 2, 3 or 4; preferably 0, 1 or 2, more preferably 0;
W is a monoanionic counterion;
where the sum of q+r+o and the charge p depends on the oxidation state and coordination number of the metal atom used, the charge of the complex and the denticity of the carbene, L and K ligands, and on the charge of the carbene and L ligands, with the condition that n is at least 1.

11. The organic light-emitting diode according to claim 8, wherein the organic light-emitting diode comprises, as at least one further layer, a blocking layer for holes, said blocking layer for holes comprising at least one compound of the general formula (V)

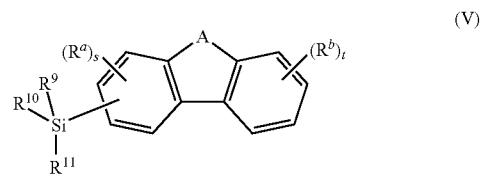

in which:
A is $NR^{12}$, S or O;
$R^{12}$ is substituted or unsubstituted $C_1$-$C_{20}$-alkyl, substituted or unsubstituted $C_6$-$C_{30}$-aryl, or substituted or unsubstituted heteroaryl having from 5 to 30 ring atoms;
$R^9$, $R^{10}$, $R^{11}$
are each independently substituted or unsubstituted $C_1$-$C_{20}$-alkyl or substituted or unsubstituted $C_6$-$C_{30}$-aryl or a structure of the general formula (a)

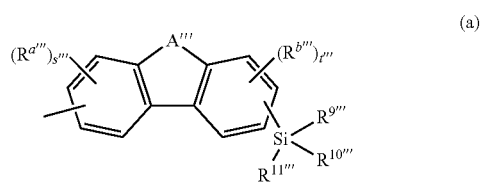

$R^a$, $R^b$
are each independently substituted or unsubstituted $C_1$-$C_{20}$-alkyl, substituted or unsubstituted $C_6$-$C_{30}$-aryl, substituted or unsubstituted heteroaryl having from 5 to 30 ring atoms or a substituent with donor or acceptor action selected from the group consisting of: $C_1$-$C_{20}$-alkoxy, $C_6$-$C_{30}$-aryloxy, $C_1$-$C_{20}$-alkylthio, $C_6$-$C_{30}$-arylthio, $SiR^{12}R^{13}R^{14}$, halogen radicals, halogenated $C_1$-$C_{20}$-alkyl radicals, carbonyl (—CO($R^{12}$)), carbonylthio (—C=O($SR^{12}$)), carbonyloxy (—C=O($OR^{12}$)), oxycarbonyl (—OC=O($R^{12}$)), thiocarbonyl (—SC=O($R^{12}$)), amino (—$NR^{12}R^{13}$), OH, pseudohalogen radicals, amido (—C=O($NR^{12}$)), —$NR^{12}$C=O($R^{13}$), phosphonate (—P(O)($OR^{12}$)$_2$), phosphate (—OP(O)($OR^{12}$)$_2$), phosphine (—$PR^{12}R^{13}$), phosphine oxide (—P(O)$R^{12}{}_2$), sulfate (—OS(O)$_2OR^{12}$), sulfoxide (—S(O)$R^{12}$), sulfonate (—S(O)$_2OR^{12}$), sulfonyl (—S(O)$_2R^{12}$), sulfonamide (—S(O)$_2$$NR^{12}R^{13}$), $NO_2$, boronic esters (—OB($OR^{12}$)$_2$), imino (—C=$NR^{12}R^{13}$), borane radicals, stannane radicals, hydrazine radicals, hydrazone radicals, oxime radicals, nitroso groups, diazo groups, vinyl groups, sulfoximines, alanes, germanes, boroximes and borazines;
$R^{12}$, $R^{13}$, $R^{14}$
are each independently substituted or unsubstituted $C_1$-$C_{20}$-alkyl, or substituted or unsubstituted $C_6$-$C_{30}$-aryl;

s, t are each independently 0, 1, 2 or 3; where, in the case when q or r is 0, all substitutable positions of the aryl radical are substituted by hydrogen, where the radicals and indices in the group of the formula (a) A''', $R^{9'''}$, $R^{10'''}$, $R^{11'''}$, $R^{a'''}$, $R^{b'''}$, s''' and t''' are each independently as defined for the radicals and indices of the compounds of the general formula (V) A, $R^9$, $R^{10}$, $R^{11}$, $R^a$, $R^b$, s and t.

12. A light-emitting layer comprising at least one substituted carbazole derivative of the general formula (I), (II) or (III) according to claim 1 and at least one emitter material.

13. An organic light-emitting diode, an organic solar cell or a switching element comprising substituted carbazole derivatives of the general formula (I), (II) or (III) according to claim 1 as matrix material, hole/exciton blocker material and/or electron/exciton blocker material and/or hole injection material and/or electron injection material and/or hole conductor material and/or electron conductor material.

14. A device selected from the group consisting of stationary visual display units, illuminations, and mobile visual display units; keyboards; garments; furniture and wallpaper comprising at least one organic light-emitting diode according to claim 1.

15. A carbazole derivative of the general formula (I), (II) or (III)

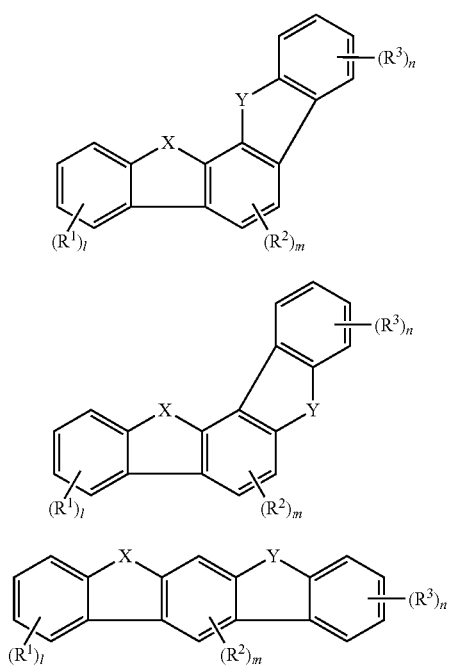

in which
X is $NR^4$, O, S or $PR^4$;
Y is $NR^5$, O, S or $PR^5$;
where at least one of the symbols X and Y is $NR^4$ or $NR^5$;
$R^1$ and $R^3$
are each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O (O$R^6$)), oxycarbonyl (—OC=O($R^6$)), thiocarbonyl (—SC=O($R^6$)), amino (—N$R^6R^7$), OH, pseudohalogen radicals, amido (—C=O(N$R^6$)), —N$R^6$C=O($R^7$), phosphonate (—P(O)(O$R^6$)$_2$), phosphate (—OP(O)(O$R^6$)$_2$), phosphine (—P$R^6R^7$), phosphine oxide (—P(O)$R^6_2$), sulfate (—OS(O)$_2$O$R^6$), sulfoxide (—S(O)$R^6$), sulfonate (—S(O)$_2$O$R^6$), sulfonyl (—S(O)$_2R^6$), sulfonamide (—S(O)$_2$N$R^6R^7$), NO$_2$, boronic esters (—OB(O$R^6$)$_2$), imino (—C=N$R^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^1$ radicals or two adjacent $R^3$ radicals, in each case together with the carbon atoms to which they are bonded, form a ring having a total of 3 to 12 atoms, where the ring may be saturated or mono- or polyunsaturated and, as well as carbon atoms, may have one or more heteroatoms selected from N, O and P, where the ring may be unsubstituted or mono- or polysubstituted and/or may be fused to further 3- to 12-membered rings;

where at least one of the $R^1$ or $R^3$ radicals, in the case when it is arranged in the para position to X or Y, is bonded via a heteroatom selected from Si, Ge, O, S or P or via an $sp^3$-hybridized carbon atom;

$R^2$ is substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action selected from the group consisting of $C_1$-$C_{20}$-alkoxy, $C_6$-$C_{30}$-aryloxy, $C_1$-$C_{20}$-alkylthio, $C_6$-$C_{30}$-arylthio, $SiR^6R^7R^8$, halogen radicals, halogenated $C_1$-$C_{20}$-alkyl radicals, carbonyl (—CO($R^6$)), carbonylthio (—C=O($SR^6$)), carbonyloxy (—C=O(O$R^6$)), oxycarbonyl (—OC=O($R^6$)), thiocarbonyl (—SC=O($R^6$)), amino (—N$R^6R^7$), OH, pseudohalogen radicals, amido (—C=O(N$R^6$)), —N$R^6$C=O($R^7$), phosphonate (—P(O)(O$R^6$)$_2$), phosphate (—OP(O)(O$R^6$)$_2$), phosphine (—P$R^6R^7$), phosphine oxide (—P(O)$R^6_2$), sulfate (—OS(O)$_2$O$R^6$), sulfoxide (—S(O)$R^6$), sulfonate (—S(O)$_2$O$R^6$), sulfonyl (—S(O)$_2R^6$), sulfonamide (—S(O)$_2$N$R^6R^7$), NO$_2$, boronic esters (—OB(O$R^6$)$_2$), imino (—C=N$R^6R^7$), borane radicals, stannane radicals, hydrazine radicals, hydrazone radicals, oxime radicals, nitroso groups, diazo groups, vinyl groups, sulfoximines, alanes, germanes, boroximes and borazines;

or two adjacent $R^2$ radicals, in each case together with the carbon atoms to which they are bonded, form a ring composed of 3 to 12 carbon atoms, where the ring may be saturated or mono- or polyunsaturated, where the ring may be unsubstituted or mono- or polysubstituted and/or may be fused to further 3- to 12-membered rings;

l, n are each independently 0, 1, 2, 3 or 4, where at least l or n is 1, 2, 3 or 4;

m is 0, 1 or 2;

$R^4$, $R^5$
are each independently substituted or unsubstituted $C_6$-$C_{30}$-aryl or substituted or unsubstituted $C_1$-$C_{20}$-alkyl;

$R^6$, $R^7$, $R^8$
are each independently substituted or unsubstituted $C_1$-$C_{20}$-alkyl or substituted or unsubstituted $C_6$-$C_{30}$- aryl, substituted or unsubstituted heteroaryl having 5 to 30 ring atoms, —O—Si($C_1$-$C_{20}$-alkyl)$_3$, —O—Si($C_6$-$C_{30}$-aryl)$_3$, $C_1$-$C_{20}$-alkoxy, $C_6$-$C_{30}$-aryloxy or halogenated $C_1$-$C_{20}$-alkyl radicals;

or two adjacent $R^6$ and $R^7$, $R^6$ and $R^8$ or $R^7$ and $R^8$ radicals, together with the atom to which they are bonded, form a ring having a total of 3 to 12 atoms, where the ring may be saturated or mono- or polyunsaturated and, as well as the atom to which the $R^6$, $R^7$ or $R^8$ radicals are bonded, may have exclusively carbon atoms or one or more further heteroatoms selected from N, O and P, where the ring may be unsubstituted or mono- or poly-substituted and/or may be fused to further 3- to 12-membered rings.

* * * * *

UNITED STATES PATENT AND TRADEMARK OFFICE
CERTIFICATE OF CORRECTION

PATENT NO. : 8,637,857 B2  Page 1 of 1
APPLICATION NO. : 13/080091
DATED : January 28, 2014
INVENTOR(S) : Nicolle Langer et al.

It is certified that error appears in the above-identified patent and that said Letters Patent is hereby corrected as shown below:

On the title page, Item (73), the Assignees' Information is incorrect. Item (73) should read:

--(73) Assignees: BASF SE, Ludwigshafen (DE); Koninklijke Philips Electronics N.V., Eindhoven (NL); Osram Opto Semiconductors GmbH, Regensburg (DE)--

Signed and Sealed this
Twenty-second Day of April, 2014

Michelle K. Lee
*Deputy Director of the United States Patent and Trademark Office*